United States Patent
Brubacher

(10) Patent No.: US 11,446,660 B2
(45) Date of Patent: *Sep. 20, 2022

(54) ORGANISM EVALUATION SYSTEM AND METHOD OF USE

(71) Applicant: SoBru Solutions, Inc., Fullerton, CA (US)

(72) Inventor: John Miles Brubacher, La Mirada, CA (US)

(73) Assignee: SCANLOGX, INC, Waco, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/995,648

(22) Filed: Aug. 17, 2020

(65) Prior Publication Data

US 2021/0060558 A1    Mar. 4, 2021

Related U.S. Application Data

(63) Continuation-in-part of application No. 15/589,977, filed on May 8, 2017, now Pat. No. 10,748,278, (Continued)

(51) Int. Cl.
*B01L 3/00* (2006.01)
*C12M 3/00* (2006.01)
(Continued)

(52) U.S. Cl.
CPC ....... *B01L 3/502715* (2013.01); *C12M 41/36* (2013.01); *G01N 15/1429* (2013.01);
(Continued)

(58) Field of Classification Search
CPC ........ C12M 29/10; G01N 15/147; C12Q 1/04
See application file for complete search history.

(56) References Cited

U.S. PATENT DOCUMENTS

| 4,380,392 A | 4/1983 | Karabegov et al. |
| 4,824,449 A | 4/1989 | Majoros |

(Continued)

FOREIGN PATENT DOCUMENTS

| CN | 101750435 A | 6/2010 |
| EP | 0530490 A1 | 3/1992 |

(Continued)

OTHER PUBLICATIONS

International Search Report, PCT/US13/46334, dated Nov. 1, 2013.
(Continued)

*Primary Examiner* — Nathan A Bowers
(74) *Attorney, Agent, or Firm* — Master Key IP; Jeromye V. Sartain

(57) ABSTRACT

An organism evaluation system for analyzing organisms within a fluid flow, comprising one or more of a stimulation section comprising a means for inducing a motive response in a living organism within the fluid flow passing through the stimulation section and a shepherding section comprising a means for separating such an organism from the fluid flow, a flow normalizing section in fluid communication with the stimulation section and/or shepherding section, and a viewing section in fluid communication with the flow normalizing section, the viewing section comprising a body having formed therein a body cavity defining a viewing port, the viewing section further comprising an optical system mounted relative to the body for viewing the fluid flow within the viewing port through a cavity first opening, whereby image data relating to the fluid flow and organisms therein is acquired via the optical system for analysis.

20 Claims, 27 Drawing Sheets

Related U.S. Application Data which is a continuation-in-part of application No. 14/408,562, filed as application No. PCT/US2013/046334 on Jun. 18, 2013, now Pat. No. 9,644,229.

(60) Provisional application No. 61/661,011, filed on Jun. 18, 2012.

(51) Int. Cl.
  *C12M 1/34* (2006.01)
  *G01N 15/14* (2006.01)
  *G06T 7/00* (2017.01)

(52) U.S. Cl.
  CPC ..... *G06T 7/0012* (2013.01); *B01L 2200/0636* (2013.01); *B01L 2200/0652* (2013.01); *G06T 2207/30242* (2013.01)

(56) References Cited

U.S. PATENT DOCUMENTS

| | | | |
|---|---|---|---|
| 5,459,069 | A | 10/1995 | Palsson et al. |
| 6,313,943 | B1 | 11/2001 | Ikado et al. |
| 6,498,862 | B1 | 12/2002 | Pierson et al. |
| 7,901,937 | B2 | 3/2011 | Srienc et al. |
| 7,999,937 | B1 | 8/2011 | Srivastava et al. |
| 8,153,950 | B2 | 4/2012 | Kiesel et al. |
| 2002/0094584 | A1 | 7/2002 | Shieh et al. |
| 2003/0175687 | A1 | 9/2003 | Tippet |
| 2004/0136870 | A1 | 7/2004 | Kochy et al. |
| 2006/0051858 | A1 | 3/2006 | Combette |
| 2006/0210962 | A1 | 9/2006 | Imaizumi et al. |
| 2006/0257993 | A1 | 11/2006 | McDevitt et al. |
| 2009/0093045 | A1 | 4/2009 | Takenaka et al. |
| 2009/0162887 | A1 | 6/2009 | Kaduchak et al. |
| 2010/0041122 | A1 | 2/2010 | Ragsdale |
| 2010/0116647 | A1 | 5/2010 | Kommuller et al. |
| 2010/0157291 | A1 | 6/2010 | Kiesel et al. |
| 2010/0273208 | A1 | 10/2010 | Takenaka et al. |
| 2011/0096327 | A1 | 4/2011 | Papautsky et al. |
| 2012/0115723 | A1 | 5/2012 | Stimson et al. |
| 2012/0214224 | A1 | 8/2012 | Chan |
| 2015/0167045 | A1 | 6/2015 | Brubacher |
| 2018/0372612 | A1 | 12/2018 | Masuda |

FOREIGN PATENT DOCUMENTS

| | | |
|---|---|---|
| EP | 2026057 A2 | 2/2009 |
| JP | 2005106454 A1 | 3/2008 |
| JP | 2012020218 A | 2/2012 |
| WO | 2008130977 A2 | 10/2008 |

OTHER PUBLICATIONS

Malits et al. "Effect of turbulence and viruses on prokaryotic cell size, production and diversity" Aquatic Microbial Ecology 54, No. 3 (2009): 243-254. Abstract.

European Search Report, EP 13807665, dated Jan. 5, 2016.

Odom et al. "RECLAMATION, Managing Water in the West—Developing Underwater Video Technology for Sampling Pelagic Delta Fishes. 'SmeltCam II'," date unknown (obtained Jan. 23, 2017).

"RECLAMATION, Managing Water in the West—Fiscal Year 2011 Annual Progress Report—SmeltCam: Underwater Video Technology for Identifying and Measuring Abundance of Pelagic Fishes," date unknown (obtained Feb. 15, 2018).

Feyrer et al. "SmeltCam: Underwater Video Codend for Trawled Nets with an Application to the Distribution of the Imperiled Delta Smelt"—OpenAccess PLOS ONE, Jul. 2013, vol. 8, Issue 7 (obtained Feb. 15, 2018).

Website screen shots taken from sure.works page entitled "Smeltcam: System for counting and identifying fish." at http://sure.works/smeltcam/ (obtained Feb. 15, 2018).

Website screen shots taken from ca.water.usgs.gov page entitled "Delta Smelt Early Warning Studies: Application of the SmeltCam to Describe Processes Influencing Delta Smelt Distribution and Movements" at https://ca.water.usgs.gov/projects/2015-34.html (obtained Feb. 15, 2018).

Website screen shots taken from fishbio.com page entitled "Automated Fisheries Monitoring Solutions" at http://fishbio.com/automated_monitoring (obtained Feb. 15, 2018).

Website printout from fluidimaging.com home page at http://fluidimaging.com (obtained Nov. 11, 2019).

Johnson "Enhanced early detection and enumeration of zebra mussel (*Dreissena* spp.) veligers using cross-polarized light microscopy"—Hydrobiologia, 312: 139-146, 1995.

Fluid Imaging Technologies, FlowCAM Manual, Version 3.0, 2011 (Year: 2011).

Olson et al., "A submersible imaging-in-flow instrument to analyze nano- and microplankton: Imaging FlowCytobot," Limnology and Oceanography: Methods, 5, pp. 195-203 Year: 2007).

ORGANISM EVALUATION SYSTEM AND METHOD OF USE

RELATED APPLICATIONS

This is a continuation-in-part application and so claims the benefit pursuant to 35 U.S.C. § 120 of a prior filed and co-pending U.S. Non-Provisional patent application Ser. No. 15/589,977 filed May 8, 2017, and entitled "Organism Evaluation System and Method of Use," which is itself a continuation-in-part application under 35 U.S.C. § 120 of U.S. Non-Provisional patent application Ser. No. 14/408,562 filed Dec. 16, 2014, and entitled "Microorganism Evaluation System," now U.S. Pat. No. 9,644,229 issued May 9, 2017, which is a U.S. national stage application under 35 U.S.C. § 371 of International Patent Application Ser. No. PCT/US2013/046334 filed Jun. 18, 2013, and entitled "Microorganism Evaluation System," which itself claims priority pursuant to 35 U.S.C. § 119(e) to and is entitled to the filing date of U.S. Provisional Patent Application Ser. No. 61/661,011 filed Jun. 18, 2012, and entitled "Microorganism Evaluation System." The contents of the aforementioned applications are incorporated herein by reference.

BACKGROUND

The subject of this patent application relates generally to testing, evaluation, or monitoring systems, and more particularly to evaluation systems for determining organism viability, count and/or identification.

The following description includes information that may be useful in understanding the present invention. It is not an admission that any of the information provided herein is prior art or relevant to the presently claimed invention, or that any publication specifically or implicitly referenced is prior art.

Applicant(s) hereby incorporate herein by reference any and all patents and published patent applications cited or referred to in this application, to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

By way of background, water is of course one of the world's most critical natural resources, and as populations increase and weather and environmental effects fluctuate a variety of challenges are presented in connection with water usage particularly as it relates to protecting and preserving ecosystems and fragile, endangered or other such species within such ecosystems potentially effected by water usage. Water usage, whether for potable applications, irrigation, cooling, ballast exchange, or the like, at some point inherently involves an "intake" where the source water is acquired or taken into a system and/or an "outlet" where water is returned from the system.

One exemplary context is that a number of industries are affected by regulations relating to water treatment, such as ballast water treatment systems ("BWTS") on ships and the like. Such regulations require that microorganisms be effectively treated (killed) by the BWTS before such water is returned to the ocean or other body of water. Generally speaking, Zooplankton in the size range of approximately 10 to 50 microns is an "indicator" microorganism used to determine the effectiveness of treatment. To date, monitoring of the effectiveness of such BWTS has largely been handled through samples submitted to a lab, there most often involving human examination under a microscope. Such approaches to compliance assessment have numerous shortcomings in terms of accuracy, speed, and cost. Similarly, flow cytometry systems, though offering relatively higher throughput, are also lacking in terms of viability determination (determinations regarding whether an organism is living) and portability for field or deployed uses.

The following art defines the present state of this field:

International Pub. No. WO2005106454S dated Mar. 21, 2008 is directed to subject matter teaching that to be viable in the antigen by specifically labeled, as among a viable microorganisms can be detected rapidly in a short time, the reliability of inspection and detection method can also be guaranteed. Such as an antigen, *Escherichia coli*, viable to be examined in the antigen (target bacteria 12) enzymatic decomposition by the sign material 13 is brought into action after generating a labeled antigen 14, specifically to subject the specific coupling in a stationary phase is formed by fixing an antibody, an antigen labeled 14 thereof to and captured.

U.S. Patent Application Pub. No. US 2009/0162887 to Kaduchak et al. dated Jun. 25, 2009, is directed to a method and apparatus for acoustically manipulating one or more particles.

U.S. Patent Application Pub. No. US 2010/0041122 to Ragsdale dated Feb. 18, 2010, is directed to membrane-encased structures such as biological cells, liposomes, and vesicles, conveyed through one or more channels in a rotating disk for individual exposure to optical elements or to electrodes, for purposes of transfection or flow cytometry. The rotation of the disk serves either to provide centrifugal force to urge the cells against one wall of the channel and in certain embodiments to move the cells through the channels, or to draw cells at preselected times or intervals into the exposure zone, or all three.

U.S. Patent Application Pub. No. US 2010/0116647 to Kornmuller et al. dated May 13, 2010, is directed to a water treatment plant, in particular ballast water treatment plant, for removing sediments and/or removing and/or destroying living organisms, which has at least one filter unit (B) and at least one disinfection unit (C), wherein the plant has a detection unit (D) by means of which the number of living organisms of a presettable size per unit volume of water can be determined, and in that the plant has a control unit, by means of which the disinfection unit (C) can be controlled as a function of the number of living organisms which has been determined.

U.S. Patent Application Pub. No. US 2010/0157291 to Kiesel et al. dated Jun. 24, 2010, is directed to a method wherein sensors can be used to obtain encoded sensing results from objects that have nonuniform relative motion. A photosensor or impedance-based sensor, for example, can obtain sensing results from objects that have relative motion within a sensing region relative to the sensor, with the relative motion being, for example, periodically varying, randomly varying, chirp-varying, or modulated relative motion that completes at least one modulation cycle within the sensing region. Relative motion can be caused by varying objects' speed and/or direction or by controlling flow of fluid carrying objects, movement of a channel, movement of a support structure, movement of a sensor, and/or pattern movement. A fluidic implementation can include shaped channel wall parts and/or a displacement component causing time-varying lateral displacement. A support structure implementation can include a scanner device and a rotary device that respectively control scanning and rotating movement of a movable support structure or of a sensor.

Japanese Patent Application Pub. No. JP 2012020218 dated Feb. 2, 2012, is directed to a system wherein the liquid supplied to the ballast tank 103 in the sterilization of microorganisms hydrophyte for sterilization device 101 and 1, ballast water in the ballast tank 103 for sterilization device 102 and the second, first the liquid 1 sterilization treatment device 101 for supplying the chest 104 of the ballast from the ballast tank 103, 105 and connected to a water supply line, 2 sterilization treatment device 102 includes a first liquid containing sodium chloride, sodium hypochlorite by electrolysis in the electrolytic cell for generating the ballast water treatment system is provided.

U.S. Pat. No. 8,153,950 to Kiesel et al. dated Apr. 10, 2012, is directed to an encoder/sensor can obtain sensing results from objects in an encoding/sensing region; a trigger detector can respond to objects in a trigger detection region, providing respective trigger signals; and a relative motion component can cause relative motion of objects into the trigger detection region, from it into the encoding/sensing region, and within the encoding/sensing region. In response to an object's trigger signal, control circuitry can cause the encoder/sensor and/or the relative motion component to operate so that the encoder/sensor obtains sensing results indicating a time-varying waveform and processing circuitry can obtain data from the sensing results indicating a time-varying waveform. The time-varying waveform can include information resulting from the relative motion within the encoding/sensing region. The encoder/sensor and trigger detector can be implemented, for example, with discrete components or as sets of cells in a photosensing array on an integrated circuit.

U.S. Patent Application Pub. No. US 2012/0115723 to Stimson et al. dated May 10, 2012, is directed to a composition for treating waters, e.g. ballast water or injection water for oil recovery, to kill in-situ aquatic invasive species comprises at least one biocide capable of killing both animal and plant micro-organisms. The at least one biocide preferably comprises Brilliant Green, Gentian Violet, and/or erythrosine, and a wetting agent or detergent-like compound such as CTAB or CTAC. The invention also relates to a system for treating ballast water in situ comprising means for injecting a composition for treating ballast water; means for measuring the flow rate or amount of ballast water to be treated; means for controlling the dosing of the composition; and means for storing or receiving the composition. The invention also relates to a method of detecting viable aquatic organisms in ballast water in situ comprising detecting metabolism in viable micro-organisms in ballast water and, therefore, measuring the efficacy of any treatment.

U.S. Patent Application Pub. No. US 2012/0214224 to Chan dated Aug. 23, 2012, is directed to the context wherein values of clinical properties are normally measured by taking a sample from a patient, mixing an aliquot with a reagent, placing the mixture into a selected instrument, and measuring a property. If another property is required, another measurement sequence must be created. This can be efficient on a large scale, for example in a centralized laboratory, but is inefficient on a small scale. It is shown that by using measurement systems based on manipulation of flowing streams, clinical assays can be performed by a hand held device. This flow based system allows complex assays to be performed in remote locations with automated portable instruments that can be flexible enough to conduct a wide variety of assays.

U.S. Patent Application Pub. No. US 2006/0257993 to McDevitt dated Nov. 16, 2006, is directed to an analyte detection device and method related to a portable instrument suitable for point-of-care analyses. In some embodiments, a portable instrument may include a disposable cartridge, an optical detector, a sample collection device and/or sample reservoir, reagent delivery systems, fluid delivery systems, one or more channels, and/or waste reservoirs. Use of a portable instrument may reduce the hazard to an operator by reducing an operator's contact with a sample for analysis. The device is capable of obtaining diagnostic information using cellular- and/or particle-based analyses and may be used in conjunction with membrane- and/or particle-based analysis cartridges. Analytes, including proteins and cells and/or microbes may be detected using the membrane and/or particle based analysis system.

U.S. Pat. No. 6,498,862 to Pierson dated Apr. 10, 2012, is directed to biofilm formation that is monitored by real-time continuous measurement. Images are formed of sessile cells on a surface and planktonic cells adjacent the surface. The attachment of cells to the surface is measured and quantitated, and sessile and planktonic cells are distinguished using image processing techniques. Single cells as well as colonies are monitored on or adjacent a variety of substrates. Flowing streams may be monitored. The effects of biocides on biofilms commonly isolated from recyclable water systems are measured.

The prior art described above teaches a viable specifically labeled antigen detection and detection device for detecting method, a particle analysis in an acoustic cytometer, a centrifugal force-based system for detection/treatment of membrane-encased structures, a ballast water treatment plant having filter, disinfection, instrumentation and control unit, a system for causing relative motion, a ballast water treatment system and ballast water treatment method, a system and method for obtaining sensing results and/or data in response to object detection, a ballast water treatment system, flow based clinical analysis, integration of fluids and reagents into self-contained cartridges containing sensor elements, and evaluation of biofilms and the effects of biocides thereon, but does not teach a means for imparting at least inertial stimulation to organisms within a fluid flow for the purpose of determining whether organisms are living based on detected responsive movement and/or motion of the organisms.

A further example relating to water usage relates to water movement through pumping facilities. Whether for potable applications, irrigation, cooling, or the like, at some point there is inherently involved an "intake" where the source water is acquired or taken into a system such as a pumping facility. Unfortunately, often at such intakes adverse environmental impacts may result, as by pulling large numbers of fish, shellfish, and/or their eggs and other such marine life into the system along with the water. In response, many regulations have been passed, including or as mandated by Section 316(b) of the Clean Water Act of 1972, which requires the EPA to issue regulations on the design and operation of intake structures in order to minimize adverse impacts.

One exemplary ecosystem and water source is California's Sacramento Delta and the adjoining San Francisco Estuary. This sprawling freshwater system is fed by rainfall and snowmelt from the nearby Sierra Nevada Mountains and the Sacramento and San Joaquin River watersheds. Among numerous species, the water system is home to the Delta smelt (*Hypomesus transpacificus*), a small pelagic fish that was once abundant but has seen dramatic declines over the past several decades, prompting their protection under federal and state endangered species acts starting in 1992. The Delta smelt are particularly at risk in their larvae and juvenile stages, which often coincides with peak seasonal water flows. Due to concerns about entraining and killing the small Delta smelt and other fish such as juvenile Chinook salmon, when pumps at the Banks and Jones pumping facilities adjoining the Delta Clifton Court Forebay are operated, pursuant to the Endangered Species Act ("ESA") and a 2008 California Supreme Court order, promulgated and interpreted by the EPA and other authorities under the overarching requirement of Section 316b of the CWA, the pumps are then often shut down or throttled back even when water is in abundance, resulting in millions of acre-feet or billions of dollars' worth of desperately needed fresh water flowing out into the San Francisco Bay rather than south to water-scarce regions of Central and Southern California. Fundamentally, operation of the pumps is curtailed based on assumptions and "abundance of caution" rather than solid, empirical data regarding the populations of Delta smelt, Chinook salmon, and other fragile fish in the Clifton Court Forebay and the waterways feeding the pumping facilities at any particular time. As such, what is needed and has heretofore been unavailable is a means to accurately monitor the fish in such water systems, as by an automated system for counting and/or species identification.

Other more recent approaches aimed at addressing seasonal fresh water shortages include proposals regarding desalination of ocean water along coastal areas. Such desalination plants have large water intakes not unlike the inlets to the pumping facilities in the Sacramento Delta and around the world. Therefore, it is also desirable to account for marine life in the ocean and adjoining bays in the vicinity of any desalination or other water treatment plant, particularly at the intakes, to again identify and/or quantify the fish and other marine life present at any given time in the interest of understanding and preventing harm to such resident species of marine life.

By accurately assessing the presence of fish and other marine life, operation of any water treatment or pumping facility may be more optimally regulated, potentially in conjunction with other mitigating technologies such as means for screening or actually separating and/or capturing and relocating fish and other marine life away from any potential harm. Preferably, any such fish or other marine life are counted and/or identified substantially in real time on site as through an automated or semi-automated system through which water flow containing the marine life is passing. Such would be a vast improvement over off-line or manual approaches or sampling models from which total counts are extrapolated.

As a follow-on corollary to the foregoing particularly relating to means for screening or actually separating and/or capturing and relocating fish and other marine life, it should be appreciated that in other contexts it might be helpful to separate out and then exterminate nuisance, non-native or invasive species, such as Asian carp, as compared to separating out local/native and even endangered species and returning them to the water system where appropriate as in the exemplary Delta smelt context.

Aspects of the present invention fulfill these needs and teach certain benefits in construction and use which give rise to the exemplary advantages described below.

SUMMARY

Aspects of the present invention teach certain benefits in construction and use which give rise to the exemplary advantages described below.

The present invention solves the problems described above by providing an evaluation system for determining the number and/or identity (species) of organisms within a water flow and/or whether any such organism is living.

In at least one exemplary embodiment, the organism evaluation system is configured for analyzing microorganisms or other living organisms within a fluid flow, comprising a microorganism stimulation section comprising a means for inducing a motive response in a living microorganism capable of such within the fluid flow passing through the microorganism stimulation section, and a viewing section in fluid communication with the microorganism stimulation section, the viewing section comprising a body having formed therein a body cavity defining a viewing port visible through a cavity first opening formed in the body so as to be in communication with the body cavity, the viewing section further comprising an optical system mounted relative to the body for viewing the fluid flow within the viewing port through the cavity first opening, whereby image data relating to the fluid flow and microorganisms therein is acquired via the optical system for analysis.

In at least a further exemplary embodiment, the organism evaluation system is configured for counting and/or identifying fish or other marine life or organisms within a water flow, the system comprising a sorting section for separating particular fish or other marine life or organisms from other fish and organisms within a flow, a velocity control section for isolating a flow and controlling key water parameters in what is effectively a micro environment contained within a larger macro environment, a shepherding section so as to acquire the sampled fish or other organisms from the isolated flow, and a viewing section for obtaining image data associated with the sampled fish or other organisms.

A primary objective inherent in the above described system and method of use is to provide advantages not taught by the prior art.

Another objective is to provide such a system wherein a flow normalizing section is in fluid communication between the microorganism stimulation section and the viewing section, the flow normalizing section comprising an inlet chute having a tapered inlet chute inner bore.

Another objective is to provide such a system wherein a flow normalizing section is in fluid communication between the shepherding section and the viewing section.

Yet another objective is to provide such a system wherein a sample pre-conditioning section is upstream of and in fluid communication with the microorganism stimulation section.

Yet another objective is to provide such a system wherein any such exemplary components, sub-systems, or sections may be combined in any appropriate manner in order to facilitate one or more of determining the number of organisms within a water flow, determining the identity or species of organisms within a water flow, and determining whether any such organism is living.

Other objects, features, and advantages of aspects of the present invention will become more apparent from the following detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

Figure 1:
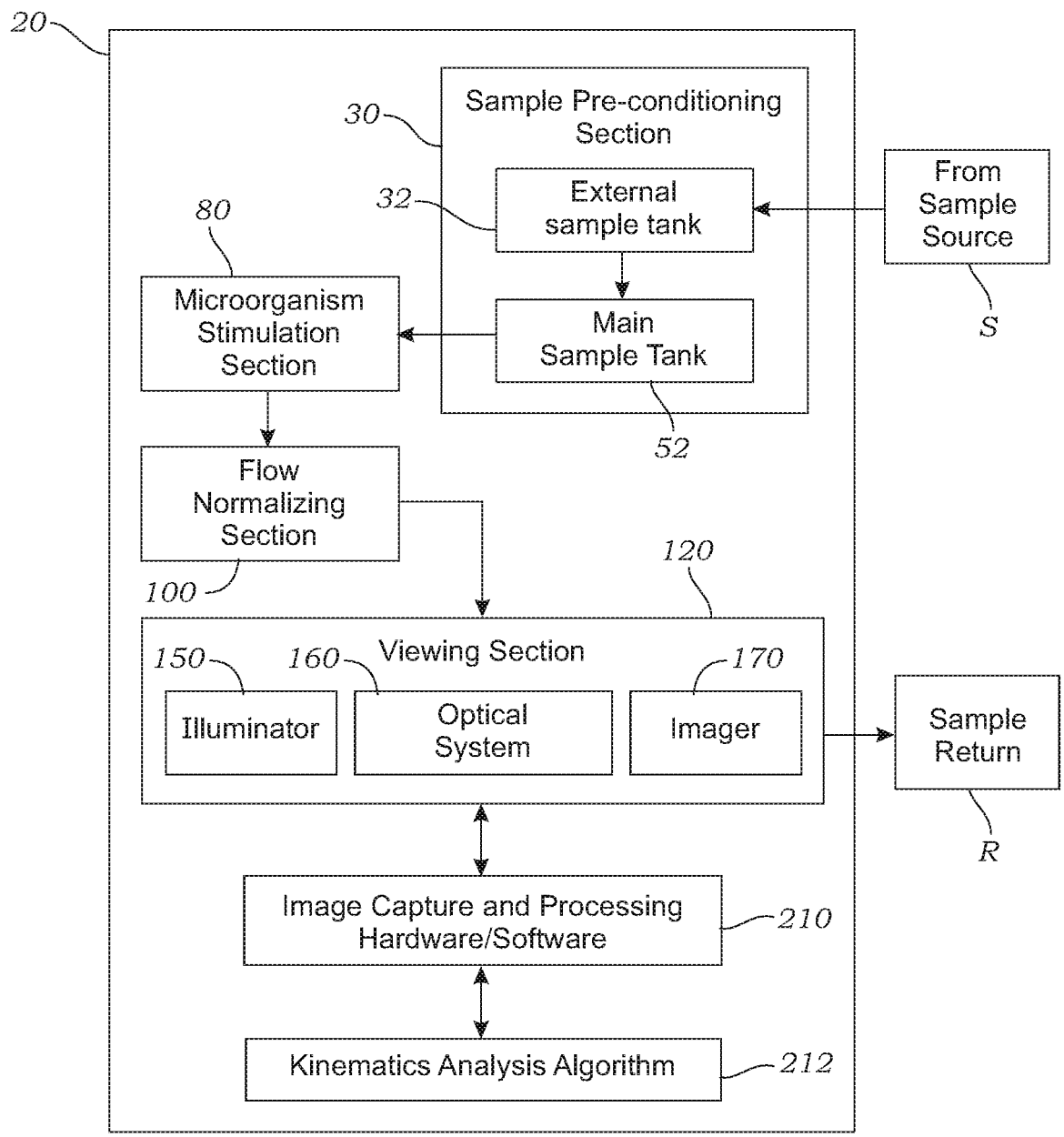
FIG. 1 is a block diagram illustrating an exemplary organism evaluation system, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments. More generally, those skilled in the art will appreciate that the drawings are schematic in nature and are not to be taken literally or to scale in terms of material configurations, sizes, thicknesses, and other attributes of an apparatus according to aspects of the present invention and its components or features unless specifically set forth herein.

DETAILED DESCRIPTION

The following discussion provides many exemplary embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

While the inventive subject matter is susceptible of various modifications and alternative embodiments, certain illustrated embodiments thereof are shown in the drawings and will be described below in detail. It should be understood, however, that there is no intention to limit the invention to any specific form disclosed, but on the contrary, the inventive subject matter is to cover all modifications, alternative embodiments, and equivalents falling within the scope of the claims.

In general, according to aspects of the present invention, batch or continuous real time monitoring is deployable within ballast water treatment systems and the like and provides further advantages over prior art test systems and approaches, the support of continuous real time monitoring being particularly advantageous for several applications. The subject invention, though again in the context of BWTS compliance testing, may be practiced in a wide array of contexts and so is not limited to the exemplary BWTS context (for example, fish monitoring in bays and estuaries and related waterways as described further below, monitoring invasive species migration in fresh and salt water bodies, bioterrorism, etc.). Thus, while "water" is discussed throughout as the sampled fluid, it is to be understood that the invention is not so limited and other fluids may be sampled as well, again depending on the context.

While various contexts are illustrated, including both ballast water exchange and related microorganism evaluation and fish monitoring in forebays, oceans, etc. and related waterways adjacent to pumping facility intakes and the like, it will be appreciated that a virtually infinite variety of contexts and related species, microorganisms, fish, or other marine life may be applicable to or the subject of evaluation systems according to aspects of the present invention, such that any illustrated contexts and related organisms being evaluated are to be understood as merely exemplary and non-limiting; accordingly, use of the terms "microorganism" and "fish" are to be understood as illustrative, with all such living organisms of any size being collectively referred to herein as "an organism" or "organisms" and encompassed by the use of such terminology—that is, all such terms (organism, microorganism, and fish) are used interchangeably throughout, except where express indication or context dictates otherwise, it being appreciated that any commercial application and related organism(s) to be evaluated may vary in size and the related system be scaled up or down or otherwise modified accordingly within the spirit and scope of the invention, such that systems as disclosed in FIGS. 1-20 generally described in the microorganism context may be adapted to be employed in connection with other marine life or life forms of any and particularly relatively larger size, and conversely systems as disclosed in FIGS. 21-31 generally described in the fish context may be adapted to be employed in connection with other marine life or life forms of any and particularly relatively smaller size. As appropriate, any such systems, as being adapted to a particular context or otherwise, may be not only resized (scaled up and/or down, in whole or in part) but reconfigured as by employing various combinations of features, components, sub-systems, or sections according to aspects of the present invention without departing from its spirit and scope, such that, once more, it will be appreciated that a virtually infinite variety of configurations and arrangements of an organism evaluation system according to aspects of the present invention are possible beyond those shown and described. Relatedly, those skilled in the art will appreciate that any such organisms, including but not limited to the exemplary fish and microorganisms, again of whatever size, are effectively living control systems that respond to stimuli, a trait taken advantage of according to or in certain aspects and embodiments of the present invention.

As an overview, and with reference to FIG. 1, the exemplary organism evaluation system 20 has four main hardware components or sections, which are discussed in turn below: (1) a sample pre-conditioning section 30; (2) a microorganism stimulation section 80; (3) a flow normalizing section 100; and (4) a viewing section 120. There are related tanks, tubes, flow controls and other aspects that facilitate the collection and processing of the water sample, which may be necessary in particular contexts but are nevertheless ancillary components that can be substituted for by other equivalent structure (e.g. pumps, etc.), and so are not the focus of the present invention. It will be appreciated by those skilled in the art that the exact configuration of the system and its four main sections may take a number of forms to suit particular applications without departing from the spirit and scope of the present invention. Accordingly, it will be further appreciated that the configurations of the system shown and described are exemplary and that the invention is not so limited. Moreover, once again, while "water" is discussed throughout as the sampled fluid, it is to be understood that the invention is not so limited and other fluids may be sampled as well, again depending on the context. Relatedly, it is assumed for these purposes that whatever fluid is sampled contains microorganisms, some living and some dead, such as Zooplankton in the size range of approximately 10 to 50 microns, for example. It is further noted as a threshold matter that the present focus of the subject invention is in determining whether certain microorganisms are living, as again evidenced by a motive response of some kind, and not necessarily whether such an organism is "viable" in the sense that it is capable of living for an extended period, reproducing, etc., it being understood that all viable organisms are living but that not necessarily all living organisms are viable, though it will be appreciated that inherently the present invention will identify viable organisms as it does living ones. It will be appreciated based on the present disclosure that any such system 20 may instead or in addition monitor or record the number and/or size or identification of any such organisms passing therethrough. When a "fluid flow" is referenced herein, such may refer to a main body of water or flow or an off-line or sub-flow as through an evaluation system 20 according to aspects of the present invention, and such fluid flow may further exist within various components or sections of such a system 20 to varying degrees; that is, due to diversions and the like, the "fluid flow" that is present at any given time within the system 20 or a sub-system or section thereof may be all or only a portion of the initial fluid flow from which any organisms are to be sampled or evaluated. Relatedly, such fluid flow and ensuing evaluation in and by any organism evaluation system according to aspects of the present invention may be substantially continuous and/or "real time" or may be an off-line sampling of the main fluid flow, or any combination thereof.

With continued reference to FIG. 1, the block diagram shows the exemplary embodiment of the organism evaluation system 20 according to aspects of the present invention as generally comprising a sample pre-conditioning section 30 configured in fluid communication with a sample source S so as to receive and process a fluid sample and pass such sample along to a microorganism stimulation section 80 configured to agitate, excite, or otherwise stimulate one or more senses of any living microorganisms in the fluid sample. The sample pre-conditioning section 30 is shown as comprising an external sample tank 32 that receives the fluid flow from the sample source S and then passes such fluid on to a main sample tank 52 before then flowing to the microorganism stimulation section 80, though it will be appreciated that a variety of means for acquiring and passing along a fluid sample, static or dynamic and now known or later developed, may be employed without departing from the spirit and scope of the present invention, such that the two tanks in series are to be understood as merely exemplary of aspects of the invention. A flow normalizing section 100 is downstream of and in fluid communication with the microorganism stimulation section 80 for the purpose of slowing and/or rendering more laminar the fluid flow after it leaves the stimulation section 80, which may involve agitation of not just the organisms but the fluid itself. Downstream of and in fluid communication with the flow normalizing section 100 is a viewing section 120 configured for passing the flow therethrough and obtaining image data thereof. More particularly, in the exemplary embodiment, the viewing section 120 comprises an illuminator 150 for providing lighting to the viewing section 120, an optical system 160 for actually acquiring image data as would a camera or camera-like device, and an imager 170 for processing or manipulating the image data from the optical system 160. It will be appreciated that throughout when a "camera" is discussed is being the "optical system 160" or equipment that any such device, whether "off the shelf" or proprietary, may further include imaging capability, that is, the ability to capture and manipulate image data with sufficient frame rate and resolution, such that in fact the "optical system 160 and the imager 170 may be a single device in the form of a "camera" or the like. From the viewing section 120 the fluid flow proceeds to a sample return R. Further regarding the organism evaluation system 20, and the viewing section 120 specifically, there is shown a separate image capture and processing device 210 (hardware and software) in communication with the viewing section 120, which device 210 is configured for taking the image data from the imager 170 and further processing the data for analysis. The image capture and processing device 210 may be any computer or processor or computing or processing device now known or later developed and may be wired or wirelessly connected to the viewing section 120, or may be incorporated into the viewing section 120, and the imager 170 specifically, again for the purpose of acquiring and processing the image data obtained by the optical system 160. Moreover, the entire viewing section 120 may be a proprietary and/or unitary device or may be comprised of one or more "off the shelf" components operably connected and configured according to aspects of the present invention, such as, for example, employing a digital camera as the optical system 160 and outputting image data from such camera using its high-speed interface such as USB 2, HDMI, or other appropriate interface to a computer configured to operate as the imager 170 and image capture and processing device 210, or the viewing section 120 may be some combination thereof. Such computer may further have installed and run the kinematics analysis algorithm 212, or such algorithm 212 may be configured to operate on a separate computer or computing device. Ultimately, those skilled in the art will appreciate that the components of the viewing section 120, namely, the illuminator 150, the optical system 160, and the imager 170, and the related image capture and processing device 210 and kinematics analysis algorithm 212 may be configured in a variety of ways in one more devices without departing from the spirit and scope of the present invention, such that it is to be understood that the particular arrangement shown in FIG. 1 and elsewhere herein is merely illustrative of features and aspects of the present invention and non-limiting. Specifically, it will be appreciated that the image capture and processing device 210 and kinematics analysis algorithm 212 may be physically configured within the organism evaluation system 20 or not but are nevertheless components of the overall system 20 as represented by the block diagram of FIG. 1. Furthermore, any of the components of the system 20 may or may not be integral or packaged in a unitary way without departing from the spirit and scope of the invention.

Figure 2:
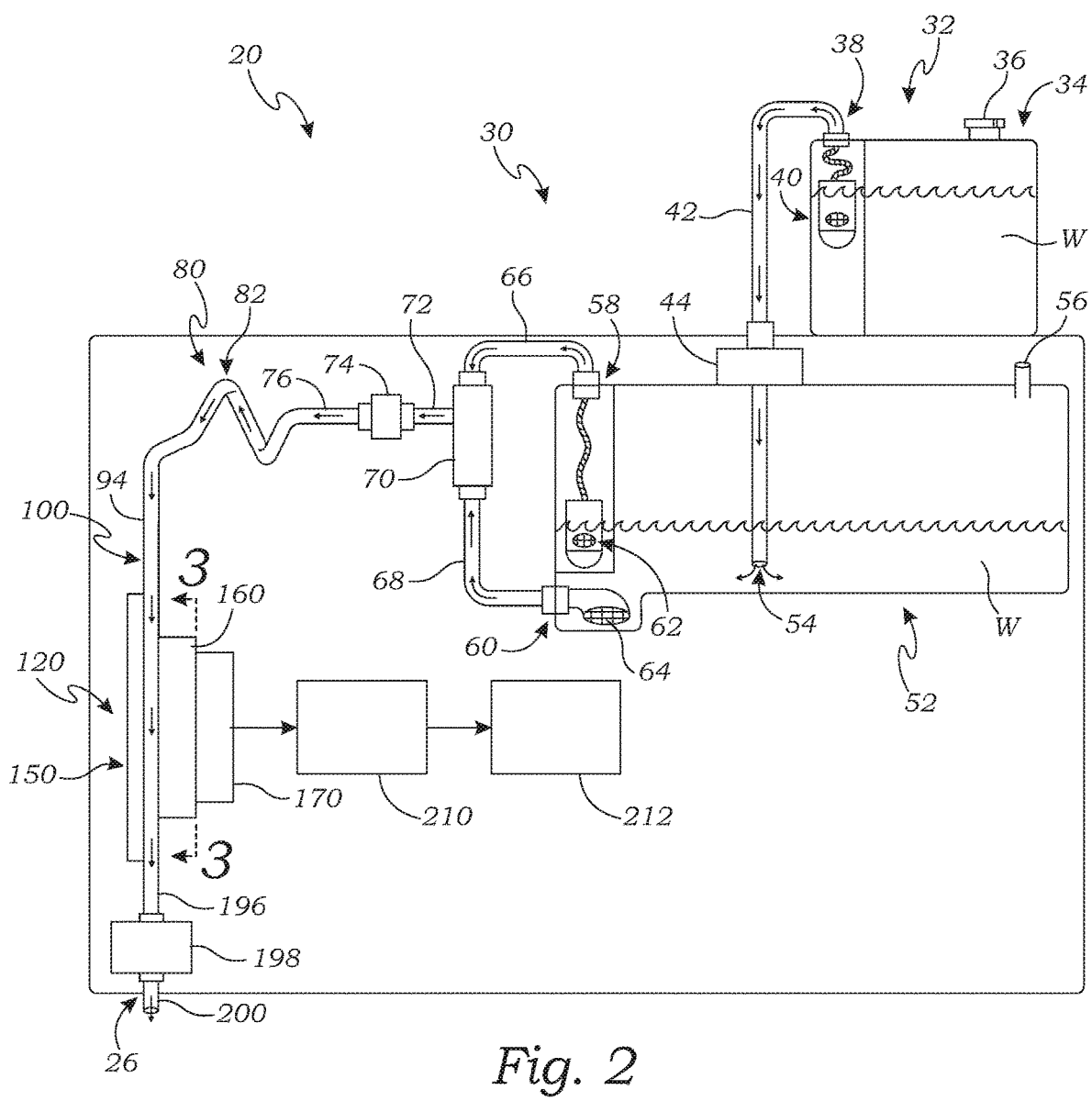
FIG. 2 is a schematic representation thereof, in accordance with at least one embodiment.

Turning now to FIG. 2, there is shown a schematic view, not to scale, of an exemplary embodiment of the organism evaluation system 20 according to aspects of the present invention as shown in the block diagram of FIG. 1. Going in sequence as a water sample would be processed through the system 20, and thus starting upstream of the stimulation section 80, there is again first the sample pre-conditioning section 30. This pre-conditioning section 30 can be implemented in different ways. For example, in real time continuous sampling applications the pre-conditioning function can be accomplished by utilizing the differing inertial characteristics of the particulates contained in the sampled fluid. Or, isokinetic or other techniques for sampling from a continuous flow now known or later developed may be substituted for the one or more tanks 32, 52 of the exemplary embodiment without departing from the spirit and scope of the present invention. Back to the discrete or static sample application, a removable external sample tank 32 is provided as a container into which a test sample is to be initially collected. While in FIG. 2 the initial external sample tank 32 is shown as being physically outside of the system, it is nevertheless part of the system 20, or the sample pre-conditioning section 30 specifically, as once again shown in the block diagram of FIG. 1. Such an external sample tank 32 may comprise a cap and vent 36 removably positioned in an inlet 34 and an external sample tank buoyant intake 40 configured with a filtered opening and a turbidity detection device (not shown) through which the sample fluid passes on its way to an outlet 38 of the external sample tank 32. By employing a buoyant sample intake 40, the intake is configured to resist dropping low enough in the tank 32 to pull in mud and other particulates that have settled to the bottom of the tank 32. The external sample tank 32 is thus configured as an initial sample fluid holding tank in which the sample is effectively pre-conditioned, particularly as to turbidity, before passing onto other portions of the organism evaluation system 20. Thus, the external sample tank 32 being removable facilitates the disposal of unwanted particulates such as mud deposits from turbid water and other inorganic or "dead" materials. A tank tubing 42 connects the outlet 38 of the external sample tank 32 to an inlet 54 of a main sample tank 52 installed within the system 20, the tubing 42 passing through a first opening 24 in the box or case or other such enclosure 22 in which the overall organism evaluation system 20 is installed and being coupled to the main sample tank 52 through a quick disconnect coupling 44 and a flow control 46 that cooperates with other aspects of the system's control sub-system in moving the fluid therethrough. Within the main sample tank 52, a down tube in the exemplary embodiment defining the inlet 54 is in fluid communication with the tubing 42 so as to effectively deliver the fluid from the external sample tank 32 to the bottom portion of the main sample tank 52, again for reasons related to turbidity and, more generally, consistent sample density during the sampling event. As with the external sample tank 32, the main sample tank 52 is also configured with a vent 56 and with a main sample tank buoyant intake 62 configured with a filtered opening through which the sample fluid passes on its way to an upper main sample tank first outlet 58. The main sample tank 52 is further configured with a lower main sample tank second outlet 60 having a main sample tank filtered intake 64 to allow fluid to pass therethrough as a means of essentially regulating the outflow, in cooperation with the proportional flow valve 70 discussed below, such that the higher the column height of fluid in the main sample tank 52, the greater the tendency of fluid to pass out of the lower outlet 60, and vice versa. In other words, during the earlier period of the sampling event when the sample is at the greatest level in the tank 52, relatively less sample will flow from the buoyant intake 62 and relatively more from the lower fixed intake 64, and during the later period of the sampling event when the sample is at the lowest level in the tank 52, relatively more sample will flow through the buoyant intake 62 and relatively less sample will flow through the lower fixed intake 64. Moreover, since it is known that indicator organisms such as Zooplankton within a water sample will generally be at relatively greater concentrations at or near the surface and relatively lower concentrations at or near the bottom of a body of water, by employing two outlets—one that floats and rises and falls with the water level in the tank and one that is fixed at the bottom or substantially lowest point of the tank—once more the objective of providing greater consistency in the density of the Zooplankton or other organism within the sample is achieved. Furthermore, an upper outlet tubing 66 in fluid communication with the upper outlet 58 and a lower outlet tubing 68 in fluid communication with the lower outlet 60 both are in fluid communication with a proportional flow valve 70 that further cooperates with the upper and lower outlets 58, 60 to regulate and normalize the flow of fluid from the main sample tank 52, the proportional flow valve 70 also mixing the fluid from the twin intakes 62, 64, again in the interest of yielding a relatively consistent sample density during the sampling event from the main sample tank 52. Downstream of the pre-conditioning section 30 there is operably positioned a second flow control 74 in fluid communication with the proportional flow valve 70 view tubing 72 that once again cooperates with other aspects of the system's control sub-system in moving the fluid therethrough and on to the microorganism stimulation section 80 and the rest of the organism evaluation system 20, as described further below. The flow control sub-system or any other devices such as pumps would effectively operate on a continuity principle aimed at providing a relatively clean, smooth, and consistent flow of fluid being sampled. Those skilled in the art will again appreciate that while an exemplary multiple-sample tank set-up is shown and described in connection with the exemplary organism evaluation system 20, each tank having respective inlets, outlets, vents, filters, and buoyant sample intakes and the fluid moved therethrough in cooperation with or under the control of one or more flow controls, the invention is not so limited, for example, as indicated, such sampling may instead involve a continuous real time monitoring scheme. Thus, any such sample collection, holding, and delivery hardware and related controls now known or later developed may be practiced in conjunction with the present invention without departing from its spirit and scope, such that the disclosed tank set-up is to be expressly understood as illustrative and non-limiting. More generally, the disclosed tank sub-system or other equivalent structure facilitates improved system performance through: (i) separation of live organisms from dead or inorganic material; (ii) removal of a significant amount of non-live material within the external sample tank 32 before entering the main sample tank 52 and rest of the organism evaluation system 20; (iii) lowering maintenance requirements due to reduced inorganic ingestion; (iv) mitigating the consequence of a relatively turbid water sample; and/or (v) providing a relatively less cluttered sample due again to the sample's relatively fewer dead or inorganic matter.

Regarding the microorganism stimulation section 80 within the organism evaluation system 20 that follows the tank sub-system or pre-conditioning section 30 above-described, and as further background, the general idea is that the organisms in the water being sampled/tested will physically respond to stimuli if they are alive and not if they are dead. This is, in fact, how it is done in the lab under a microscope, with the technician "poking" the organisms to see if movement can be observed. It is thus important to provide adequate stimulation of the organisms in a way that will cause a clearly detectable reaction by a living organism; an organism that is alive will respond to the stimulation from this section 80 by generating its own movement, which self-generated movement is then isolated from the movement of the fluid sample in the flow normalizing section 100 and then detected in the viewing section 120, more about which is said below. It will also thus be further appreciated that the pre-sampling removal of dead or inorganic matter through settling or otherwise within the pre-conditioning section 30 again thereby contributes to the effectiveness of the downstream system, where the focus is to be on stimulating and detecting live microorganisms capable of motive response. But those skilled in the art will also appreciate that in some contexts the sample pre-conditioning section 30 will simply not be required, such as situations wherein the water sample has low turbidity or wherein the means of acquiring the sample, which of itself could be seen as another type of sample pre-conditioning device, is adequate to allow for meaningful downstream evaluation of organisms within the sample.

With continued reference to FIG. 2, then, in the first exemplary embodiment, an inertial disorientation section ("agitator") or microorganism stimulation section 80 is provided downstream of the sample pre-conditioning section 30 in order to subject the microorganisms to motive stimulation (agitator #1). Here, the stimulation section 80 is configured as a helix tube or disorientation spiral 82 having most likely more than one loop, though it will be appreciated that additional loops of various sizes and configurations can be added as required, any such geometries being dictated, at least in part, by the input determined for proper inertial stimulation of the microorganism. The theory is that the helix geometry of the disorientation spiral 82 will induce the fluid in the tube to rotate around the tubular axis, which will stimulate (agitate) the inertial sensing mechanisms found within the microorganisms, more about which is said below in connection with FIGS. 15 and 16.

Still in connection with FIG. 2, after the sample water leaves the microorganism stimulation section 80 wherein the flow is twisted and inertial effects are induced, it is then desirable to provide a flow normalizing section 100, or a section of the system conduit wherein the sample fluid has sufficient distance over which it is able to become relatively laminar, or wherein the radial or spiral flow is dampened out on its way to the viewing section 120. However, it will be appreciated that such dampening or relatively laminar flow may be achieved simply in the exit from the disorientation spiral 82 depending on its length and the diameter and surface features (smoothness or roughness) of the spiral bore 92 (FIG. 8) and/or in the viewing section body inlet 124 or viewing port 144 itself (FIGS. 3 and 4), such that in some embodiments the flow normalizing section 100 may not be employed. It will also be appreciated that such a normalizing section 100 may not be required at all or to the same extent in embodiments of the system wherein PSD direct or indirect hydraulic stimulation is employed, for example, such as in the alternative embodiments of FIGS. 17 and 18. Again, the primary purpose of the flow normalizing section 100 when it is employed is to effectively isolate self-generated movement of a microorganism from the movement of the fluid sample.

In this way, once the fluid flow is returned to substantially "straight-line," any continued movement of a microorganism, as detected in the viewing section 120, would be deemed self-generated motion, as opposed to flow-generated motion. Thus, the normalizing inlet chute 102 (FIGS. 3, 5-7, 9 and 10) between the stimulation section 80 and the viewing section 120 of the organism evaluation system 20 is shown as being a relatively long, substantially linear chute that supports normalizing microorganism motion by providing a travel time that is less than the "disorientation response decay time" of the microorganisms, or the time from the reaction to the stimulation event beyond which an organism's induced response would be expected to cease, which for Zooplankton and other such organisms is thought to be on the order of 5-10 seconds. In other words, the normalizing chute 102 as in the exemplary embodiment is to be long enough to allow the flow to "straighten out" while not being so long that at the system's characteristic flow rate the disorientation response decay time for the microorganisms is exceeded by the time the fluid sample reaches the viewing section 120 from the stimulation section 80, such that self-generated movement of some kind would potentially not be seen in the viewing section 120 even for living or viable organisms. This "sizing" of the flow normalization section 100 and the inlet chute 102 particularly may be accomplished by utilization of CFD ("computational fluid dynamics") analysis to determine the length of the chute 102 required to normalize the motion of the microorganism before the viewing section 120, with one such exemplary inlet chute 102 geometry being shown and described below in connection with FIGS. 5-7, 9 and 10, though it will be appreciated by those skilled in the art that a number of other geometric variations and methods of their determination are possible depending on a variety of factors, again including the microorganism type and the fluid type. It will be additionally appreciated, as discussed further below, that the length of the normalizing chute 102, in the case of a substantially vertical arrangement of the flow normalizing section 100 as depicted schematically in FIG. 2, is the leading contributor to the overall column height of water within the system 20, or the change in height within the system 20 from the water level within the main sample tank 52 to the overall system exit or discharge point of sample return tube 200, which column height will not only have an influence on system flow rate but also create a pressure variance to which the microorganisms can respond as well.

Figures 3, 4:
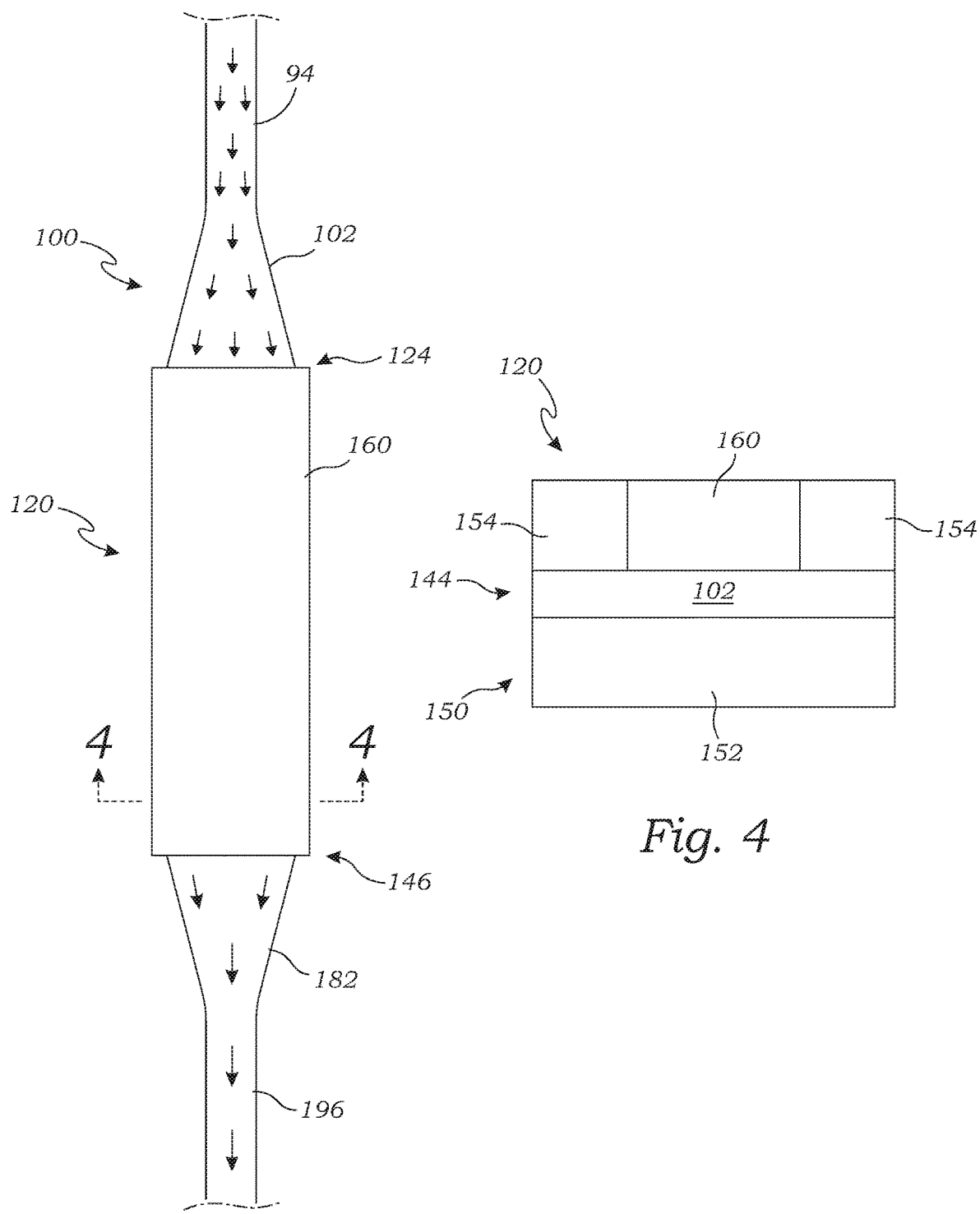
FIG. 3 is an enlarged partial schematic representation thereof taken along line 3-3 of FIG. 2, in accordance with at least one embodiment.
FIG. 4 is an enlarged partial schematic representation thereof taken along line 4-4 of FIG. 3, in accordance with at least one embodiment.

Turning next to the viewing section 120 shown schematically in FIG. 2, the fourth major hardware component or section of the organism evaluation system 20 according to aspects of the present invention, there are a number of features involving the physical, geometrical set-up alone that are specifically designed to accomplish the necessary data acquisition and are addressed in turn herein. The basic idea is that once the fluid sample has been pre-conditioned in the sample pre-conditioning section 30, the microorganisms within the sample have been stimulated in the stimulation section 80, and the flow within the system 20 regulated in the flow normalizing section 100, in the viewing section 120 visual data on the microorganisms is then obtained to support kinematics analysis and thereby determine whether any of the organisms are alive. First, as the flow enters the inlet chute 102 as schematically represented in FIG. 3, it basically flattens out and slows down through an expansion which causes a deceleration (negative acceleration or "−a"). The profile or cross-sectional area of the deceleration chute 102 is such to transition from the circular cross-section of the disorientation spiral 82 of the microorganism stimulation section 80 to a relatively larger rectangular cross-section of the viewing section 120, more about which is said below. The deceleration chute thus serves to reduce and normalize microorganism velocity through velocity change while not corrupting the self-induced relative motion of any organisms that are living. In fact, such deceleration or change in flow velocity is effectively another stimulus (agitator #2) to a living microorganism's sensory perception that would tend to induce further self-movement just before the organism enters the viewing section 120, even while the flow itself is slowing and further normalizing. Those skilled in the art will appreciate that such normalization is also desired, in part, in order to account for the relative difference in velocity across the profile as caused by the pipe walls, the flow and thus microorganism velocity at the center of any pipe being greater than at the walls where shear forces act on the fluid. The desirability of the flow or organism velocity slowing and normalizing prior to entering the actual viewing section 120 will be further appreciated upon consideration of the operation of the viewing section 120 itself.

In general, and with reference to FIGS. 2 and 3 and now FIG. 4, the viewing section 120 comprises a substantially flat or rectangular profile flow path through which optical equipment such as a digital camera "looks." It is contemplated that twenty (20) or more frames for each organism are desirable as a data set in order to draw conclusions about the organism's relative movement. It will thus be appreciated that obtaining the desired number of frames is essentially a function of the flow rate through the viewing section 120 and the optical equipment's imaging capabilities (optical system 160 and imager 170). Put another way, there are two primary aspects regarding the viewing section 120: (i) depth of field; and (ii) transit time—that is, through what cross-section can the optical equipment focus at a time, and how long is the segment of interest of the fluid within the viewer in order to get the snapshots for the data set. Accordingly, regarding the depth of field, the viewing section 120 preferably flattens out into a substantially rectangular profile defining the viewing port 144 of the viewing section 120 that is somewhat commensurate with the view angle or field of view of the optical system 160 (the camera or other optical sensor/equipment being used) and that has a depth that is within the focal length range of the optical system 160. Assuming currently available imaging components (lens field of view and focal lengths, resolution (on the order of twenty-four (24) megapixels), and full pixel array frame-rate), the aspects of the system of the present invention that dictate the function and performance of the viewing section 120 are primarily geometrical. For example, a camera capable of shooting at least ten (10) frames per second ("fps") at a processed "resolution" or image quality of at least 2 megapixels ("mp"), or a processed "1080P high definition video" as presently known, would be adequate for purposes of the present invention. Clearly, as technology advances are made, even faster or higher resolution digital cameras may be employed, which may then allow for higher sampling or flow rates and/or a smaller viewing section 120. More particularly, any such digital camera employed in the present invention may be characterized by a CCD (charge-coupled device)- and/or CMOS (complementary metal-oxide semiconductor)-based sensor or imager, though again it will be appreciated that any such digital imaging technology now known or later developed may be employed according to aspects of the present invention. Irrespective of the digital imaging technology employed, maintenance of relatively laminar or normalized flow and a proper microorganism velocity profile through the viewing section 120 so as to not compromise the data collected (relative movement detected is due to microorganism self-generation, not flow turbulence) is a related and overarching consideration of the present invention. Further regarding the viewing section 120, also integral to the assembly as shown in FIGS. 2-4 is an LED-based illuminator 150 or light source substantially adjacent to the viewing section 120, possibly opposite the optical system 150 as shown in FIG. 2. Or, as shown in FIG. 4, the illuminator 150 may comprise a background illuminator 152 opposite the optical system 160 and one or more front illuminators 154 adjacent the optical system 150, with further variations on the illuminator 150 shown and described in connection with FIG. 5 and following, further below. Not only does the illuminator 150 facilitate image acquisition by the imager 170 of the microorganisms within the fluid sample, but it will be appreciated that this "step change" in light provides yet another stimulus to the organisms themselves within the viewing section 120 itself (agitator #3), it being known in the art that such organisms often have photoreceptors or other capability of detecting and responding to light. Finally, to complete the viewing section 120, in the exemplary embodiment, the flow therethrough exits by way of a contraction or funnel of sorts, shown and described as an acceleration ("+a") chute or outlet chute 182. Much like the deceleration chute 102 at the inlet to the viewing section 120, the acceleration chute 182 profile or cross-sectional area is such to transition from the rectangular cross-section of the viewing section 120 to the relatively smaller circular cross-section of now the exit tubing 196. Downstream of the viewing section and the exit tubing 196 there is positioned effectively a third flow control 198 (flow control 46 and pressure/flow control 74 being upstream), which again cooperates with other aspects of the system's control sub-system in moving the fluid therethrough. Moreover, as mentioned above, there is effectively a column height of water within the system 20, or a difference in height within the system 20 from the water level within the main sample tank 52 to the overall system exit or discharge point effectively at the point of the third flow control 198, which column height creates a pressure variance that is yet another stimulus to which the microorganisms can respond (agitator #4). In more detail, Zooplankton in particular tends to generate vertical motion to adjust its depth, which is why higher concentrations of such organisms are typically found at or near the surface of a fluid versus deeper within the fluid. Therefore, such pressure differential or variance as is a natural byproduct of the physical set-up and spatial orientation of the exemplary microorganism evaluation system 20 as shown and described herein, which again serves as another stimulus or means of exciting self-generated motion in the microorganisms. It will thus be appreciated that as the fluid flows downwardly through the system, and particularly the inlet chute 102 of the flow normalizing section 100 on its way to the viewing section 120, living organisms will have a tendency to attempt to "swim upstream" seeking areas of relatively lower pressure. It would be an object of the system 20 to then detect any and all such motion by living microorganisms passing through the viewing section 120 so as to thereby evaluate or document organism effective viability within the test sample. Accordingly, and to further facilitate the control and use of such a pressure differential within the system, in the exemplary embodiment, the third flow control 198 is also configured with a pressure change or "ΔP" control that can be used to manipulate pressure within the system 20, and indirectly flow rate. Once more, those skilled in the art will appreciate that such structure and functionality may be substituted for by other technology now known or later developed without departing from the spirit and scope of the invention. For example, while a substantially vertical arrangement of the system 20 is shown and described in connection with the exemplary schematic of FIG. 2, it will be appreciated that such a spatial orientation or relationship among the components is merely illustrative. More particularly, while a "column height of water" has been discussed as one means of employing a change in pressure as another "agitator" or stimulation to an organism's senses within a fluid sample flowing through the system 20, it will be appreciated that pressure differential can be created in a variety of other ways employing pumps, valves, restrictions, and the like, or in some contexts such a "ΔP" agitator may be nominal if employed at all. In the exemplary embodiment, then, a pre-viewing section region, or deceleration or inlet chute 102, is configured as an expansion within the flow path to decelerate or slow the flow and hence the microorganisms to the desired viewing speed before reaching the primary viewing section 120 adjacent the imaging system. The portion of the viewing section 120 immediately beneath the optical system 160 (camera) is then effectively flattened such that from the side it may even be thinner than the conduit while from above it is relatively wider. The result again in the exemplary embodiment is a cross-sectional area within the viewing section 120 that is greater than that of the flow conduit, again contributing to a slower, relatively laminar flow and "normalized" motion of the organisms as they flow through this area, while also providing a thinner vertical section or "depth of field" for the viewing section 120, enabling the imaging system (optical system 160 and imager 170) to acquire visual data on the microorganisms at any depth within the flow as they pass through the viewing section 120. The width and depth of the viewing section 120 are thus dictated in large measure by the physical and optical properties of the camera or other imaging equipment employed. Current technology supports a dwell time in the viewing section 120 of on the order of one to five (1-5) seconds. As indicated, the dwell time can be manipulated by adjusting the flow rate of the system for example. Using an approximately twenty-four frames-per-second (~24 fps) digital video imager 170, this will potentially generate approximately twenty-four to one-hundred twenty (24-120) data frames. Therefore, those skilled in the art will appreciate that the entire system and approach is scalable by using various or even multiple lenses to acquire the desired visual data across the viewing section 120. As the flow leaves the viewing section 120, a post-viewing section region, or acceleration or outlet chute 182, is configured as a contraction within the flow path to accelerate or speed up the flow back to the system velocity after the viewing section 120. Once again, it will be appreciated by those skilled in the art that a variety of other such components and configurations are possible beyond those shown and described without departing from the spirit and scope of the invention.

It is further noted in connection with FIG. 2 that in the exemplary embodiment the overall size of the organism evaluation system 20 is on the order of 3 ft×2 ft×1.5 ft, clearly a portable size, such that the system 20 may advantageously be employed on ships and in other field uses. A relatively small package is also conducive to real time continuously monitoring applications in that the system 20 can be installed in relatively tight packaging constraints. Portability and simplicity of design are further accomplished by the use of gravitational, fluid dynamics effects as a means of flowing or circulating the sample fluid through the system 20 from the sample location to the exit point. In turn, such geometrical aspects of the design along with the conduit sizes create conditions whereby a determinant of system velocity is the height between the sampling location and the fluid exhaust point of the system, more about which is said below. However, again, there also may be some form of pump augmentation to facilitate system function, as required. It will be appreciated by those skilled in the art that other sizes and packages and related configurations of the system 20 are possible without departing from the spirit and scope of the invention, such that the above discussion is to be understood as merely illustrative.

With continued reference to FIGS. 1 and 2, image capture and processing hardware/software 210 is connected to the imager 170 through a relatively high bandwidth connection, or a connection sufficient for the data acquisition capability of the digital imager 170 employed; software on the image capture and processing device 210 operates to facilitate such image acquisition and manipulation. The data thus captured is then acted on by kinematics analysis software 212, whether residing on or within the same hardware as the image capture and processing device 210 or a different hardware or computing device. Such software 212 is configured to identify each microorganism as imaged by the viewing section 120 and essentially plot that organism's movement in a frame-by-frame or like fashion so as to thus determine relative angular (directional) or rotational motion or physiological change indicative of life, more about which is said below in connection with FIGS. 15 and 16. For example, the kinematics analysis software 212 might look at derivatives such as rate of change in path or rotation as indicative of self-induced motion by the organism and/or rate of change in aspect ratio alone or relative to the path (angular motion) or the organism's orientation (rotational motion) as indicative of self-induced body movement of the organism. It is contemplated that since again the standard velocity profile of the fluid flow in the system 20 will generate different velocities between organisms traveling at the center of a pipe and those that are traveling near the walls of the pipe, both the viewing section 120 and the motion detection software 212 are to be configured to account for such.

Figure 5:
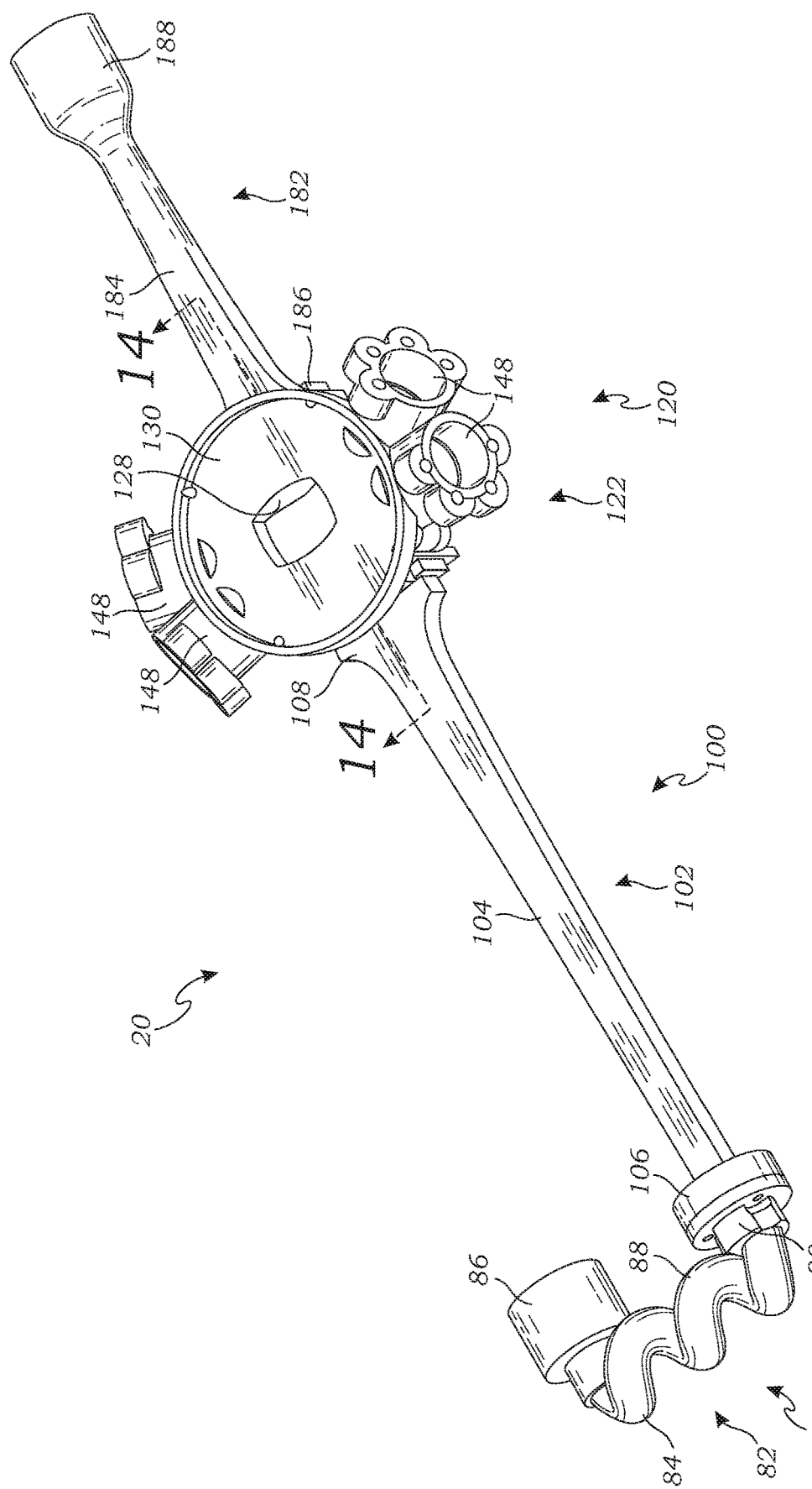
FIG. 5 is a partial perspective view thereof, in accordance with at least one embodiment.

Turning now to FIG. 5, there is shown a partial perspective view of an exemplary organism evaluation system 20 according to aspects of the present invention substantially consistent with the block diagram representation of FIG. 1 and the schematics of FIGS. 2-4. As a threshold matter, it is to be understood that the illustrated hardware components— here essentially the microorganism stimulation section 80, the flow normalizing section 100, and the viewing section 120, as well as the outlet chute 182 leading away from the viewing section 120—are merely representative or illustrative of aspects of the invention and are not limiting. In such views, it is noted that the pre-conditioning section 30 and other tubing, flow controls and the like are not shown for simplicity. Furthermore, the illuminator 150, the optical system 160, and the imager 170 are also not shown, though at least the illumination ports 148 four in the exemplary embodiment are shown wherein LEDs or the like may be installed so as to illuminate the interior cavity 126 of the viewing section 120, and the viewing port 144, specifically—are shown as being integral with the viewing section body 122. Regarding the optical system 160 and the imager 170, as explained above, these may be separate or integral components and "off the shelf" or proprietary, but in the exemplary embodiment a camera (not shown) is contemplated wherein the lens would mount or be removably installed directly to or on the optical system mount 130 of the viewing section body 122 such that the lens "looks" substantially straight into the cavity first opening 128 shown as intersecting the optical system mount 130 and, as best seen in the cross-sectional view of FIG. 14, communicating with the body cavity 126. Again, numerous other hardware components and configurations (geometry, means of assembly, etc.) are possible without departing from the spirit and scope of the present invention.

Figure 8:
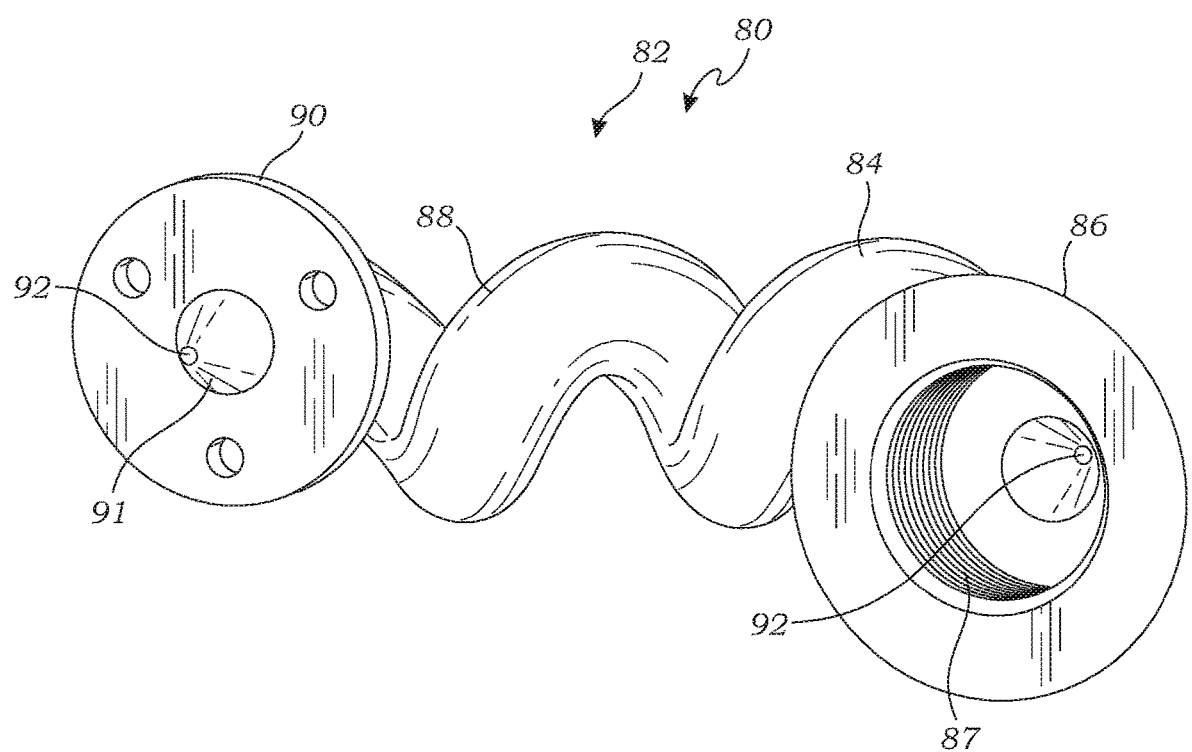
FIG. 8 is an enlarged partial perspective view thereof, in accordance with at least one embodiment.

With continued reference to FIG. 5, the microorganism stimulation section 80 is shown in the exemplary hardware embodiment as comprising a disorientation spiral 82 or helical tubular member. The disorientation spiral 82 is itself comprised of two turns—a first loop 84 and a second loop 88, each substantially comprising one revolution or a twist of three hundred sixty degrees (360°), though once again those skilled in the art will appreciate that any number and configurations of loops are possible within the scope of the invention, so long as sufficient rotation, twisting, or tumbling of the flow is provided so as to stimulate or excite the inertial sensing mechanisms of any living microorganisms within the sample flowing through the stimulation section 80. The first loop 84 is shown as having a proximal first loop coupling 86, which is configured for fluid connection to tubing 76 upstream of the stimulation section 80 through which the sample is delivered from the pre-conditioning section 30 (FIGS. 1 and 2). As best seen in FIG. 8, the first loop coupling 86 may be formed having an internally threaded bore 87 for threadably engaging an external thread on a mating coupling (not shown) formed on the end of the tubing 76, though it will be appreciated once more than any such coupling or removable engagement means now known or later developed may be employed. Similarly, the second loop 84 is formed having a distal second loop coupling 90 configured for fluid connection to the flow normalizing section 100 and specifically to an inlet chute first coupling 106. Here, as shown in FIG. 8, the second loop coupling 90 is formed as a conical fitting 91 configured to engage a conical bore 107 (FIG. 9) formed within the inlet chute first coupling 106 so as to open outwardly. As can also be seen in FIG. 8, there is formed axially or lengthwise along the entire disorientation spiral 82 a spiral inner bore 92 through which the sample flows. In the exemplary embodiment, the wall thickness of the disorientation spiral 82 (the first and second loops 84, 88) is approximately 3 mm and the inside diameter of the spiral bore 92 is approximately 1.2 mm, more about which will be said below in connection with the sizes of the other components of the exemplary system 20 and the operation thereof.

Figure 6:
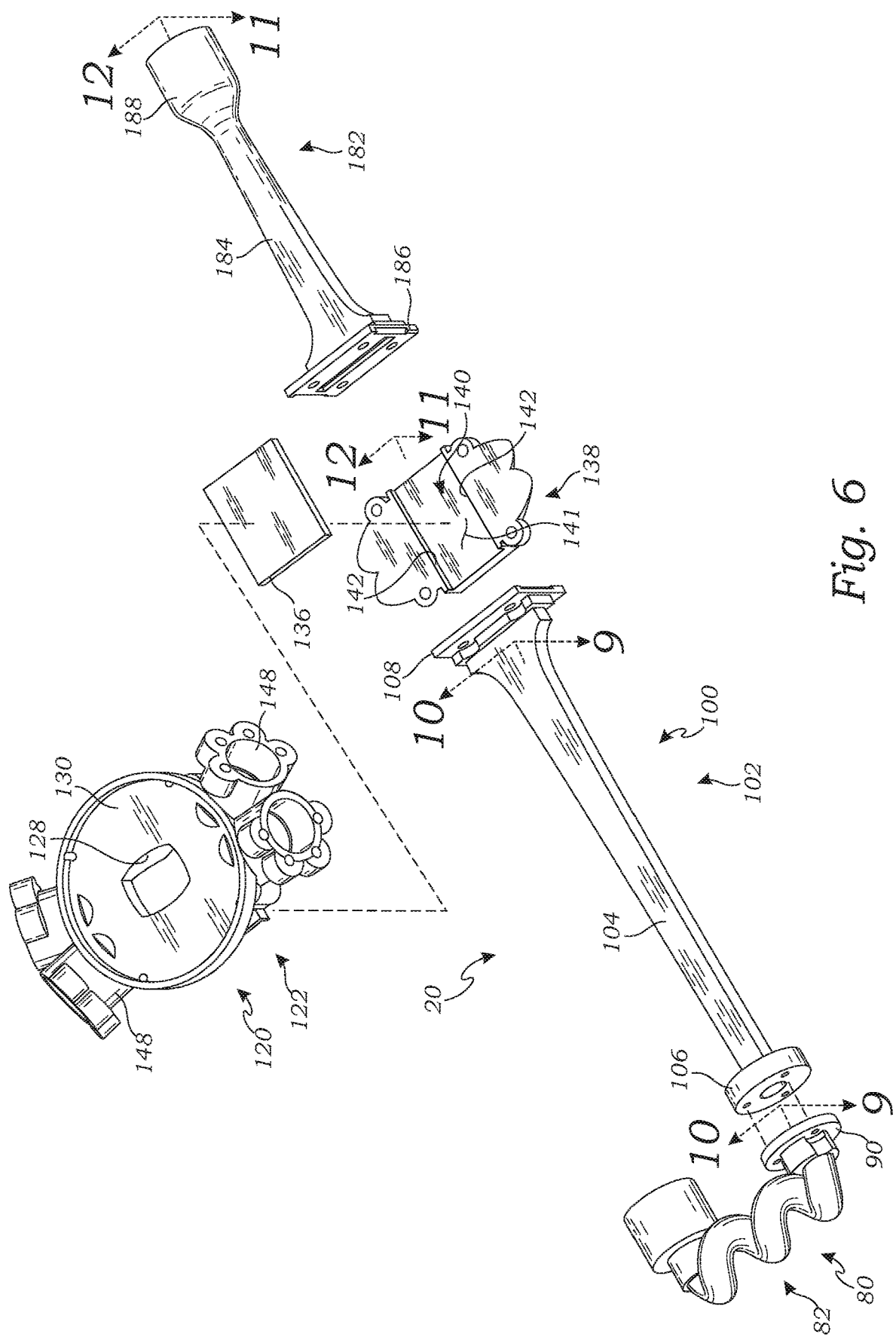
FIG. 6 is an exploded perspective view thereof, in accordance with at least one embodiment.
Figure 7:
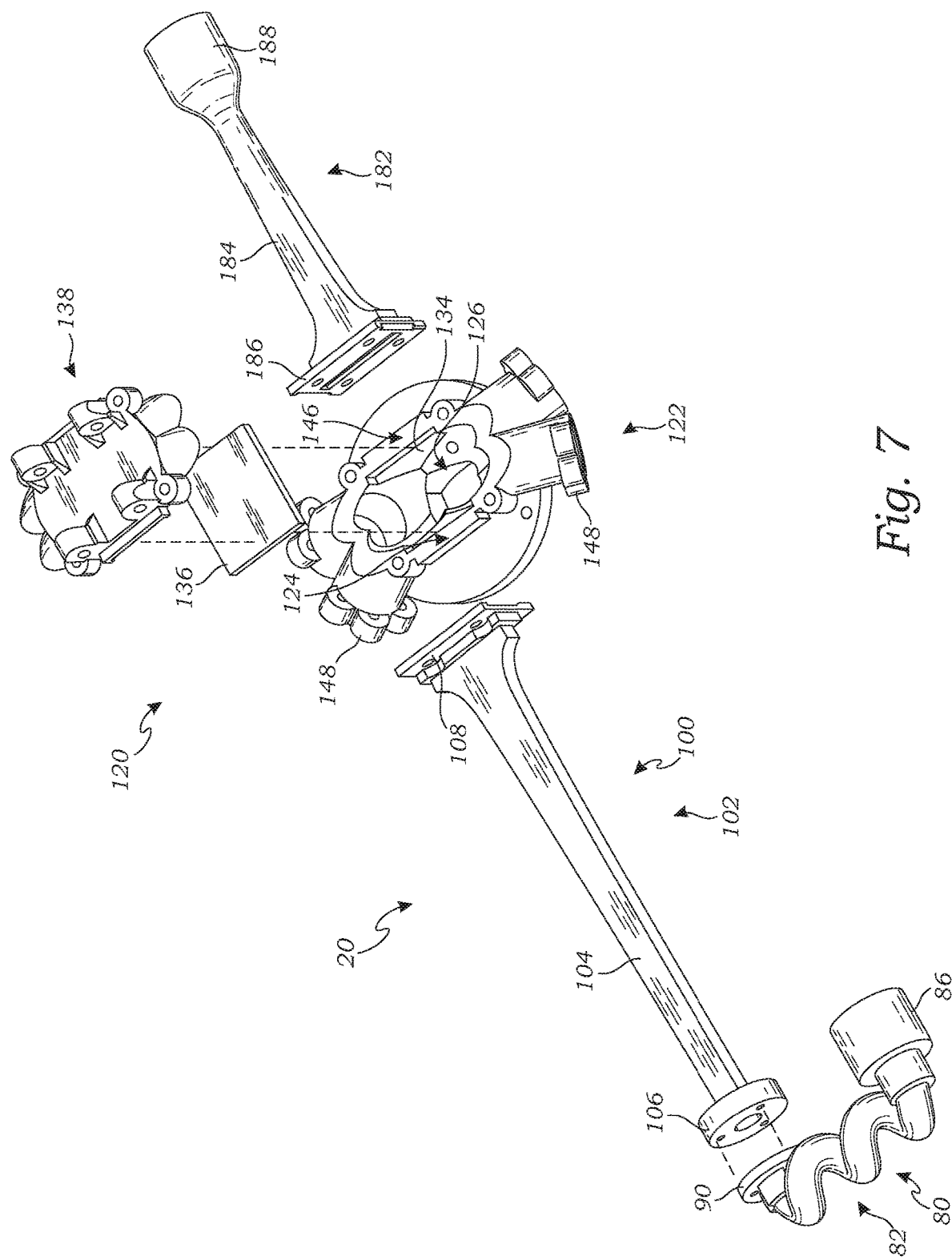
FIG. 7 is an exploded perspective view thereof taken from substantially the opposite direction as FIGS. 5 and 6, in accordance with at least one embodiment.
Figure 9:
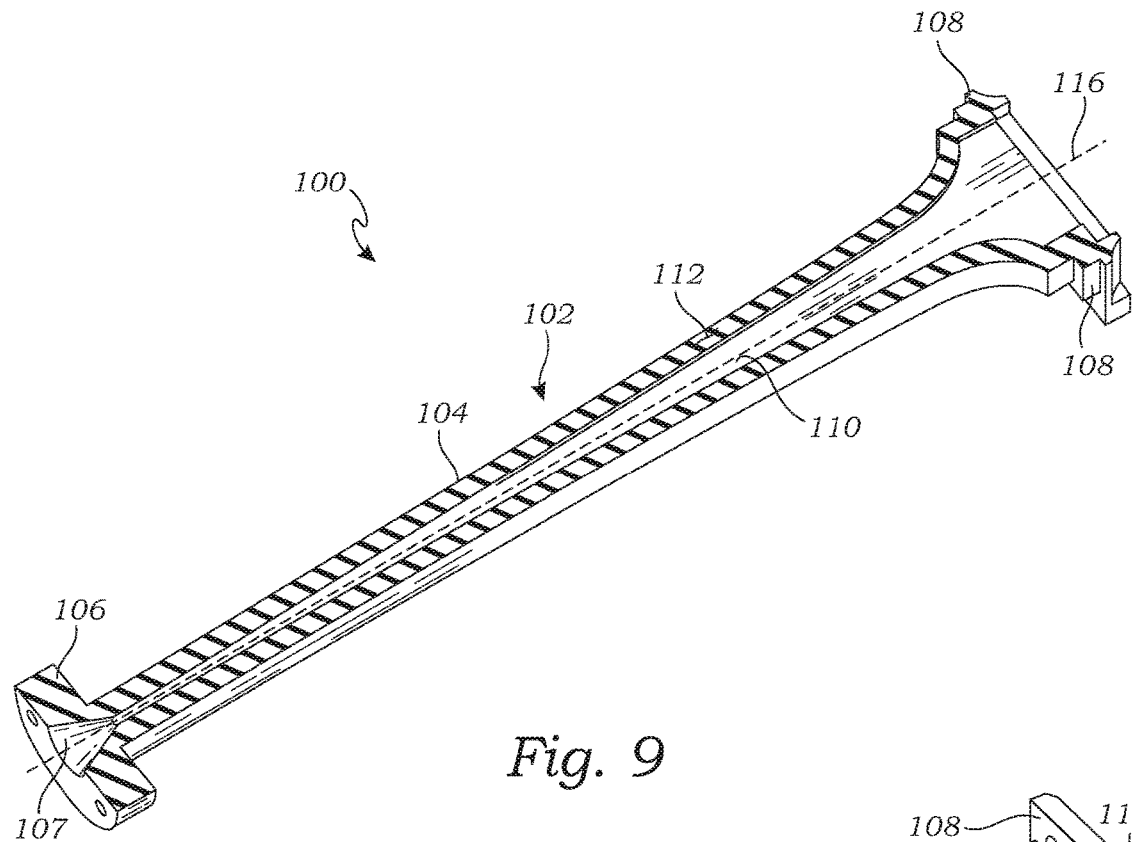
FIG. 9 is an enlarged partial top cross-sectional view thereof taken along line 9-9 of FIG. 6, in accordance with at least one embodiment.

Referring again to FIG. 5 and with further reference to the exploded perspective views of FIGS. 6 and 7, next in sequence is once again the flow normalizing section 100 that itself generally comprises the inlet chute 102. It is noted that while a section of tubing 94 is shown in FIG. 2 as interconnecting the stimulation section 80 and the flow normalizing section 100, in the embodiment shown in FIG. 5 and following, the system 20 instead has the disorientation spiral 82 connected directly to the inlet chute 102—it will be appreciated that any such connectivity of the respective parts of the system 20 is possible in the present invention without departing from its spirit and scope. The chute 102 again has at its proximal end the inlet chute first coupling 106 configured to connect to the spiral second loop coupling 90 and further has at is distal end an inlet chute second coupling 106 configured for connecting the inlet chute 102 to the viewing section body 122. Once more, though a particular form and geometry of the inlet chute second coupling 106 is shown, here in the form of plate substantially perpendicular to the axis 116 of the inlet chute 102 and having holes formed for the assembly thereof as by bolts or screws to the respective parts of the viewing section 120, the invention is not so limited. More notably, and now with further reference to the cross-sectional views shown in FIGS. 9 and 10, it can be seen that the exemplary inlet chute 102 has an inlet chute body 104 in which is formed an inlet chute inner bore 110 along its entire length. Taking first FIG. 9, a section taken through a substantially horizontal or inlet chute first plane 112, it can be seen that the bore 110 significantly tapers outwardly or expands from the entrance to the inlet chute 102 at the end adjacent the inlet chute first coupling 106 to the exit from the inlet chute 102 adjacent the inlet chute second coupling 108. In the exemplary embodiment, the proximal end of the inlet chute inner bore 110 immediately distal or downstream of the conical bore 107 defines an inlet chute first inside diameter that is substantially equivalent to the spiral inner bore 92 for a smooth transition therebetween. This substantially annular inner surface of the fluid flow path then gradually expands going down the inlet chute inner bore 110 to, in the exemplary embodiment, a final width of approximately 20 mm substantially corresponding to the width of the viewing port 144 within the viewing section 120, resulting in an expansion in this plane of about eight times (8×). Furthermore, referring to FIG. 10, a section taken through a substantially vertical or inlet chute second plane 114, or a plane substantially perpendicular to that along which the part is sectioned as shown in FIG. 9, the intersection of the inlet chute first and second planes 112, 114, in fact, being along or defining the inlet chute central axis 116, reveals that in this direction the inlet chute inner bore 110 is of a more uniform dimension. More particularly, at the entrance to the inlet chute 102 adjacent the inlet chute first coupling 106, the dimension across the bore 110 is again approximately 1.2 mm in the exemplary embodiment, which in this second plane 114 then actually tapers down slightly to approximately 1 mm to correspond to the depth of field D through the viewing section 120, more about which is said below. As such, the cross-sectional area of the flow path or inner bore 110 through the inlet chute 102 is approximately 1.1 mm2 at its entrance ($\pi d2/4 = \pi(1.2$ mm$)2/4$) while at its exit it is approximately 20 mm2 (20 mm×1 mm). It follows that there is a volumetric expansion along the inlet chute inner bore 110 of about twenty times (20×), and it will be appreciated, then, that as the sample flow passes from the disorientation spiral 82 into and through the inlet chute 102 it will have a tendency to normalize and slow down or decelerate as the flow path expands, resulting in relatively more laminar flow prior to the sample then leaving the inlet chute 102 or flow normalizing section 100 and entering the viewing section 120, a full appreciation of the benefit of which will be gained from the below discussion concerning the microorganism evaluation system 20 in use, and particularly FIGS. 16 and 17.

Figure 10:
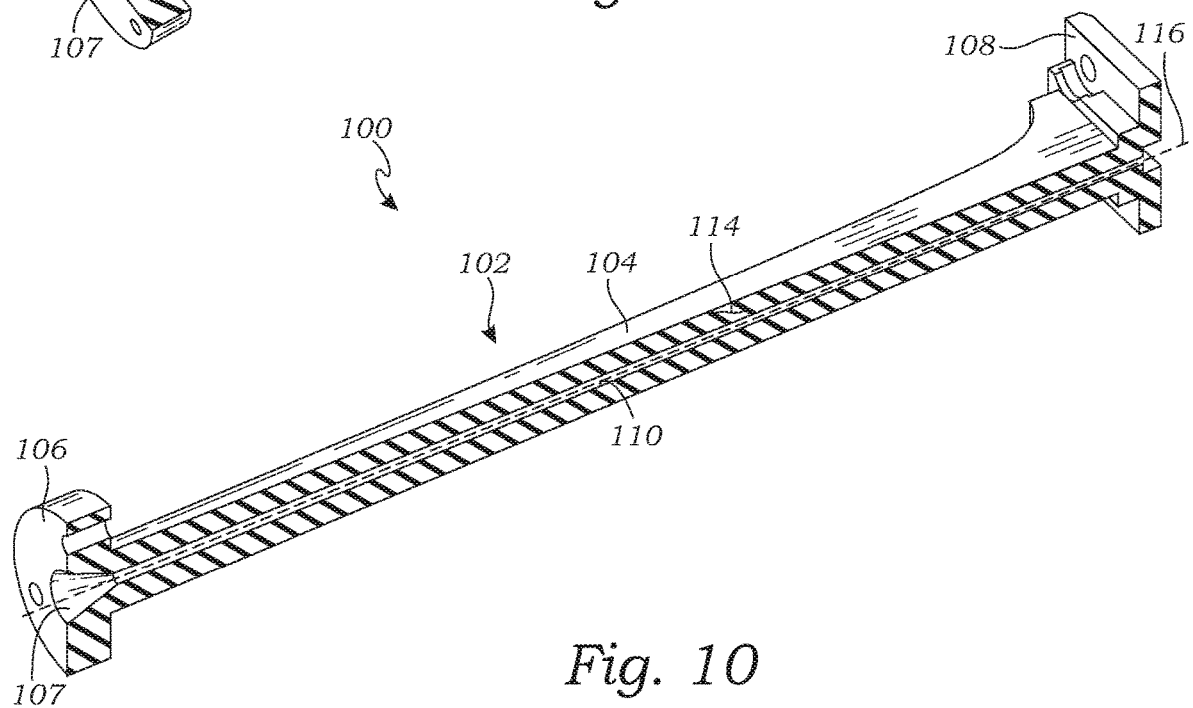
FIG. 10 is an enlarged partial side cross-sectional view thereof taken along line 10-10 of FIG. 6, in accordance with at least one embodiment.
Figure 11:
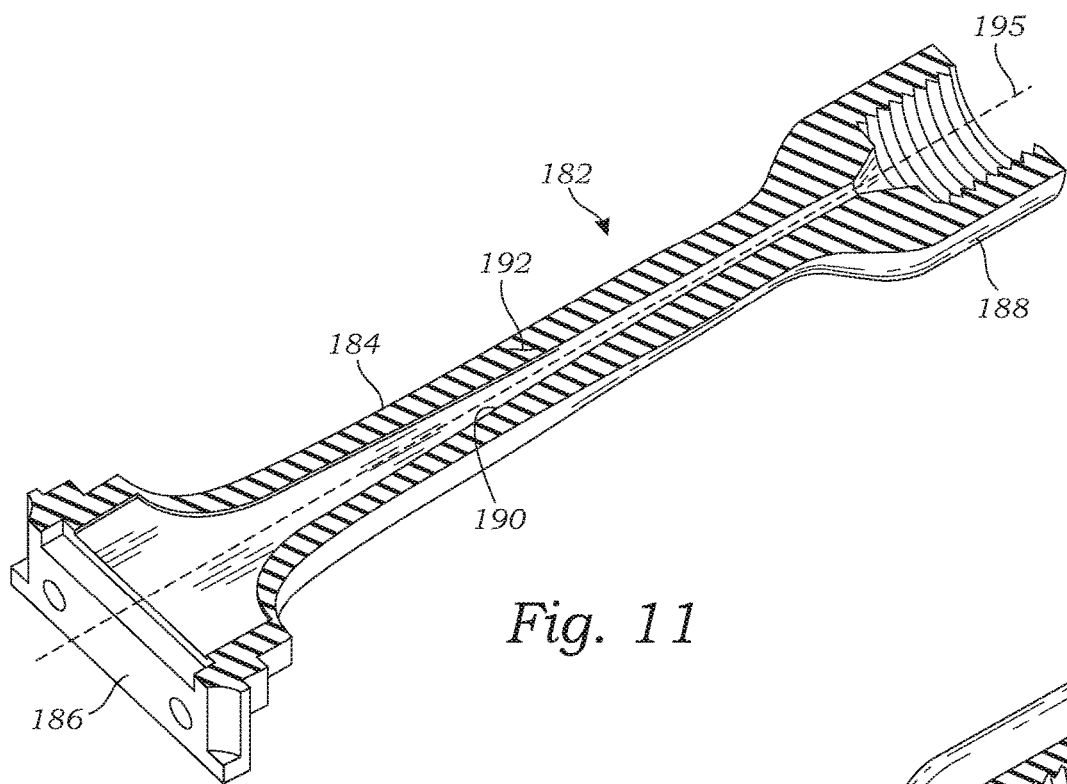
FIG. 11 is an enlarged partial top cross-sectional view thereof taken along line 11-11 of FIG. 6, in accordance with at least one embodiment.
Figure 12:
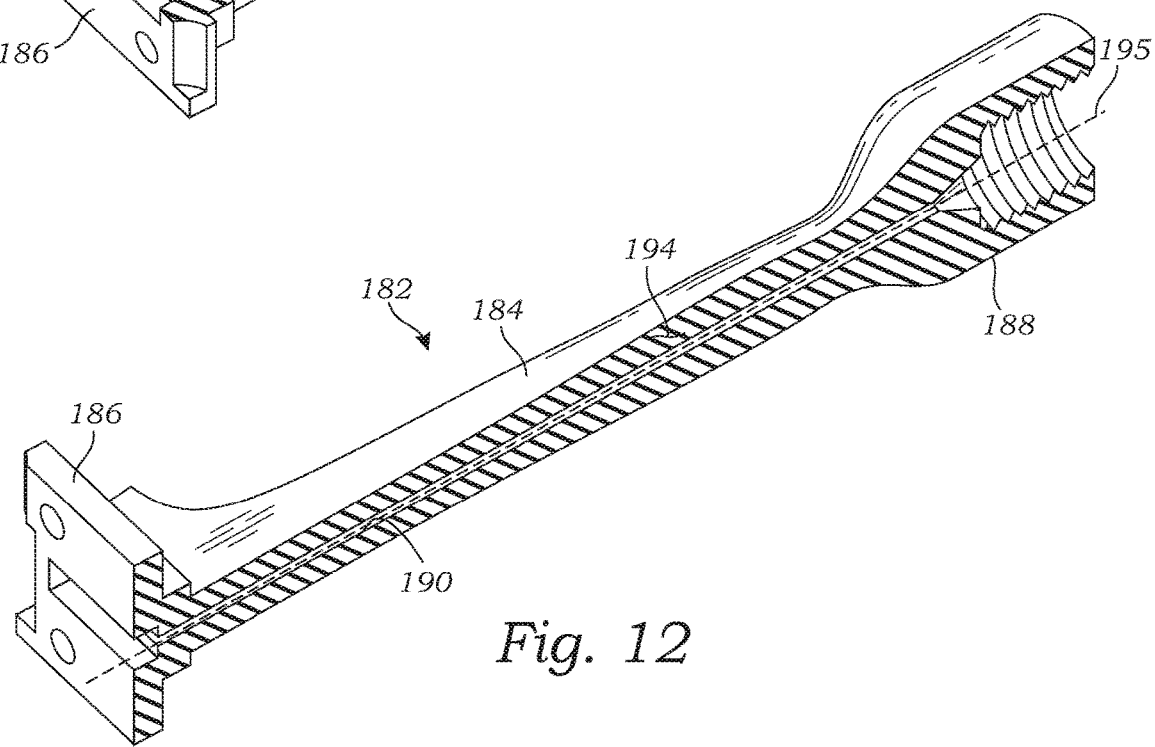
FIG. 12 is an enlarged partial side cross-sectional view thereof taken along line 12-12 of FIG. 6, in accordance with at least one embodiment.

Briefly turning to FIGS. 11 and 12, there are shown cross-sectional views of the outlet chute 182 analogous to the views of FIGS. 9 and 10 regarding the inlet chute 102, the outlet chute 182 effectively taking the sample flow away from the viewing section 100 (FIGS. 5-7) in much the same way, but in reverse, as the inlet chute 102 delivers the sample flow to the viewing section 120. Specifically, referring first FIG. 11 showing a section taken in or through a substantially horizontal or outlet chute first plane 192, it can be seen that the outlet chute inner bore 190 significantly tapers inwardly or contracts from the entrance to the outlet chute 182 at the end adjacent the outlet chute first coupling 186 that is connected to the viewing section body 122 to the exit from the outlet chute 182 adjacent the outlet chute second coupling 188 that is configured to connect to the tubing 196 (FIG. 2) leading eventually back out of the system 20. Whereas, as shown in FIG. 12, a section taken through a substantially vertical or inlet chute second plane 194, or a plane substantially perpendicular to that along which the part is sectioned as shown in FIG. 11, the intersection of the outlet chute first and second planes 192, 194, once again being along or defining the outlet chute central axis 195, reveals that in this direction the outlet chute inner bore 190 is of a more uniform dimension, here slightly expanding as the flow heads away from the viewing section 120 through the outlet chute 182. Once again, in reverse of the inlet chute 102, here with the outlet chute 182 there is an overall contraction or reduction in size of the inner bore 190 along its length in the direction of flow, which those skilled in the art will appreciate will have a tendency to gradually speed up again or accelerate the flow as it leaves the organism evaluation system 20. In the exemplary embodiment the inlet chute 102 is about twice as long as the outlet chute 182, or six inches (6 in) compared to three inches (3 in), respectively, though once more it will be appreciated that all such sizes and geometries are merely illustrative of features and aspects of the present invention and non-limiting.

Figure 13:
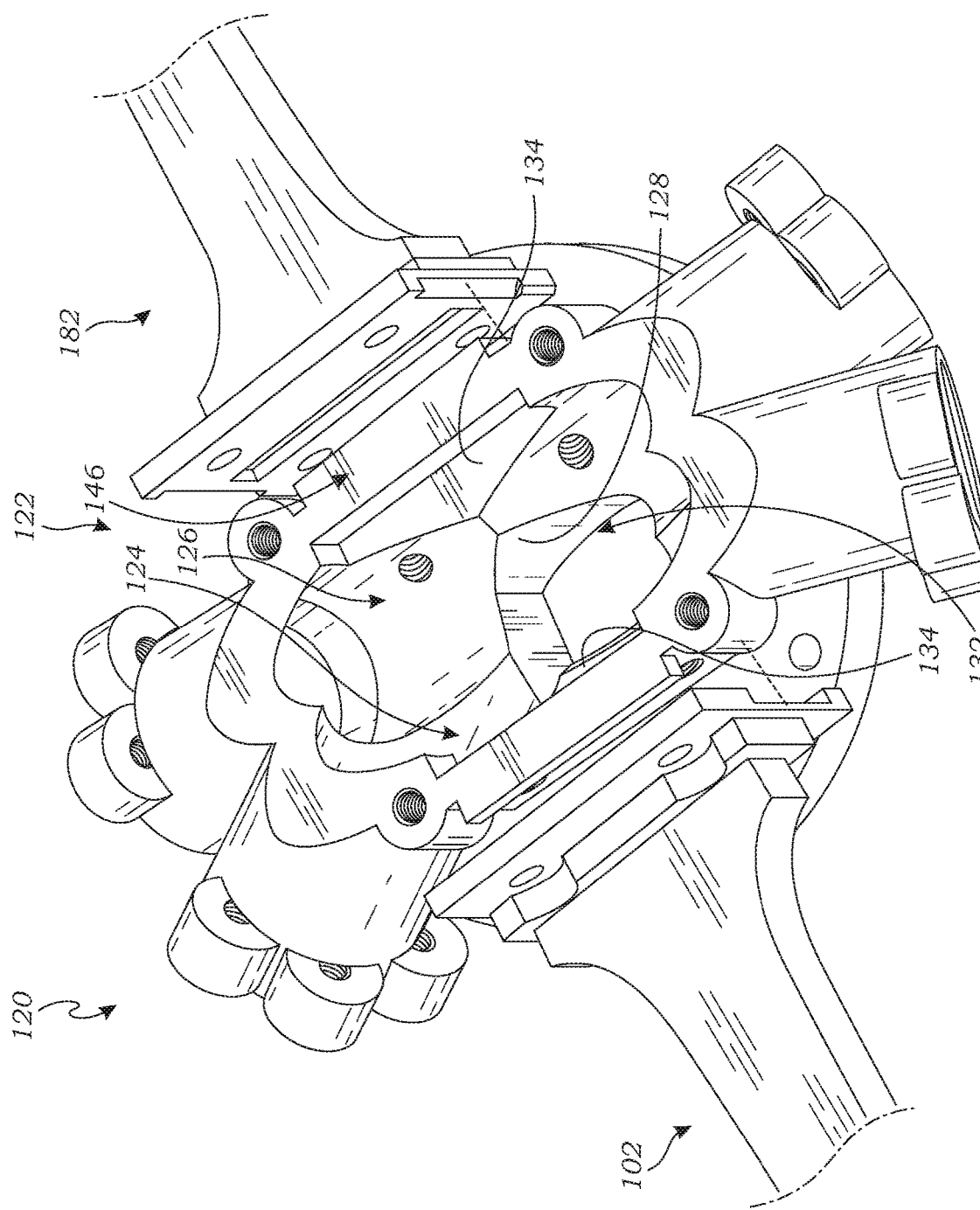
FIG. 13 is an enlarged partial bottom view thereof, in accordance with at least one embodiment.
Figure 14:
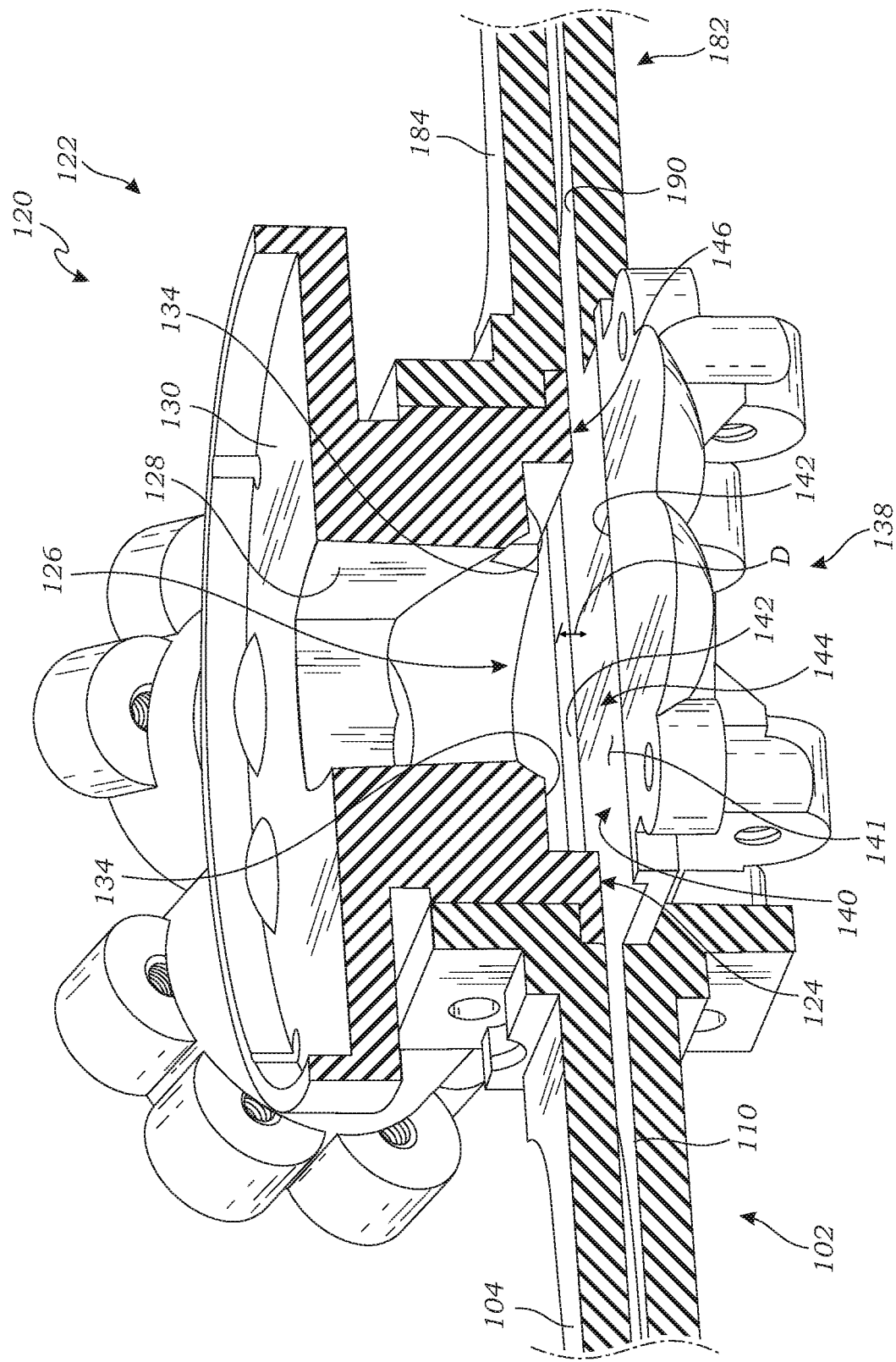
FIG. 14 is an enlarged partial cross-sectional view thereof taken along line 14-14 of FIG. 5, in accordance with at least one embodiment.

Referring again to FIGS. 5-7 and now with reference to FIGS. 13 and 14 as well, downstream of the flow normalizing section 100, or between the inlet and outlet chutes 102, 182, is again of course the viewing section 120. In the partial exploded view of FIG. 13, which is effectively the viewing section body 122 upside down with the back plate 138 not shown for clarity, it can be seen that in the exemplary embodiment the body 122 effectively has a viewing section body inlet 124 coinciding with the distal end of the inlet chute 102 at its second coupling 108 and a viewing section body outlet 146 coinciding with the proximal end of the outlet chute 182 at its first coupling 186, which inlet 124 and outlet 146 are each in fluid communication with the hollow interior of the viewing section 120, or the viewing section body cavity 126. In FIG. 14 there is shown a partial cross-sectional view of the viewing section 120, here with the viewing plate 136 not shown for clarity. As best appreciated from FIGS. 6 and 14, three sides of the actual viewing port 144 or the true flow path through the viewing section body cavity 126 are formed by a channel 140 formed in the back plate 138 that installs over the relatively larger cavity second opening 132 substantially opposite the cavity first opening 128 adjacent the viewing section optical system 160 as described above to substantially enclose the cavity 126, the back plate channel 140 having a channel bottom 141 and substantially perpendicular channel side walls 142. Opposite and substantially parallel to the channel bottom 141 there is positioned a clear or substantially transparent viewing plate 136 offset from the cavity first opening 128, the viewing plate 136 seating on opposite cavity shelves 134 formed in the viewing section body 122 so as to open into the cavity 126 and thus forming the fourth side of the viewing port 144. In the exemplary embodiment, the viewing plate 136 also seats on the tops of the channel side walls 142, or is pinched between the channel side walls 142 and the cavity shelves 134, such that it will be appreciated that the depth of the channel 140, or the height of the channel walls 142 effectively defines the height of the flow path through the viewing section 120 or the depth of field D for the optical system 160 that is "looking at" the sample flow through the cavity first opening 128, a portion of the open cavity 126, and the viewing plate 136 beneath which the flow is passing. It will be further appreciated that the dimensions of the viewing plate 136 substantially set the "footprint" size of the viewing port 144, which in the exemplary embodiment is 11.25 mm long by 20 mm wide, setting then a viewing port volume (L×W×H) of approximately 225 mm3 (11.25 mm×20 mm×1 mm). Again, this general geometry is discussed further below in terms of throughput and operation of the overall system 20, particularly in the context of FIGS. 16 and 17. With continued reference to FIGS. 5-7, 13 and 14, there is also shown multiple illumination ports 148 intersecting the viewing section body 122, in each of which there may be installed LEDs or the like so as to illuminate the interior cavity 126 of the viewing section 120, and the viewing port 144, specifically. Again, any number and configuration of such illumination ports 148 and any lighting units now known or later developed may be incorporated into the viewing section 120 without departing from the spirit and scope of the present invention.

Figure 15:
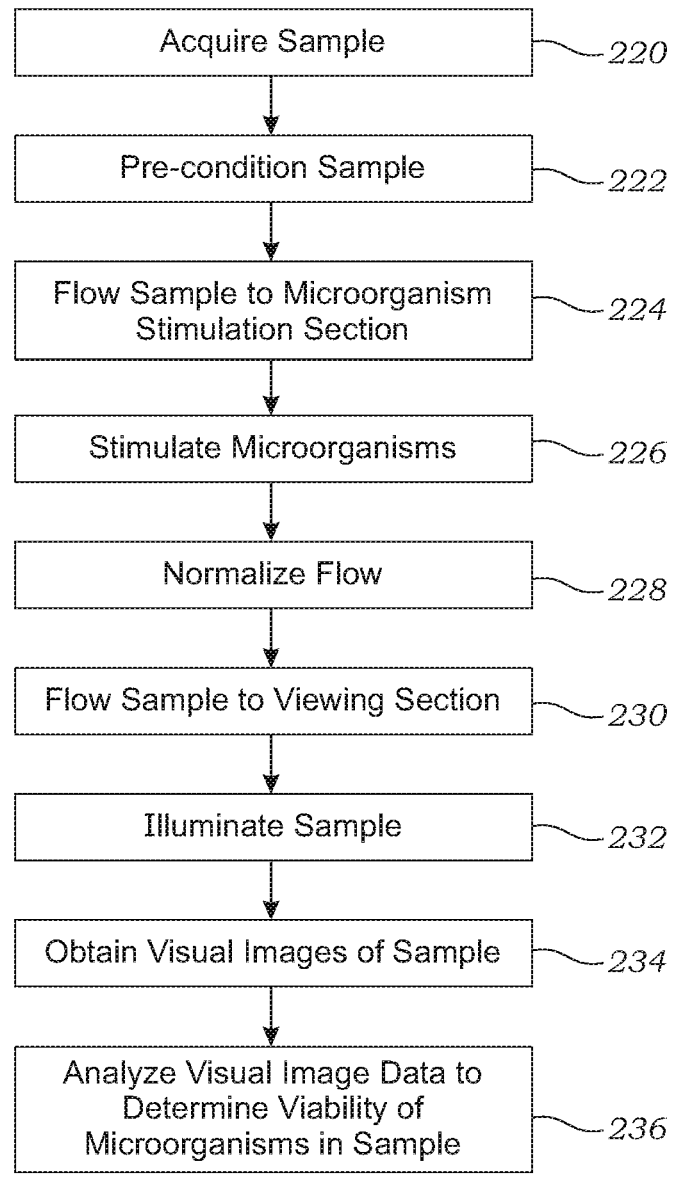
FIG. 15 is a flow chart representing the use thereof, in accordance with at least one embodiment.

Referring next to FIG. 15, there is shown a flow chart depicting the basic operation or use of a organism evaluation system 20 according to aspects of the present invention. In use of such an exemplary system 20 as shown in FIGS. 1-14, the first step 220 is to acquire the sample to be tested, which is beyond the scope of the present invention, though per the embodiment shown in FIGS. 1 and 2, there is one exemplary embodiment effectively a tank system identified here as the sample pre-conditioning section 30 made up of one or more tanks, here an external sample tank 32 and a main sample tank 52 (FIGS. 1 and 2), that together hold a finite volume of fluid sample for evaluation within or by the system 20. It will be appreciated that in other contexts different types and numbers of tanks may be employed, or a more continuous system may be employed wherein the fluid sample is acquired on a more real-time basis from a larger body or flow of water or other fluid. Once a sample is acquired, in step 222 the sample may be pre-conditioned, which stands for the general proposition of removing from the fluid sample inorganic or dead organic matter as by settling, filtration, or other appropriate techniques now known or later developed, so that what is primarily left in the water sample is organic material that may or may not be living, which determination is the primary purpose of the present invention. At step 224 the fluid sample is flowed to the microorganism stimulation section 80 (FIGS. 1 and 2), and at step 226 any microorganisms therein are stimulated, which again may be inertial stimulation as per the disorientation loop 82 shown in FIGS. 2 and 5, may be hydraulic or mechanical stimulation as shown and described below in connection with the alternative exemplary embodiments of FIGS. 18 and 19, or may be any other such stimulation device or method now known or later developed, any such device or method again stimulating or exciting the senses of the microorganisms, as compared with chemical staining or response and other such techniques known and employed in the art in determining organism life or viability, though in certain contexts such evaluation techniques (motive and chemical) may be used in tandem. At step 228, the flow is normalized as by flowing through the exemplary flow normalizing section 100 (FIGS. 1 and 2), and then at step 230 the sample passes into the viewing section 120 (FIGS. 1 and 2). At step 232 the sample within the viewing section 120 may be illuminated as by the illuminator 150 (FIGS. 1 and 2), and then the optical system 160 (FIGS. 1 and 2) in conjunction with the imager 170 (FIGS. 1 and 2) may obtain visual images of the sample at step 234. Finally, in terms of the general process or method of using the system 20, at step 236, the visual image data is analyzed to determine whether any of the microorganisms within the sample are living.

Figure 16A:
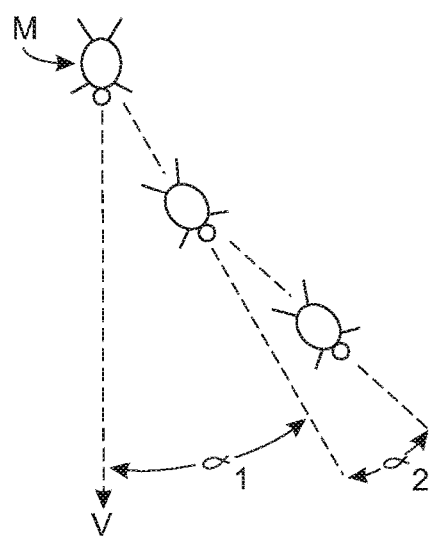
FIG. 16A is a schematic representation of a self-induced change in the direction of movement of a microorganism.
Figure 16B:
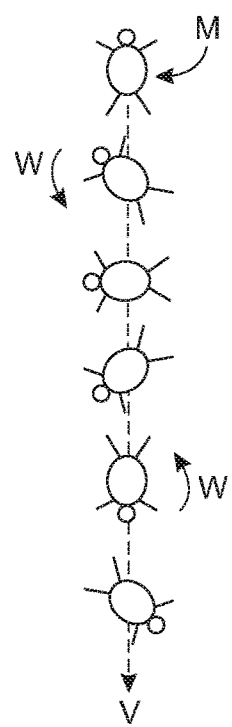
FIG. 16B is a schematic representation of a self-induced change in the orientation of a microorganism.
Figure 16C:
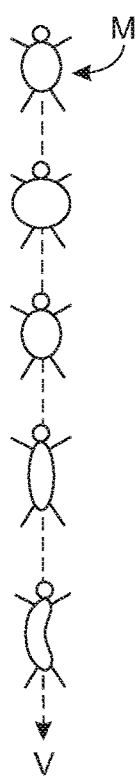
FIG. 16C is a schematic representation of a self-induced change in the aspect ratio of a microorganism.

In connection with this last step 236 (FIG. 15) and the analysis of the microorganisms of which image data is captured in the viewing section 120 after being excited in the stimulation section 80, referring now to FIGS. 16A-16C, there are shown schematics of essentially three different motive responses of a microorganism M that may be induced and thus be observed within the viewing section 120. The theory again is that the helix geometry of the disorientation spiral 82 (FIGS. 2 and 5) will induce the fluid in the tube to rotate around the tubular axis, which will stimulate (agitate) the inertial sensing mechanisms found within the microorganisms. A finite amount of time after the stimulation event has ended the living microorganisms will react with self-generated motion as their inertial measurement system stabilizes while they are floating in the "calm waters" of the viewing section 120. For example, they may attempt to straighten themselves out after they sensed being tumbled around. Another way of describing the thinking embodied in this aspect of the invention is that the microorganisms will react to "feeling dizzy." Accordingly, the microorganism stimulation section 80 shown in FIGS. 2 and 5 supports momentary stimulation of a live organism's inertial sensory perception. The amplitude and duration of stimulation necessary to induce such a response as self-generated motion, as by a "tumbling" microorganism attempting to "right" itself, can be characterized by both a frequency spectrum and a rotational time history. The frequency spectrum is particularly characterized by amplitude and frequency of the stimulation and can be expressed as power spectral density ("PSD"), whereas the rotational time history is particularly characterized by the rate and duration of the organism's motive response to the stimulation and can be expressed as energy spectral density ("ESD"), or the energy of the disorientation event. Certain microorganisms will be particularly sensitive to certain frequencies and amplitudes ("PSD"), which will be excited by an appropriate geometry of the spiral loop agitator or other such stimulus ("ESD"), as described above in connection with other aspects of the exemplary system of FIGS. 1-14 as well as in connection with the alternative embodiments shown particularly in FIGS. 18 and 19. Thus, the geometry or other properties of the helix are determined by the PSD, ESD, and acceleration profiles that are required to properly stimulate the microorganism M. In a bit more detail, again, the PSD describes both the frequency and amplitude of the stimulation event. Whereas, the ESD describes the time-history of the rotation profile of the stimulation event, such that the integral of this time-history, or "area under the curve," is the energy induced on the microorganism M during the stimulation event. Accordingly, the rotation profile depicts the "slopes" of the event, which is the rate of change of the rotational forces induced on the microorganism M. With a certain acceleration or rate-of-change in rotation being desirable, it being observed that microorganisms will adapt to relatively gentle motions and not necessarily generate counter-acting self-induced motion, while adequately rapid changes in the local hydrodynamic environment, or in acceleration or motion more generally, will tend to cause self-induced motion by the microorganism M. The optimal amount of stimulation required is bounded in both amplitude and duration, in that both parameters requiring a minimum threshold to be exceeded, and a maximum to not be attained. It will thus be appreciated once more that various geometries and features of the microorganism stimulation section 80 are possible beyond the double-loop spiral agitator 82 depicted in FIGS. 2 and 5, again depending on the type of organism that is to be evaluated, fluid type and flow characteristics, and other such contextual factors. Generally speaking, vertical orientations of the stimulation section 80 are preferred due the decoupling from localized pitching or roll motion (as on a boat for example), and the tendency of Zooplankton to generate a more vertical motion that supports a typical feeding pattern. Once more, then, those skilled in the art will appreciate that the invention is not limited to the particular stimulation section shown and described in connection with FIGS. 2 and 5, but may instead take a number of other forms to suit a particular context without departing from the spirit and scope of the invention. For example, in alternative embodiments, direct hydraulic excitation or indirect hydraulic (mechanical) excitation may be employed instead, such as by transverse water flows or vibration induction, as represented schematically in FIGS. 18 and 19. Any such approach would again employ a power spectral density ("PSD") generator to quantify the stimulation (amplitude and frequency of vibration or intensity/pressure and frequency of water pulses), more about which is said below. In connection with the "two loop" disorientation spiral 82 shown in FIGS. 2 and 5, such will tend to "saturate" the inertial sensing mechanism ("ISM") of the microorganism M so as to yield relatively more consistent results when the organism M is "released" from the spiral 82. In the exemplary embodiment, the geometry of the disorientation spiral 82 and the contemplated flows therethrough produce a rotational inertial stimulus of approximately six radians per second (6 rad/sec). After the flow normalization section 100 and entry of the sample into the viewing section 120 having in the exemplary embodiment a relatively high width-to-height aspect ratio, on the order of twenty to one (20:1), with the viewing chamber volume (L×W×H) again being 11.25 mm×20 mm×1 mm, it has been determined, for example, that utilizing current video camera technology with a nominal output resolution of 2.1 megapixels can resolve down to about ten (10) microns and will still allow for one to five second (1-5 sec) dwell times within the viewing port 144 and the acquisition of twenty (20) or more discrete frames per organism M—a sufficient and even substantial data set from which to make determinations regarding relative movement and hence organism life.

Referring first to FIG. 16A, then, there is shown schematically a microorganism M changing its direction incrementally by an angle α from the initial flow velocity vector v, indicating that it is living in deviating from the course or direction along which a non-living organism would be carried. This is one example of a motive response from a microorganism M that is essentially "swimming" in the "calm waters" of the viewing section 80 after having its ISM was saturated in the spiral stimulation section 80. As shown in FIG. 16B, another exemplary motive response is an organism M spinning as it travels along the normal flow velocity vector v, which again is not motion that would be induced by the laminar substantially straight-line flows through the viewing section 120, but would be indicative of self-generated motion by a living organism. And finally, as shown in FIG. 16C, yet another exemplary motive response that may be observed in a microorganism M that has been stimulated is a change in aspect-ratio, which essentially entails an organism twisting or wriggling or otherwise flexing or moving its body, any of which would again be self-generated and not a result of the sample flow, particularly within the viewing section 120. It will be appreciated that while discrete organism responses are shown in FIGS. 16A, 16B, and 16C, multiple such responses may be present in a single organism at the same time, such as an organism deviating from the normal flow velocity path and simultaneously rotating or spinning (combination of FIGS. 16A and 16B) or an organism maintaining the same flow velocity path but also wriggling and curling while rotating (combination of FIGS. 16B and 16C). Any combinations of such motive responses and others are possible, and the detection of one or more such movements as an organism passes through the viewing section 120 would be sufficient to indicate life.

Figure 17A:
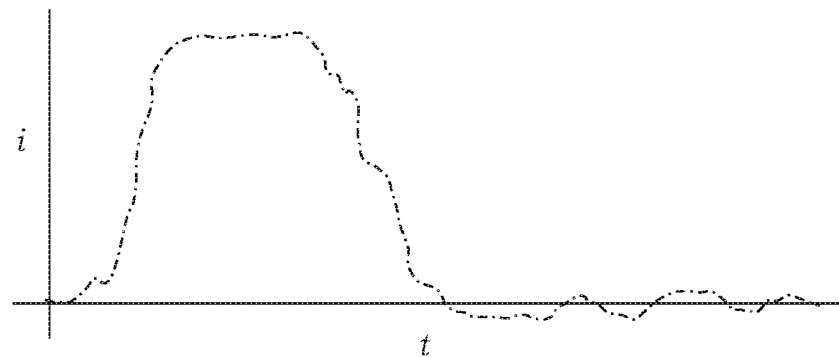
FIG. 17A is a graph depicting the inertial stimulation over time to which the microorganism is subjected, in accordance with at least one embodiment.
Figure 17B:
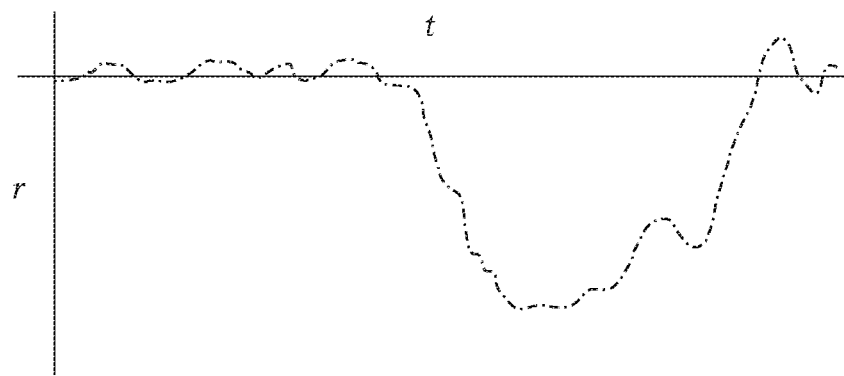
FIG. 17B is a graph depicting the response of a microorganism over time in response to the inertial stimulation depicted graphically in FIG. 17A, in accordance with at least one embodiment.

In terms of the organism image data aggregation and analysis—the detection and interpretation of microorganism motive response—attention is now directed to FIGS. 17A and 17B depicting the stimulation energy supplied to an organism and that organism's measured response, respectively. By way of further background, this portion of the discussion relating effectively both to the capabilities of the optical system 160 and imager 170 as well as the image capture and processing hardware/software 210 and the kinematics analysis algorithm 212, in addition of course to the geometry of the components and flow rates therethrough as described above, under certain conditions "artifacts" will be created by the digital imager 170, which will or could make quantitative interpretation incorrect. That is, there will be a certain level of inaccuracy in the amount of frame-to-frame apparent "motion" observed, depending on a number of factors. In a practical sense, when applying a derivative function it will tend to amplify any inaccuracies in spatial content, and therefore make more strict quantitate analysis problematic. However, there is relative robustness with the current approach regarding the identification of deviation from normal, not "how far" from normal; a qualitative analysis of the data—as in "Did the microorganism M move from the normalized path v?"—is an adequate determination in this context. Put another way, it is not necessary to know "how much" the microorganism M moved to know whether or not it is alive; detection of some movement (linear or rotational or of the aspect ratio, for example) from the normalized path or a starting orientation or body shape will qualitatively determine organism life, while still leaving open the option for quantitative assessment, including based on technological advances so as to reduce or eliminate the "artifacts" in the image data that could skew quantitative results. Technology in terms of optics (resolution) and processing (data transfer and compiling) is continuing to improve, so the artifacts that are generated will become less significant over time. And a very small percentage of the pixels will be changing from frame to frame in the present application, which will significantly reduce the amount of artifacts generated already. To further assist, the relatively small depth of field D (FIG. 4), in the exemplary embodiment on the order of one millimeter (1 mm), enables opening up the camera aperture and letting in more light for the image sensor 160, running greater practical shutter speed values, and producing greater clarity in the images captured.

Back to FIG. 17A, then, there is shown a graph depicting a representative inertial stimulation i (vertical axis) over time t (horizontal axis) to which the microorganism M is subjected. As can be seen, for a certain duration there is a definite inertial event, such as corresponding to the time the organism spends in the stimulation section 80, or the disorientation spiral 82, specifically, which energy then dampens out over time following discharge from the stimulation section 80, essentially corresponding to the time the organism spends in the flow normalizing section 100 and then the viewing section 120 where the flow rate of the fluid sample is slowest (the organism would have the longest "dwell time" in the "calm waters" of the viewing section). Then with reference to FIG. 17B, there is shown a similar graph now plotting a representative motive response r (vertical axis) over time t (horizontal axis), with the vertical axes of FIGS. 17A and 17B aligned so as to easily see the motive response r, as expected, time-wise lagging the inertial stimulation i. Moreover, the response r is plotted below the horizontal axis, or "negative," simply to indicate that the response r is in reaction to and "equal and opposite" or "proportional" to the inertial stimulation i. Notably, once again, it can be seen via a comparison of FIGS. 17A and 17B that it is not until after the inertial stimulation event has ended and the inertial stimulation i has begun to dampen out that the organism response r then sharply picks up, which period of active response again, based on the geometry and flow rates within the system 20, is to coincide with the time the organism is passing through the viewing section 120, which in the exemplary embodiment is to be approximately on the order of one to five (1-5) seconds. Those skilled in the art will appreciate that the graphs shown in FIGS. 17A and 17B, though based on actual observations, are not based on empirical data or the plotting of data points, and so in some sense are theoretical and so are not to be taken strictly or literally, hence there being no values or graduations on the graph axes. Accordingly, it will also be appreciated that various other scenarios of the inertial stimulation i and the motive response r are possible within the present invention without departing from its spirit and scope.

Figure 18:
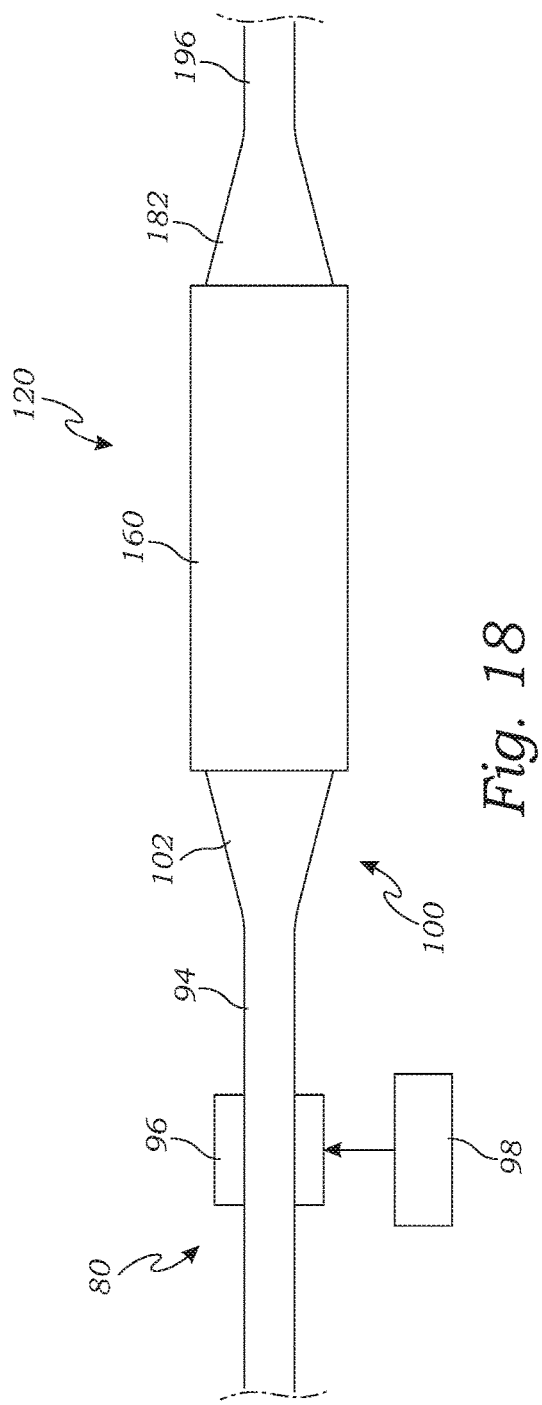
FIG. 18 is a partial schematic representation of an alternative exemplary organism evaluation system, in accordance with at least one embodiment.
Figure 19:
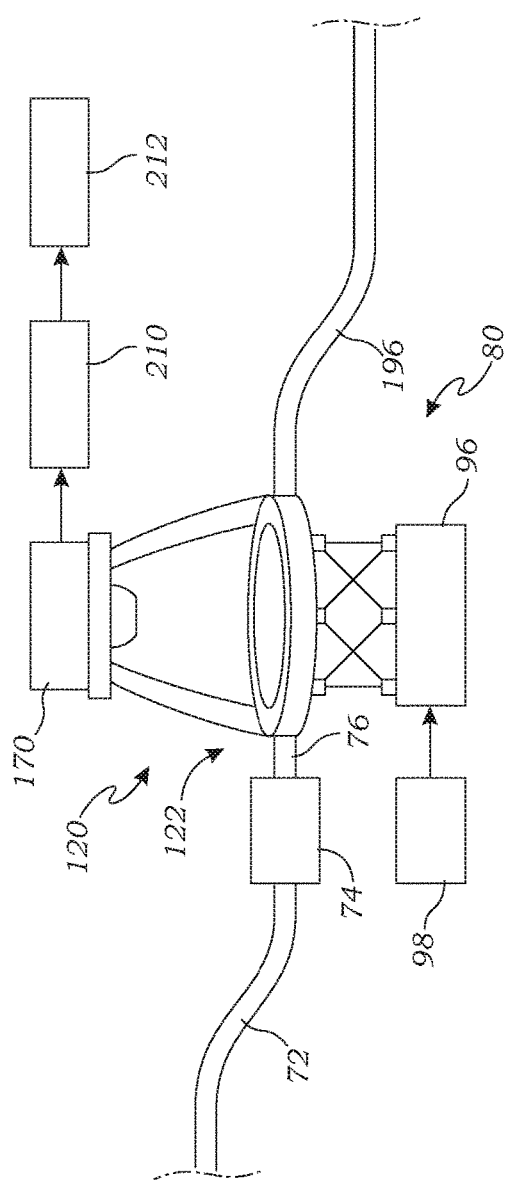
FIG. 19 is a partial schematic representation of a further alternative exemplary organism evaluation system, in accordance with at least one embodiment.

Turning now to FIG. 18, there is shown a schematic view of an alternative exemplary embodiment of a organism evaluation system 20 according to aspects of the present invention. Here, it is indicated that a hydraulic and/or mechanical excitation device 96 may be employed in or adjacent the flow some distance upstream of the viewing section 120, which agitator would again be coupled to a PSD generator 98. Generally, forces are hydraulically coupled to the organisms in the sample due to the fact that they are suspended in fluid. In direct hydraulic excitation or stimulation, a series of small tubes (not shown) intersecting the flow path may be employed to agitate the organisms as they pass through this excitation section 80, such as by a steady cross-flow or bursts or pulses of fluid transverse to the primary axis of fluid flow. Any such disruption, causing turbulence and tending to disorient the organisms, would thereby induce self-generated motion by living organisms in response, as discussed above. The concept of a reaction delay or an "agitation response decay time" wherein motion of the organisms is given time to commence but not too much time so as to commence and then cease before the viewing section 120, while still providing sufficient length in a normalizing section 100 or the like for the flow to normalize, as discussed above particularly in connection with FIG. 2, would again be applicable here in the context of hydraulic and/or mechanical excitation. With mechanical (indirect hydraulic) excitation, as in the system schematic of FIG. 19, the stimulus mechanism is effectively mechanical to hydraulic to inertial, such that this approach would be relatively less direct, as it is believed that ultimately the organisms respond to inertial stimuli. Either approach would again employ a power spectral density ("PSD") generator 96 to quantify the stimulation (amplitude and frequency of vibration in the context of mechanical excitation or intensity/pressure and/or frequency of water pulses in hydraulic excitation), and though the mechanical approach is shown in conjunction with stimulation at or contemporaneous with the viewing section 120 and the hydraulic approach upstream of the viewing section 120, other such variations are possible. Once more, it will be appreciated by those skilled in the art that while various embodiments and related operation have thus been shown and described, and particularly various means of exciting, agitating, or otherwise stimulating microorganisms, the invention is not so limited, but may instead involve any means now known or later developed for imparting at least inertial stimulation to organisms within a fluid flow for the purpose of determining whether any are living based on detected responsive movement and/or motion. Moreover, in some embodiments inertial stimulation may not even be employed, instead relying on some other agitator such as relative velocity, relative pressure, or light to stimulate the organisms in the test sample. Accordingly, it is to be expressly understood that features or aspects of the present invention as disclosed herein may be combined in various ways to achieve further alternate microorganism evaluation systems without departing from the spirit and scope of the invention.

Figure 20:
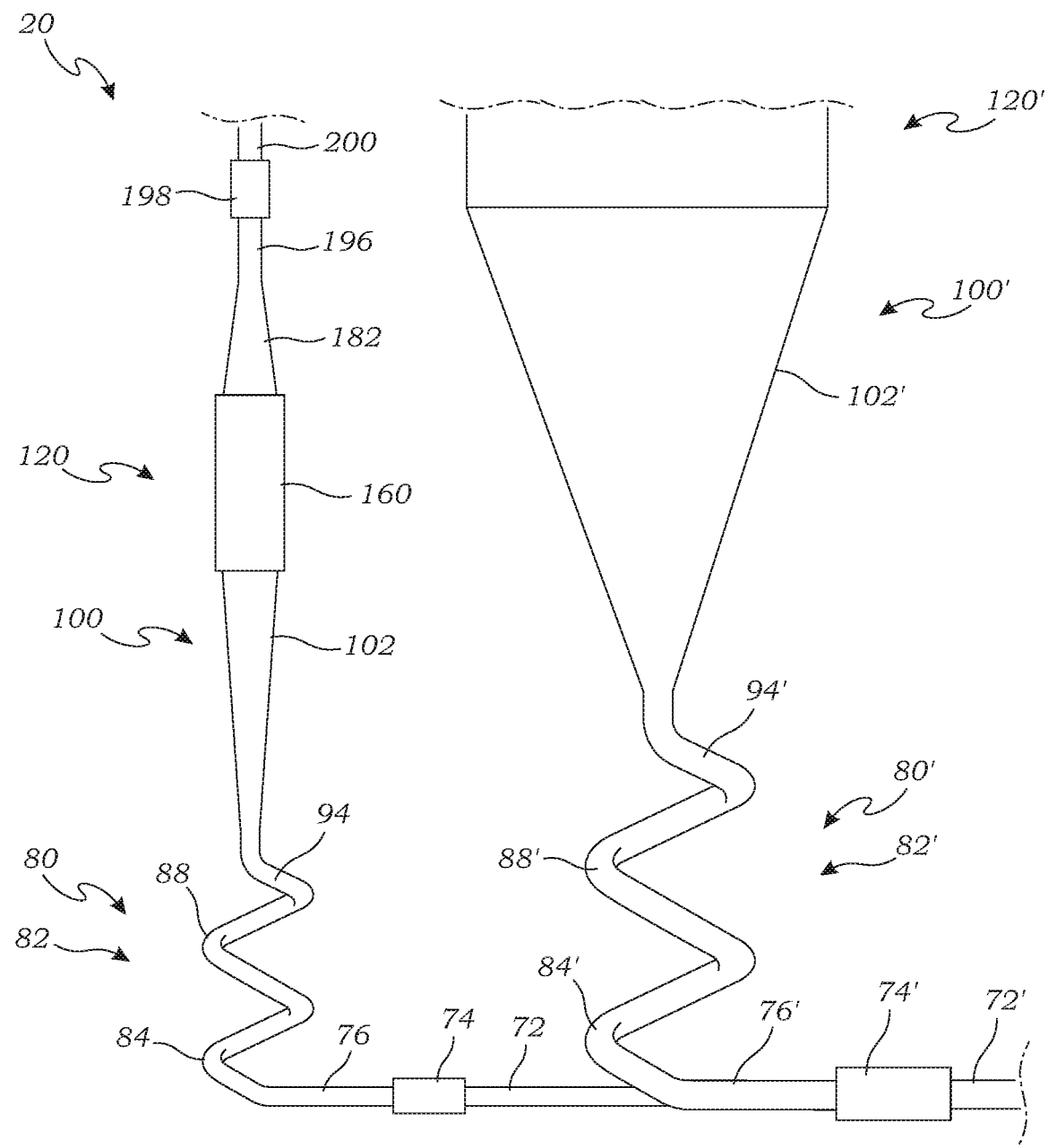
FIG. 20 is a partial schematic representation of a still further alternative exemplary organism evaluation system, in accordance with at least one embodiment.

Finally, in FIG. 20, there is shown an alternative dual organism evaluation system 20 having a first or primary, relatively larger microorganism stimulation section 80' that is otherwise quite analogous to that of the system 20 of FIGS. 1-14, which stimulation section 80' is itself sampled by a secondary microorganism stimulation section 80 that is in most respects the same as that of the first exemplary embodiment of FIGS. 1-14, such sampling being as by isokinetic sample, for example. For illustration, the larger disorientation spiral 82' may have an inside diameter of approximately 13 mm feeding into a viewing section 120' that is nominally 100 mm wide by 6 mm high, as compared to that of the first exemplary embodiment wherein the secondary spiral 82 in the dual system 20 of FIG. 20 has a nominal inside diameter of 1.2 mm and a viewing section 120 that is nominally 20 mm wide by 1 mm high. The resulting dual system 20 enables more throughput for use in contexts where larger volumetric or real-time sampling is desired as well as potentially enabling higher accuracy by secondary line sampling and evaluation within a viewing section 120 that has a nominal 1 mm depth of field while still allowing an acceptable aggregate throughput by employing the primary line having a nominal 6 mm depth of field, or a cross-sectional area of 600 mm2 versus the 20 mm2 of the secondary line that is more analogous to the exemplary embodiment system 20 according to aspects of the present invention. It will once again be appreciated that such features may be combined in a variety of ways and employ a variety of technologies now known or later developed without departing from the spirit and scope of the invention.

Referring next to FIGS. 21-31, there are shown generally further exemplary embodiments of an organism evaluation system 10 according to aspects of the present invention in the context of fish monitoring versus microorganism. Again, any such systems 20 may be scaled up or down or combined or "mixed and matched" in various ways to form other related organism evaluation systems illustrative but non-limiting of features and aspects of the present invention without departing from its spirit and scope. Here, there is provided an organism evaluation system 20 in various embodiments and having various sections or sub-systems that allows for batch or continuous real-time monitoring of water within a waterway or other body of water and thus of fish or the like within the water and provides further advantages over prior art test systems and approaches, the support of continuous real-time monitoring being particularly advantageous for several applications. The subject invention, though again in the context of fish monitoring, may be practiced in a wide array of marine life and other contexts and so is not limited to the exemplary fish monitoring context.

Figure 21:
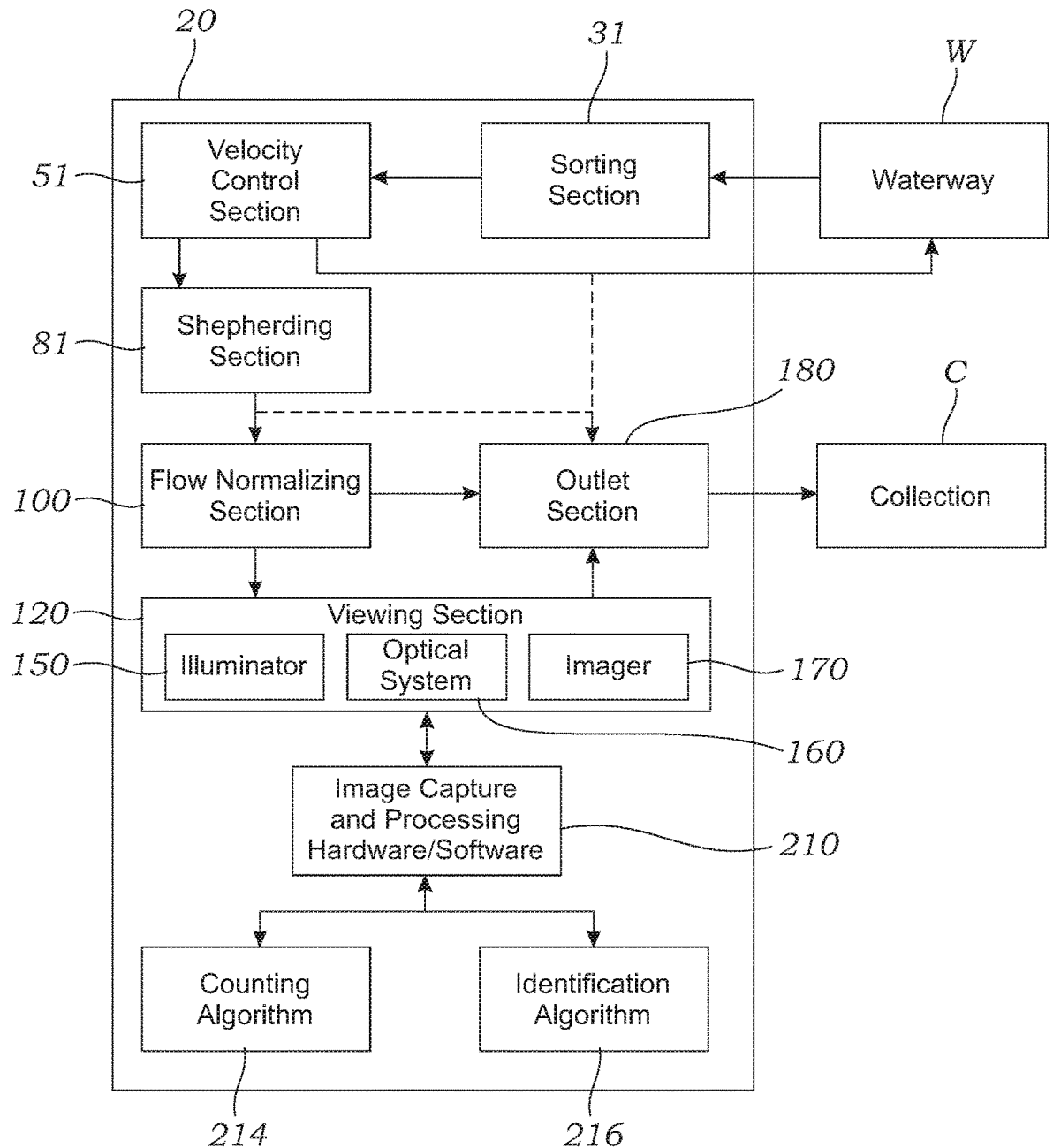
FIG. 21 is a block diagram illustrating a still further alternative exemplary organism evaluation system, in accordance with at least one embodiment.

Turning now to FIG. 21, there is shown a block diagram of a further exemplary embodiment of an organism evaluation system 20 according to aspects of the present invention. The system 20 comprises, in the alternative exemplary embodiment, four main hardware components or sections, which are discussed in turn below: (1) a sorting section 31; (2) a velocity control section 51; (3) a shepherding section 81; and (4) a viewing section 120. Upstream of the viewing section 120 and serving as its inlet is a flow normalizing section 100 and downstream of the viewing section 120 is an outlet section 180 that supplies the fish shepherded from the waterway W to a collection container C. There are related tanks, tubes, flow controls and other aspects that facilitate the collection and processing of the flow and related marine sample(s), which may be necessary in particular contexts but are nevertheless ancillary components that can be substituted for by other equivalent structure (e.g. pumps, pipes, etc.) and so are not the focus of the present invention except where noted. It will be appreciated by those skilled in the art that the exact configuration of the system and its four main sections may take a number of forms to suit particular applications without departing from the spirit and scope of the present invention. Accordingly, it will be further appreciated that the configurations of the system shown and described are exemplary and that the invention is not so limited. Moreover, once again, while "water" is discussed throughout as the sampled fluid, it is to be understood that the invention is not so limited and other fluids may be sampled as well, again depending on the context. Relatedly, it is assumed for these purposes that whatever fluid is sampled it contains marine life or other such organisms, living or dead; in the exemplary context of water flow sampling within California's Sacramento Delta the Delta smelt (*Hypomesus transpacificus*) fish is the marine life sampled, which may be in the range of approximately 10-30 mm in the larvae or juvenile stage to approximately 60-80 mm or more in its adult stage, for example. It will again be further appreciated that a virtually infinite variety of fish and other marine life of varying size may be sampled and monitored by implementing an organism evaluation system 20 according to aspects of the present invention, perhaps being simply scaled up or down or otherwise being modified in one or more respect to suit the particular context, all such variations being encompassed by the present invention.

With continued reference to FIG. 21, the block diagram shows the exemplary embodiment of the organism evaluation system 20 according to aspects of the present invention as again generally comprising a sorting section 31 configured in fluid communication with a waterway W so as to obtain and process a fluid flow as a subset of the overall flow in the waterway W and pass such flow along to a velocity control section 51 configured to regulate the flow from the waterway W before delivering such subset of the overall flow to the shepherding section 81, again, more about which is said below. The velocity control section 51 is shown as passing a portion of the flow to the shepherding section 81, or more precisely as having that portion of the flow through the velocity control section 51 having one or more marine sample(s) being acquired by the shepherding section 81, with the remaining flow through the velocity control section 51 being returned to the waterway W. Alternatively, as represented by the dashed lines in FIG. 21, a portion of the flow not containing any sample(s) may simply be diverted around the shepherding section 81 and into the flow normalizing section 100 upstream of the viewing section 120 and/or diverted directly to the outlet section 180 downstream of the viewing section 120. Alternatively, any flows from the waterway W directed into the inlet flow normalizing section 100 or the outlet section 180 may be sourced from a piping or other such network other than the velocity control section 51 altogether, or any combination thereof. Relatedly, it will be appreciated that a variety of means for acquiring and passing along a fluid sample, static or dynamic and now known or later developed, may be employed without departing from the spirit and scope of the present invention, such that the illustrated arrangement is to be understood as merely exemplary of aspects of the invention and non-limiting. The flow normalizing section 100 is downstream of and in fluid communication with the velocity control section 51 and/or the shepherding section 81 for the purpose of slowing and/or rendering more laminar the fluid flow as it enters the viewing section 120 configured for passing the flow therethrough and obtaining image data thereof, particularly relating to any sample(s) within the flow. More particularly, in the exemplary embodiment, the viewing section 120 comprises an illuminator 150 for providing lighting to the viewing section 120, an optical system 160 for actually acquiring image data as would a camera or camera-like device, and an imager 170 for processing or manipulating the image data from the optical system 160. It will be appreciated that throughout when a "camera" is discussed as being the "optical system 160" or equipment that any such device, whether "off the shelf" or proprietary, may further include imaging capability, that is, the ability to capture and manipulate image data with sufficient frame rate and resolution, such that in fact the optical system 160 and the imager 170 may be a single device in the form of a "camera" or the like. From the viewing section 120 the fluid flow proceeds through the outlet section 180 to a flow and sample collection container C, from which it will be appreciated that the fish or other marine life sample(s) obtained via the organism evaluation system 20, and the shepherding section 81 particularly, may be transported and relocated or eradicated as desired, it being appreciated that in any such context the shepherding section 81 fundamentally serves as a separator or a means of separating out a portion of a flow and/or any organisms or other sample(s) therein. Further regarding the organism evaluation system 20, and the viewing section 120 specifically, there is shown a separate image capture and processing device 210 (hardware and software) in communication with the viewing section 120, which device 210 is configured for taking the image data from the imager 170 and further processing the data for analysis. The image capture and processing device 210 may be any computer or processor or computing or processing device now known or later developed and may be wired or wirelessly connected to the viewing section 120, or may be incorporated into the viewing section 120, and the imager 170 specifically, again for the purpose of acquiring and processing the image data obtained by the optical system 160. Moreover, the entire viewing section 120 may be a proprietary and/or unitary device or may be comprised of one or more "off the shelf" components operably connected and configured according to aspects of the present invention, such as, for example, employing a digital camera as the optical system 160 and outputting image data from such camera using its high-speed interface such as SDI (Serial Digital Interface), USB 2 or 3, HDMI, or other appropriate interface to a computer, now known or later developed, configured to operate as the imager 170 and image capture and processing device 210, or the viewing section 120 may be some combination thereof. Such computer may further have installed and run the counting algorithm 214 and/or identification algorithm 216, or such algorithm(s) 214, 216 may be configured to operate on a separate computer or computing device. Ultimately, those skilled in the art will appreciate that the components of the viewing section 120, namely, the illuminator 150, the optical system 160, and the imager 170, and the related image capture and processing device 210 and algorithm(s)

214, 216 may be configured in a variety of ways in one or more devices without departing from the spirit and scope of the present invention, such that it is to be understood that the particular arrangement shown in FIG. 21 and elsewhere herein is merely illustrative of features and aspects of the present invention and non-limiting. Specifically, it will be appreciated that the image capture and processing device 210 and counting and identification algorithm(s) 214, 216 may be physically configured within the organism evaluation system 20 or not but are nevertheless components of the overall system 20 as represented by the block diagram of FIG. 21. Furthermore, any of the components of the system 20 may or may not be integral or packaged in a unitary way without departing from the spirit and scope of the invention.

Figure 22:
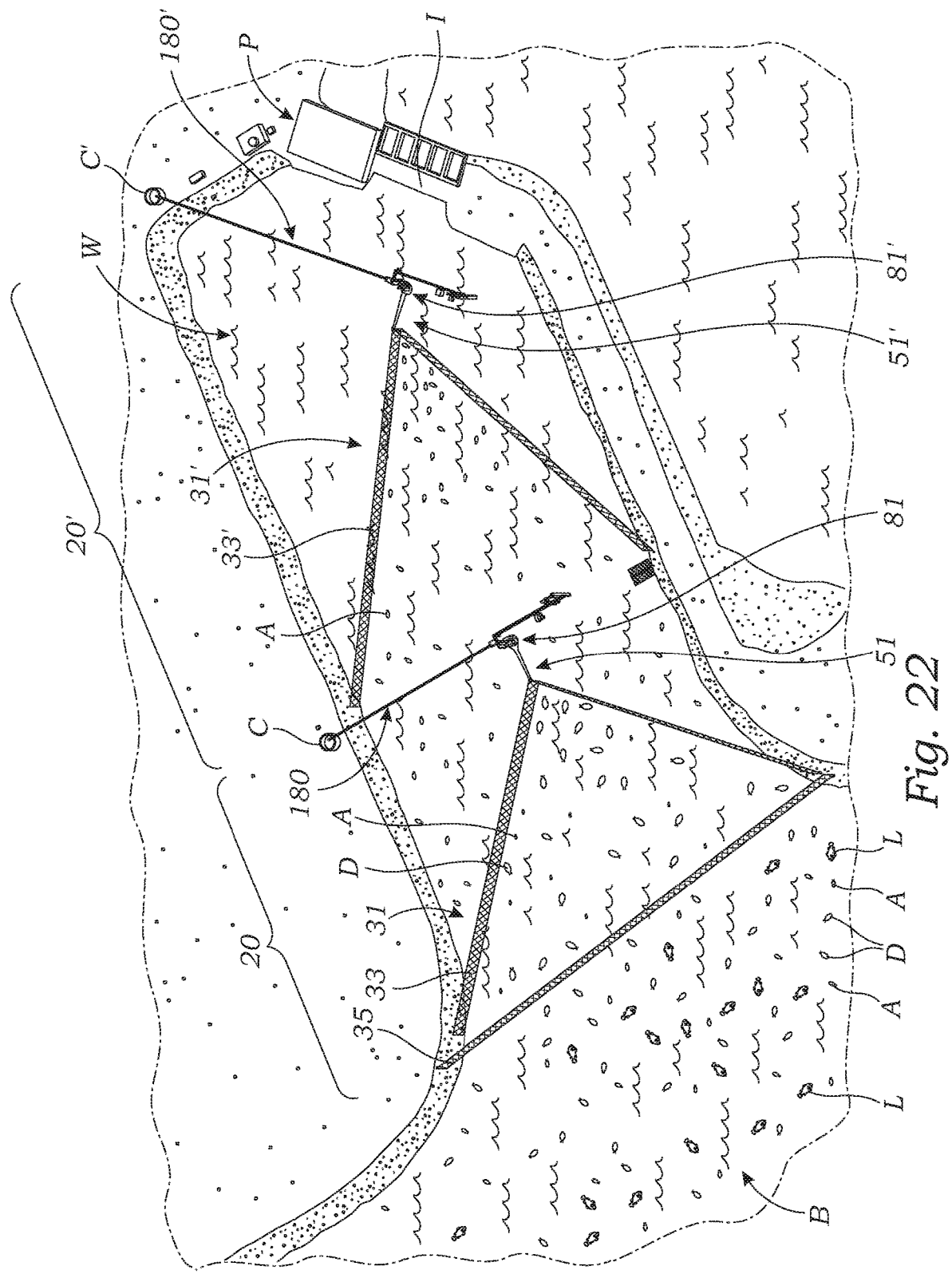
FIG. 22 is a schematic perspective view of multiple organism evaluation systems as in FIG. 21 installed in series in a waterway upstream of a pumping facility, in accordance with at least one embodiment.

Referring next to FIG. 22, there is shown a schematic perspective view of multiple organism evaluation systems 20, 20' installed in series in a waterway W upstream of a pumping facility P. As a threshold matter, it is noted that the waterway W is shown as a channel or inlet off of a larger body of water B, which may be a river, lake, ocean, reservoir, bay or forebay, or any other such standing or flowing water. It will be appreciated that depending on the type and characteristics of the body of water B and a number of related factors (e.g., water chemistry and temperature, depth, etc.), the flow characteristics in such body of water B and within any adjoining waterway W may vary considerably. Accordingly, in exemplary embodiments, any such system 20, 20' may be integrated with a range of water parameter measurement devices distributed strategically throughout the body of water B or otherwise positioned to monitor or collect data on various environmental parameters. Generally, in such contexts, relatively high and/or turbulent flows may be seen, particularly in narrowing channels or waterways B where the water may "funnel," which it will be appreciated presents risks and challenges for any marine life in such waterways W, particularly where there are collection or intake points, the concern being impingement or entrainment of such fish or other marine life. That is, the problem or challenge is water approach velocities that exceed survivability thresholds for larvae, juvenile, small, fragile, and some endangered fish and other marine life. These realities and the existence of other dangers including predatory fish and the further downstream pumping facility P itself set the stage for the problem to be solved of how to effectively account for such marine life and/or shepherd such marine life away from such dangers while allowing the desired operation of the pumping facility P. As such, there again is proposed one or more organism evaluation system(s) 20, 20' positioned within the waterway W to both account for and shepherd away any marine life present. In a bit more detail, it is first observed that in the relatively larger body of water B there may be present small-sized fish A, medium-sized fish D, and large-sized fish L. Those skilled in the art will appreciate that the large fish L may prey upon the small and medium fish A, D and further that the medium fish D may also prey upon the small fish A, depending on the species, etc. One aspect of the present invention, then, is to provide for sorting and segregating such fish A, D, L by size to address the predation concern and facilitate quantifying and/or identifying and/or shepherding such fish A, D, L systematically within the one or more organism evaluation system(s) 20, 20'. As shown in FIG. 22, more particularly, a first organism evaluation system 20 has effectively a first sorting section 31 comprising a two-stage screen 33, 35 both spanning the waterway W. An outer threshold screen 35 spans the entrance to the waterway W and is configured to effectively allow the small- and medium-sized fish A, D to pass through it into the waterway W while blocking the larger-sized fish L, thus keeping the larger fish L in the body of water B and away from the small- and medium-sized fish A, D within the waterway W. The primary screen 33 associated with the first sorting section 31 is configured to also span the waterway W downstream of the threshold screen 35 and to effectively allow the small-sized fish A to pass through it further into the waterway W while blocking the medium-sized fish D, thus keeping the medium fish D away from the small fish A and effectively isolating the medium-sized fish D, more about which is said below. As shown schematically, the primary screen 33 is formed in a somewhat V-shaped configuration to funnel the medium-sized fish D toward the substantially central first velocity control section 51 and related downstream first shepherding section 81. Similarly, the second organism evaluation system 20' in series within the waterway W downstream of the first monitoring system 20 includes a primary screen 33' that does not even allow the small-sized fish A to pass through it and thus isolates the small fish A within the waterway W just as were the medium-sized fish D by the first organism evaluation system 20 and first sorting section 31 specifically. The second primary screen 33' again is formed in a somewhat V-shaped configuration to here funnel the small-sized fish S toward the substantially central second velocity control section 51' and related downstream first shepherding section 81', again more about which is said below. Those skilled in the art will appreciate that the screens 35, 33, 33' may be configured in any appropriate manner and construction now known or later developed and should preferably span the depth of the waterway W effectively from substantially at or near the bottom thereof to a location above the actual or highest expected water level or surface. Where such screens 35, 33, 33' are employed in series, it will be further appreciated that the sizes of the openings therein would be serially decreased to allow only smaller and smaller fish through and thereby sort or segregate the fish by size as herein described. Accordingly, each shepherding stage is optimized for the size/strength of fish guided to that stage by the screens 35, 33, 33'.

Figure 23:
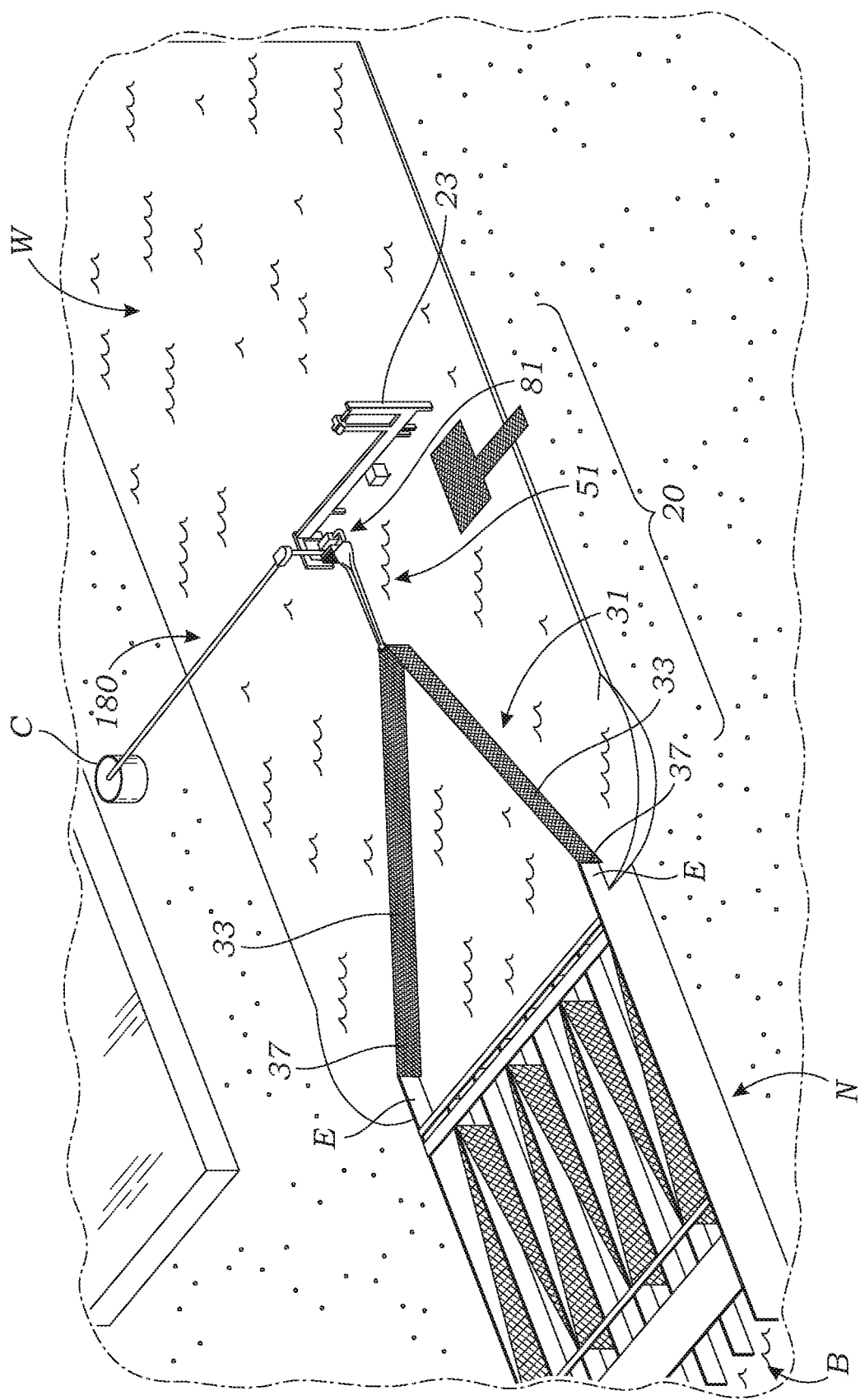
FIG. 23 is a schematic perspective view of a still further alternative exemplary organism evaluation system installed in a waterway downstream of a screening facility, in accordance with at least one embodiment.

Turning to FIG. 23, there is shown a schematic perspective view of an alternative organism evaluation system 20 installed in a waterway W downstream of a screening facility N fed by a larger body of water B. A single organism evaluation system 20 is installed within a channel-like waterway W again upstream of a pumping facility P or the like (FIG. 22), but here as further being downstream of an existing screening facility N that it will be appreciated may serve the purpose of preventing entry of the largest fish L while allowing entry of small- to mid-sized fish A, D (FIG. 22). As a threshold matter, it will be appreciated that even though an existing upstream fish screening facility N is shown, two or more organism evaluation systems 20, 20' may still be provided downstream in series as shown in FIG. 22. And conversely, even though no fish screening facility N is shown in FIG. 22 upstream of the organism evaluation systems 20, 20', still only one organism evaluation system 20 may instead be employed. Fundamentally, those skilled in the art will appreciate that such systems or hardware may be employed in various combinations to suit a particular context or application (e.g., based on the number and kinds of fish species or other marine life expected to be present), such that the illustrated embodiments are to be understood as merely exemplary and non-limiting. With continued reference to the alternative embodiment of FIG. 23, once more, a single organism evaluation system 20 is shown installed in the waterway W such that the screen 33 of the sorting section 31 at least spans the exit E of the screening facility N such that all fish passing through the screening facility into the waterway W are contained within the sorting section 31 and thereby forced or funneled into the respective velocity control section 51 and shepherding section 81 as herein described. As shown, a support framework 23 may be installed within the waterway W to support the other components or sections of the organism evaluation system 20. Any such framework 23 and other infrastructure may be comprised of any materials and structures now known or later developed suitable to the application. Again, a number of other configurations of the organism evaluation system 20 are possible according to aspects of the present invention without departing from its spirit and scope.

Figure 24:
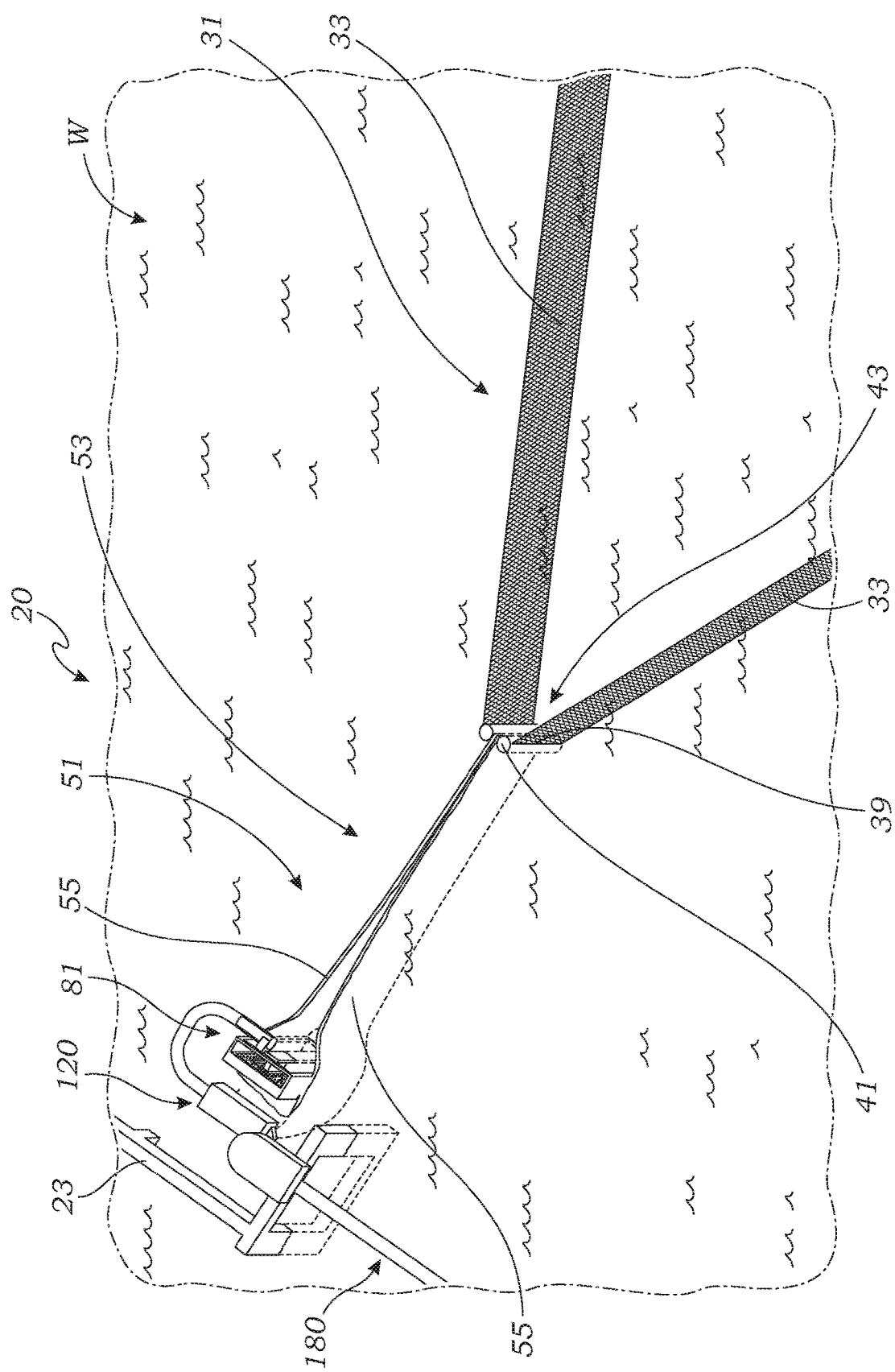
FIG. 24 is an enlarged schematic partial perspective view thereof, in accordance with at least one embodiment.
Figure 25:
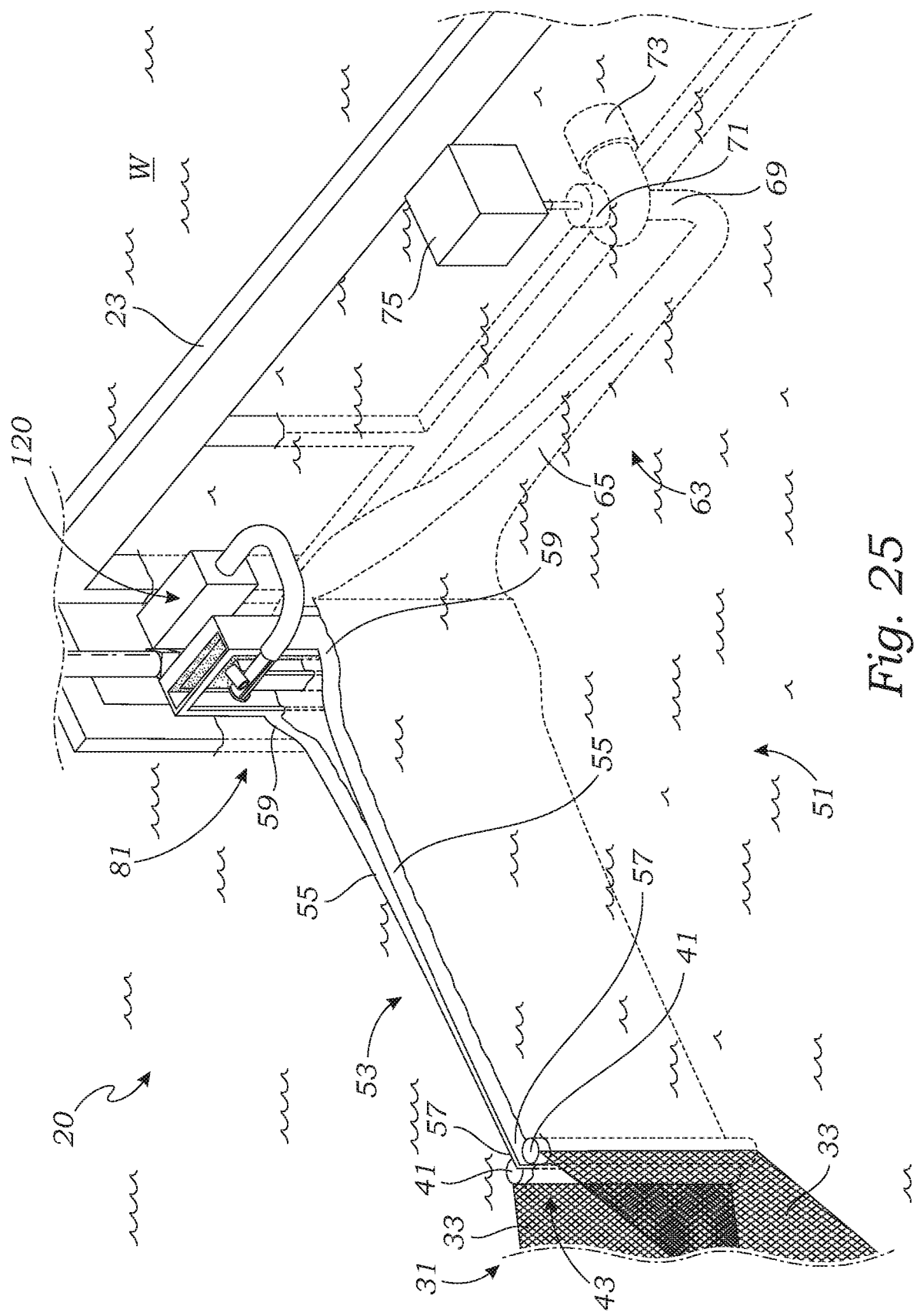
FIG. 25 is a further enlarged schematic partial perspective view thereof, in accordance with at least one embodiment.

Referring next to FIGS. 24 and 25, there are shown enlarged partial perspective views of the exemplary organism evaluation system 20 of FIG. 23 from two somewhat opposite vantage points so as to depict particularly the velocity control section 51 and related components, generally comprising a velocity control chute 53 immediately downstream of and in fluid communication with the sorting section 31 and upstream of the shepherding section and separately a velocity control pumping assembly 63 downstream of and in fluid communication with both the velocity control chute 53 and the shepherding section 81. As a threshold matter, it will be appreciated that features that are under the surface of the water in the waterway W are drawn in dashed lines, but that these structures are otherwise not hidden or disclaimed, though for simplicity, the sorting section 31 and its screen 33 are not dashed. As shown, the screen 33 may be of a mesh or other such configuration employing any appropriate materials and construction now known or later developed. Again, the screen 33 may be in a substantially V-shaped configuration across the waterway W so as to direct fish or other marine life that cannot pass through the screen 33 somewhat centrally into the velocity control section 51. Accordingly, it will again be appreciated that the screen 33 would extend vertically substantially from the bottom of the waterway W to a location above the actual or highest expected water level or surface. As illustrated, the V-shaped configuration is actually achieved by two separate sections of screen 33 that each are connected at their upstream ends 37 to or near the exit E of the screening facility N (FIG. 23) and terminate at their forward or downstream ends 39 adjacent to one another so as to form a gap or opening 43 therebetween. The downstream screen ends 39 may be anchored and the opening 43 between them may thus be defined by anchors 41 formed in the waterway W, here configured as vertical posts, may be mounted to the framework 23 or the velocity control section 51, and the velocity control chute 53 specifically, or may otherwise be secured in the desired positions to form the opening 42. In an exemplary embodiment, the locations of the anchors 41 may be shifted to adjust the size of the opening 42, or of the exit from the sorting section 31 into the velocity control section 51, as may be desirable or dictated by flow characteristics or the number and kinds of species in the waterway W where the organism evaluation system 20 is located. Relatedly, the entrance into the velocity control section 51 or the velocity control chute 53 is shown in the exemplary embodiment as being formed by opposing substantially vertical walls 55 that together effectively form a channel or isolated flow region from the rest of the main waterway W flow. As with the screens 33, the walls 55 would preferably extend vertically substantially from a location at or near the bottom of the waterway W to above the actual or expected waterway water level so as to direct all fish or other organisms entering the velocity control chute 53 toward the downstream shepherding section 81. In the exemplary embodiment, the velocity control chute walls 55 are somewhat outwardly curved downstream or are otherwise configured to be relatively closer to each other at the upstream velocity control section inlet, or the upstream wall ends 57 contiguous with the sorting section outlet or opening 42 or the downstream screen ends 39, and relatively further from each other in the region of the velocity control chute 53 where the shepherding section 81 is positioned, or in the vicinity of the downstream wall ends 59. Those skilled in the art will appreciate at a high level that such an expansion within the waterway sub-flow as caused by the geometry of the velocity control chute 53, and the walls 55 specifically, would alone effectively cause the sub-flow within the velocity control section 51 to slow and become relatively more laminar, more about which is said below. That is, the velocity control chute 53 being of increasing cross-section or volume in the downstream direction serves to slow the velocity of water with minimal turbulence. It will be appreciated that a variety of configurations and materials for the velocity control chute walls 55 now known or later developed and thus the overall velocity control chute 53 are possible according to aspects of the present invention without departing from its spirit and scope. In one exemplary embodiment, the sections of screen 33 at their downstream ends 39 may be directly mounted or attached to the upstream ends 57 of the velocity control chute walls 55, with or without the anchors 41, such that the overall flow and fish directional system operates in tandem. In the case where the locations of the ends 39, 57 and thus the size of the opening 42 may be adjusted, it would follow that where the screens 33 and walls 55 are linked, movement of one would affect movement of the other, such that widening or narrowing the opening 42 of the sorting section 31 simultaneously would widen or narrow the upstream or inlet entrance into the velocity control chute 53, again thereby affecting overall flow characteristics. In such a case, and by way of further illustration, the downstream ends 59 of the velocity control chute walls 54 may be hinged or able to flex or otherwise configured to accommodate relative movement of the upstream wall ends 57. Alternatively, the walls 54 themselves may be sufficiently flexible to allow for relative movement of the adjacent upstream ends 57 even without any hinge at the downstream wall ends 59.

With continued reference particularly to FIG. 25, in the exemplary embodiment the velocity control section 51 is shown as further comprising downstream of the velocity control chute 53, or of the downstream ends 59 of the velocity control chute walls 54, and of the shepherding system 81, a velocity control pumping assembly 63. The pumping assembly 63 generally comprises a closed fluidic channel 65 that is in fluid communication at a first end 67 with the velocity control chute 53 and at an opposite second end 69 with a pump 71. The pump 71 then includes a discharge 73 for discharging water from the fluid channel 65 through the pump 71 back into the waterway W. The pump 71 in cooperation with all related piping is configured downstream of and in fluid communication with the velocity control chute 53 to further contribute to the control of the flow rates and flow characteristics in the velocity control chute 53. As a threshold matter, those skilled in the art will appreciate that a variety of piping configurations and geometries are thus possible according to aspects of the present invention, such that the illustrated arrangement is to be understood as merely exemplary and non-limiting. By way of further example, while the velocity control pumping assembly 63, and the fluidic channel 65 particularly, is shown as being transverse to the main waterway W flow and to that of the velocity control chute 53, such is not necessary and the velocity control chute 53 and the velocity control pumping assembly 63 may instead be substantially in-line as illustrated in the alternative embodiments of FIGS. 26 and 27, or in any other spatial relationship. Fundamentally, according to aspects of the present invention, key water parameters are controlled in the velocity control section 51 (a micro environment) that is contained within a larger waterway W (a macro environment) that to some extent cannot be controlled; by isolating the flow in this way a more controlled environmental system can be created. More particularly, the aim as it relates to the fish or other marine life or organism samples ushered into the velocity control section 51 from the sorting section 31 is to control or regulate the approach velocity into the fish shepherding section 81 so as to minimize stress or harm to the fish or other organisms through entrainment or impingement, which will be further appreciated from the below discussion in connection with FIGS. 26 and 27. A related consideration is the velocity at the opening 42 from the sorting section 31 into the velocity control section 51 as discussed above—it will be appreciated that the flow at the entrance to the velocity control chute 53 being generally greater than the ambient conditions found in the macro environment of the waterway W, a natural result of such a narrowing of the flow before the expansion and slowing toward the shepherding section 81, will tend to draw the fish into the velocity control chute 53. Accordingly, an adjustable width inlet chute 53 as above-described could be helpful in certain applications, providing increased flexibility for a wider range of flow velocities found in the ambient conditions and/or desired for the velocity control chute 53. In further detail regarding the effective closed loop control system within the velocity control section 51 resulting from the cooperation of the velocity control chute 53 and the velocity control pumping assembly 63, the closed fluidic channel 65 feeds the pump 71 that draws water through the velocity control section 51. Thus, by running the pump faster or slower, or "opening it up" versus "throttling it back," the result is to increase or decrease the flow rate through the velocity control chute 53, the pump 71 in essence acting as a gate or throttle for the flow and thus being capable of regulating the flow within the velocity control chute 53, the geometry of the chute 53 then further contributing to the flow dynamics and cooperating to cause the flow to be relatively more laminar at any flow rate. A controller 75 is shown as connected above the pump 71 out of the water, though it will be appreciated that the controller 75 could be in a sealed housing under the water or integrated or packaged with the pump 71 or could be further removed, located on the support framework 23 or even on shore or at some other location, and being either wired or wirelessly connected to the pump 71 and other control components such as flow sensors and the like. In one exemplary embodiment, though not shown, the velocity control chute 53 flow rate, or the shepherding section approach velocity, may be measured by a pitot tube (not shown) or other fluid velocity measurement device now known or later developed in proximity to the shepherding section 81. Accordingly, a "PID" (Proportional, Integral, Derivative) control scheme will run the pump 71 at whatever speed is required to maintain the proper set-point value for the shepherding section 81 water approach velocity, whereby even as ambient or nominal flow and other conditions change within the overall waterway W, the proper velocity at the shepherding section 81 will be maintained. It will be appreciated by those skilled in the art that a range of desired flow rates or approach velocities is possible according to aspects of the present invention based on a number of factors, including but not limited to the size or scale of the system 20 and the kind and number of fish or other marine organisms that are to be handled through the system 20, such that the particular arrangement of the system 20 shown and described is to be understood as merely illustrative and non-limiting. Fundamentally, the water approach velocity at the shepherding section 81 must be below the threshold that could cause the size range of fish expected within the system 20 to be either impinged or entrained.

Referring still to FIGS. 24 and 25, other considerations for the design and configuration of such an organism evaluation system 20 according to aspects of the present invention relate to "attractants" of various kinds that may be placed strategically throughout the system to first encourage the fish or other organisms into the velocity control section 51, and the chute 53 specifically, and then from the chute 53 into the shepherding section 81, more about which is said below again primarily in connection with FIGS. 26 and 27. In the context of the velocity control section 51, and particularly the transition from the sorting section 31 and related screens 33 into the velocity control chute 53, entrance is designed to be "attractive" to fish, using such things as: simulated "green grass" as would be seen on a river or lake shoreline; appropriate intensity and color of lighting to not spook the fish; a "safe" environment could be simulated, depending on ambient conditions, such as during the daytime with bright sunlight the fish might tend to seek out a darker, safer-appearing location. Also during the daytime an automated fish pellet dispenser (not shown) may be provided that detects the presence of fish in order to manage dispensing of food, and at nighttime laser light can be used to simulate surface prey such as fireflies. Any and all such "attractants" may be employed at the entrance to and/or within the velocity control chute 53 again to encourage the fish forward in the system 20. Those skilled in the art will appreciate that a variety of "attractants" may be employed in various combinations with any such organism evaluation system 20 according to aspects of the present invention to suit particular applications.

Figure 26:
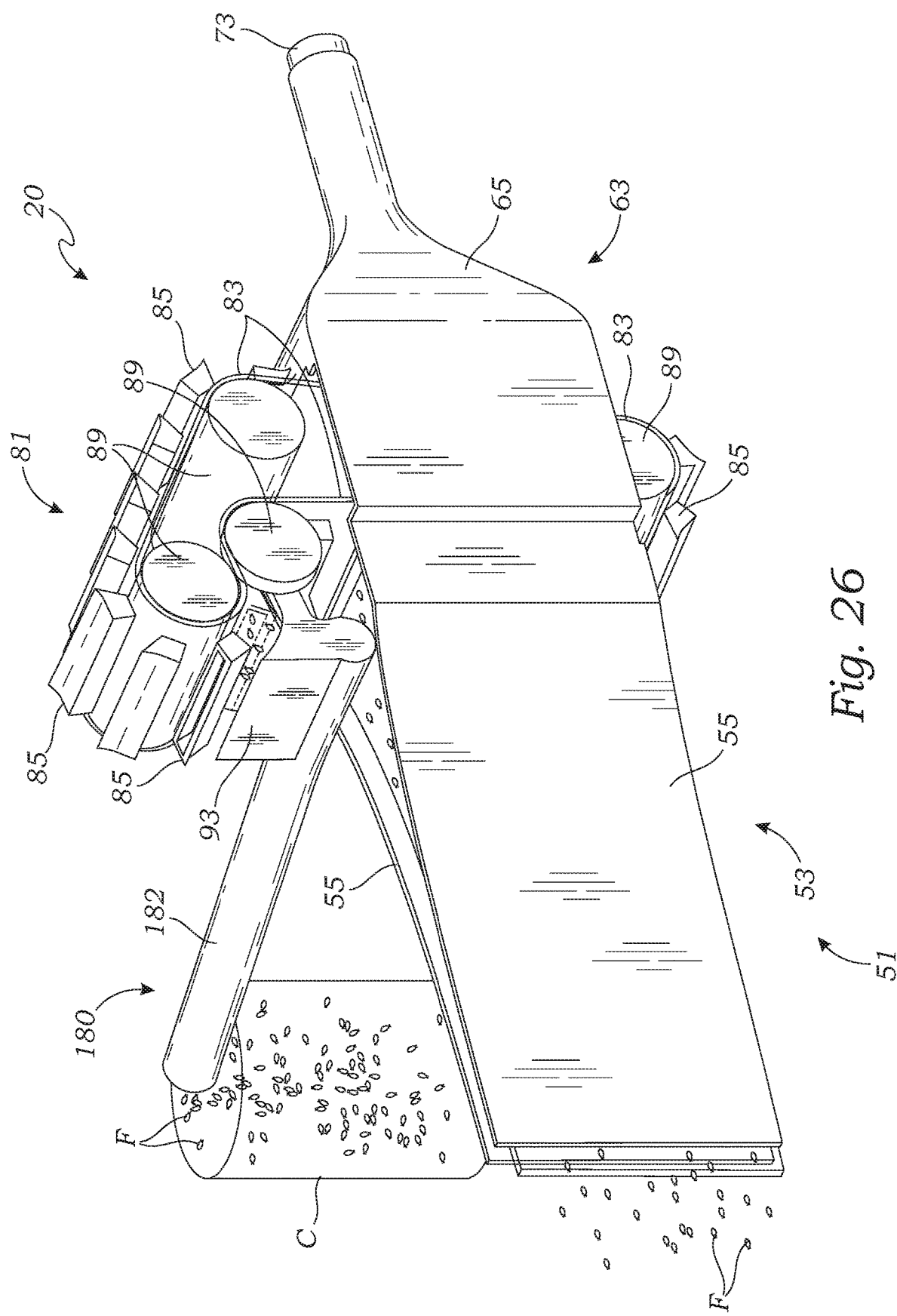
FIG. 26 is a schematic partial perspective view of a still further alternative exemplary organism evaluation system, in accordance with at least one embodiment.

Turning now to FIG. 26, there is shown a schematic partial perspective view of an alternative organism evaluation system 20 according to aspects of the present invention, here generally comprising a velocity control section 51 and a shepherding section 81. The velocity control section 51 again generally comprises a velocity control chute 53 upstream of the shepherding section 81 and a velocity control pumping assembly 63 downstream of the shepherding section 81. The velocity control chute 53 again includes opposite curved or tapering walls 54 that transition downstream to the fluidic channel 65 of the pumping assembly 63, where here is effectively straight back or downstream of and in-line with the velocity control chute 53 and then discharges back into the water flow from discharge 73. Again, a variety of such configurations of the velocity control section 51 are possible according to aspects of the present invention. In the system 20 of FIG. 26 no upstream sorting section 31 (FIGS. 21-25) is shown for simplicity, though such would be in fluid communication with and feed the inlet of the velocity control chute 53. Further, here, no viewing section 120 is shown either; such may be incorporated in the outlet section 180 or may simply not be employed, in which case the system 20 serves primarily simply as a shepherding system—i.e., a system for collecting and relocating fish F and other marine life. Regardless, whenever a shepherding section 81 is employed and irrespective of the other components in the system 20, the fish shepherding section 81 is generally configured to relatively gently lift fish F up out of the ambient flow into areas of protection before they reach areas of danger such as the intakes of large pumping facilities P (FIG. 22). A variety of mechanisms for collecting the fish F from the water flow are possible, illustrative ones of which are disclosed herein; it will be appreciated that any such mechanism now known or later developed may be employed in an organism evaluation system 20 according to aspects of the present invention without departing from its spirit and scope. In the exemplary embodiments of FIGS. 26 and 27, a somewhat vertically-oriented conveyor 83 with spaced-apart buckets 85 installed thereon is configured on a plurality of rollers 89 in order to, upon activation and movement of the conveyor 83, "scoop" the fish F into the buckets 85 and lift them out of the flow. As the buckets 85 pass over or between one or more rollers 89 near the top of the shepherding section 81 they are oriented or tipped sufficiently downwardly to empty or "dump" their contents into a receptacle 90 that then ushers the water and fish F down an outlet section 180 here configured as an outlet pipe 182 and into a collection container C for storing and eventually relocating or eradicating the fish F. The conveyor 83, buckets 85 and rollers 89 may be made of any appropriate metal, plastic or other such materials now known or later developed. Any such components, and particularly the conveyor 83, may be perforated or have openings throughout to allow the passage therethrough of water. To encourage the fish F toward the shepherding section 81, once again, lighting and other effects along the velocity control chute 53 such as to simulate green grass or ambient conditions may be employed. It will be appreciated that while the shepherding section 81 is configured to relatively gently lift the fish F, any such handling of the fish F will still be stimulating to them to some extent, and thus the shepherding section 81 may effectively serve as or function similarly to the various stimulation sections 80 disclosed herein. It will be further appreciated that in some embodiments both a stimulation section 80 and a shepherding section 81 may be used in the same system 20, in any order or location within the system 20. Or as noted above the same device may effectively serve the purpose of or combine the features of a stimulation section 80 and a shepherding section 81. And in still other embodiments an organism evaluation system 20 according to aspects of the present invention may include neither a stimulation section 80 nor a shepherding section 81. Again, those skilled in the art will appreciate that a variety of systems 20 and related sub-systems or sections in a range of combinations are possible without departing from the spirit and scope of the invention.

Figure 27:
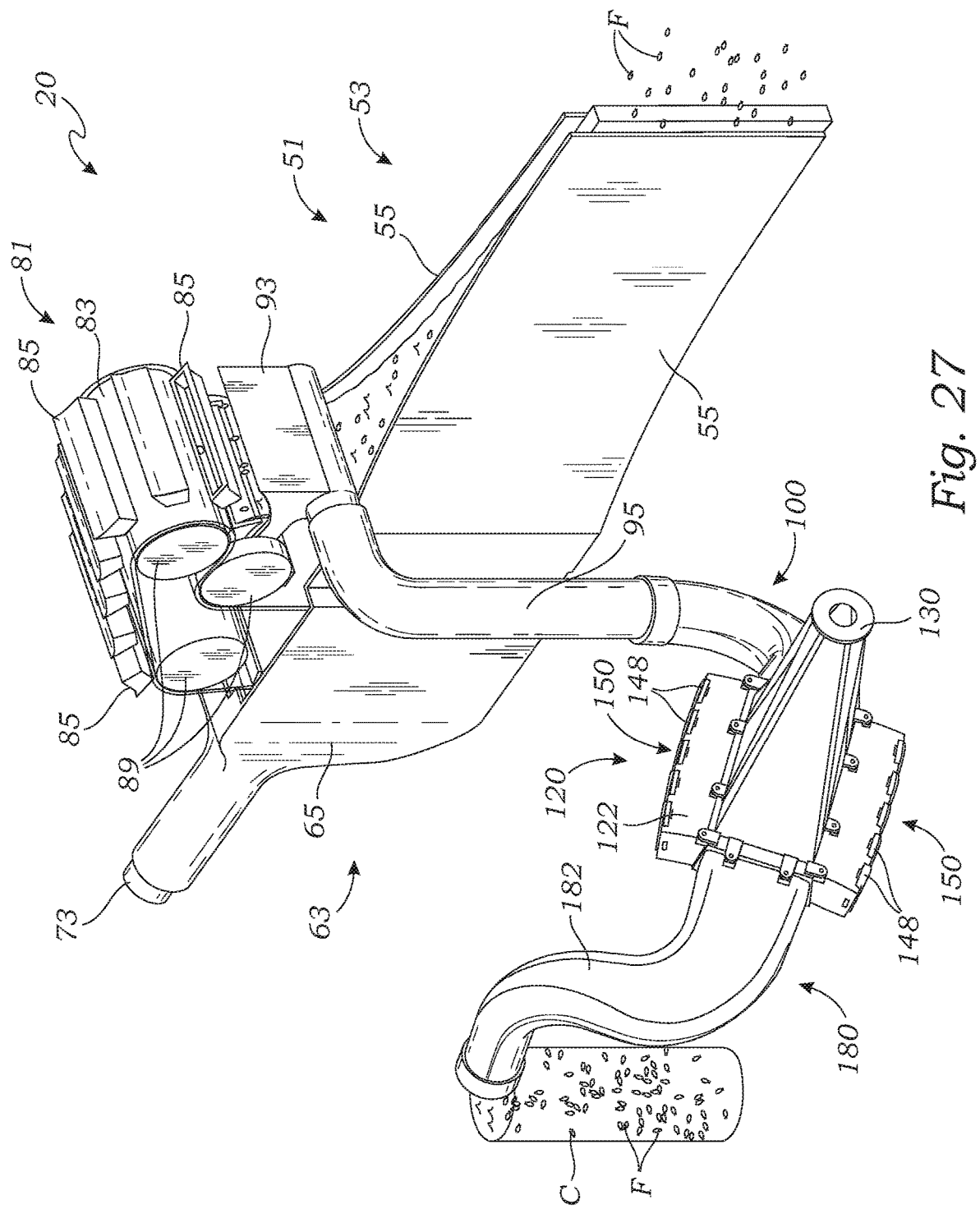
FIG. 27 is a schematic partial perspective view of the organism evaluation system of FIG. 26, now with a distinct viewing section installed downstream of the shepherding section, in accordance with at least one embodiment.

Referring next to FIG. 27, there is depicted schematically a further alternative exemplary organism evaluation system 20 according to aspects of the present invention, here being similar to that of FIG. 26 as again generally comprising a velocity control section 51 and a shepherding section 81, with the velocity control section 51 having a velocity control chute 53 upstream of the shepherding section 81 and a velocity control pumping assembly 63 downstream of the shepherding section 81. Once more, no upstream sorting section 31 (FIGS. 21-25) is shown for simplicity. However, here, most notably, a viewing section 120 is shown as being installed in or more precisely upstream of the outlet section 180, between the receptacle 90 and the outlet section 180. While the viewing section 120 for collection of image data regarding the flow and any fish F therein is thus shown as being downstream of and outside of both the velocity control section 51 and the shepherding section 81, it will be appreciated that any such viewing section 120 may also be within the velocity control section 51 or downstream thereof, whether or not there is a shepherding section 81. That is, in alternative embodiments, the viewing section 120 may simply be a pass-through device or system within a water flow through which a sample is passed so that image data can be obtained, with the sample then simply returned to the same water source. Furthermore, image data can be obtained via a viewing section located or incorporated within the velocity control section 51 with the sample, or more particularly fish F from the flow, still captured within a downstream shepherding section 81 for collection and/or relocation and/or eradication. When the shepherding section 81 is employed as shown previously in FIG. 26 and here in FIG. 27, it once more may comprise a somewhat vertically-oriented conveyor 83 with spaced-apart buckets 85 installed thereon and configured on a plurality of rollers 89 in order to, upon activation and movement of the conveyor 83, "scoop" the fish F into the buckets 85 and lift them out of the flow and eventually dump them into a receptacle 93; alternatively, after being temporarily removed from the main water flow via the shepherding section 81 and passed through the viewing section 120, the flow may be then be directed back into the main waterway rather than into a collection container C as shown. Regardless, here, downstream of the receptacle 93 there is provided an exit pipe 95 to direct the flow away from the receptacle 93; accordingly, as illustrated, such exit pipe 95 may turn or be directed somewhat downwardly to allow a gravity feed effect toward the viewing section 120 that then ushers the water and fish F therethrough and out an outlet section 180 here configured as a curved outlet chute 182 directed to the collection container C for storing and eventually relocating or eradicating the fish F. In the schematic representations of the system 20 of FIGS. 22 and 23, the outlet section 180 is substantially straight. Those skilled in the art will appreciate that any such geometry or configuration of the outlet section 180 and the outlet chute 182 specifically is possible, whether now known or later developed. Fundamental to the organism evaluation system 20 according to aspects of the present invention is the capability to self-document or to some extent, whether automated or semi-automated, count and/or identify fish F passing through the system 20. As the system 20 operates per the exemplary embodiment, the fish F are directed into the velocity control section 51, are then taken out of the flow via the shepherding section 81, and are passed into the viewing section 120. It will be appreciated that with the water in the waterway W (FIGS. 22-25) flowing substantially continuously and so with the organism evaluation system 20 itself then operating substantially continuously as well, a substantially continuous set of data regarding the fish F may thus be obtained via the viewing section 120, which would be representative of effectively the real-time conditions within the waterway W and particularly of the number and/or type of fish F, more about which is said below. Further ancillary data may also be collected intermittently or substantially continuously as desired, such as water temperature and chemistry.

Figure 28:
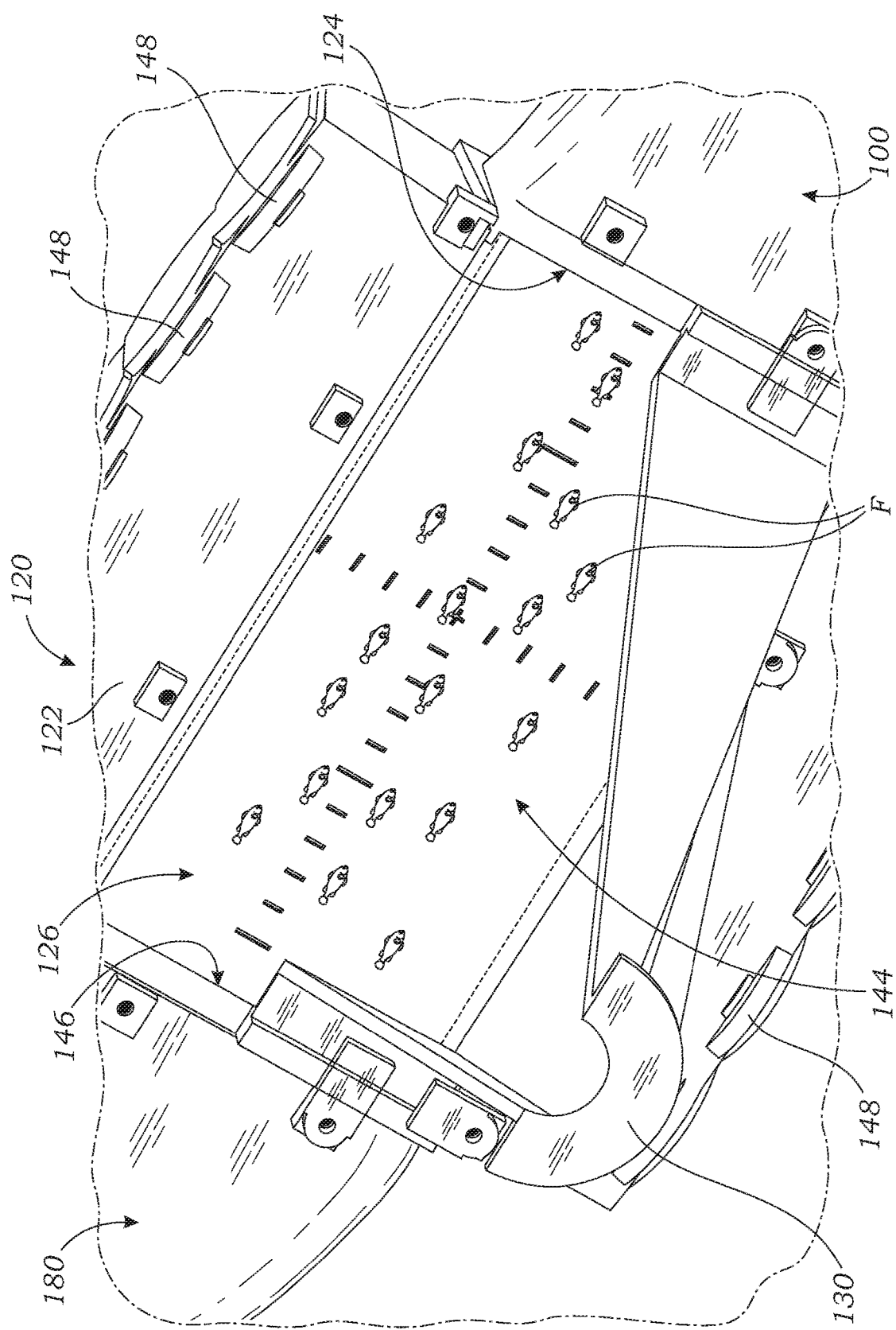
FIG. 28 is an enlarged schematic partial perspective view of the viewing section thereof, in accordance with at least one embodiment.
Figure 29:
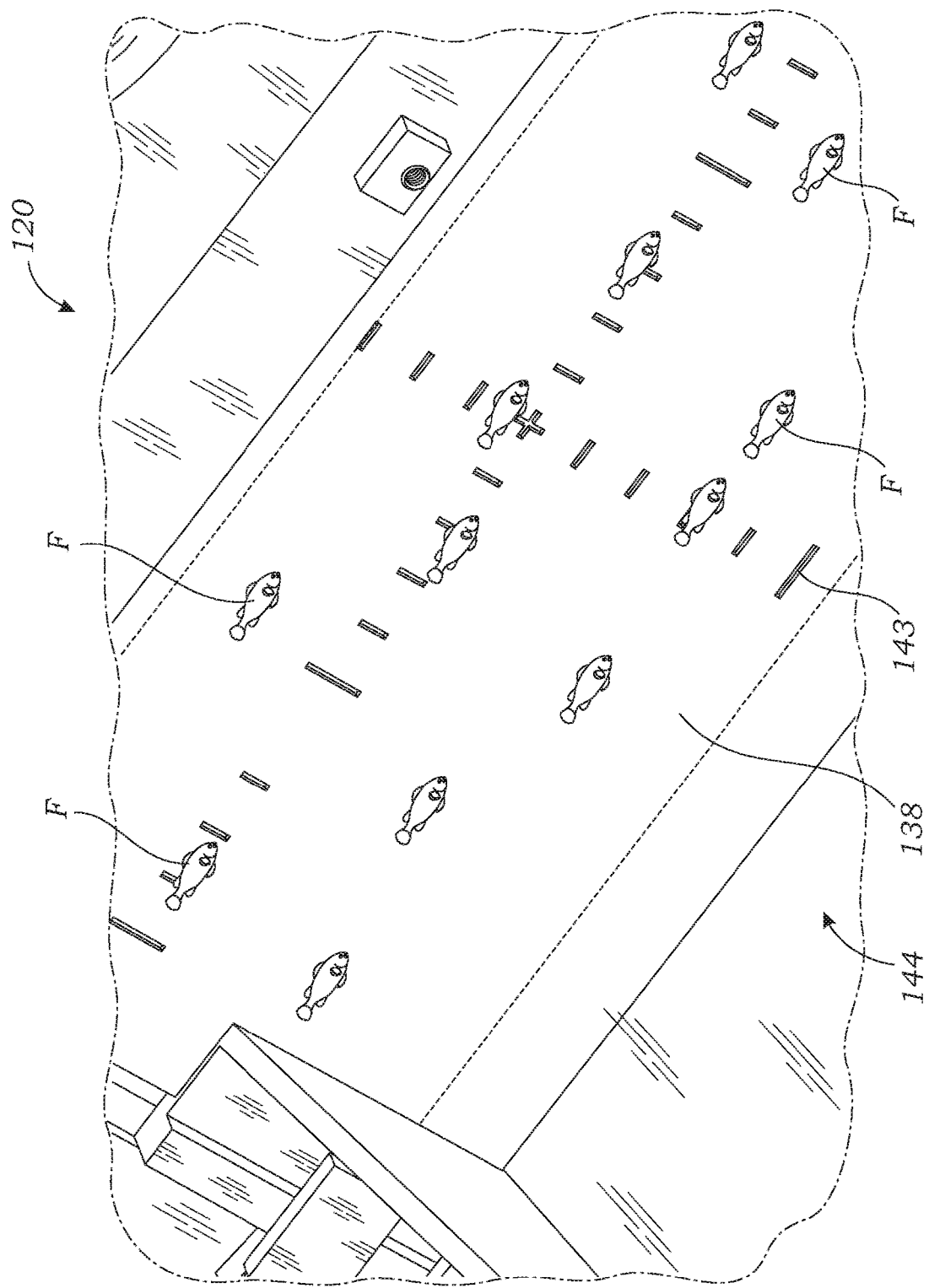
FIG. 29 is a further enlarged schematic partial perspective view of the viewing section thereof, in accordance with at least one embodiment.

With continued reference to FIG. 27 and now further reference to the enlarged sectioned views of the viewing section 120 of FIGS. 28 and 29, attention is turned to the principles of operation and related features of the viewing section 120 in the context of the present organism evaluation system 20. Generally, the viewing section 120 comprises a viewing section body 122 with an optical system mount 130.

The illuminator 150, the optical system 160, and the imager 170 (FIG. 21) are not shown for simplicity, though at least the illumination ports 148—five on each side of the viewing section body 122 in the exemplary embodiment wherein LEDs or the like may be installed so as to illuminate the interior cavity 126 of the viewing section 120, and the viewing port 144, specifically—are shown as being integral with the viewing section body 122, more about which is said below. Regarding the optical system 160 and the imager 170, as explained above, these may be separate or integral components and "off the shelf" or proprietary, but in the exemplary embodiment a camera (not shown) is contemplated wherein the lens would mount or be removably installed directly to or on the optical system mount 130 of the viewing section body 122 such that the lens "looks" substantially straight into the viewing port 144 shown as intersecting the optical system mount 130 and thus communicating with the body cavity 126. As also best seen in FIG. 28, in the exemplary embodiment, the body 122 effectively has a viewing section body inlet 124 coinciding with the flow normalizing section 100 and an opposite viewing section body outlet 146 coinciding with the outlet section 180, which inlet 124 and outlet 146 are each in fluid communication with the hollow interior of the viewing section 120, or the viewing section body cavity 126 specifically. The sides of the body cavity 126 and thus the viewing port 144 are formed from the viewing section body 122, the bottom by a back plate 138, and the top by a substantially clear or transparent viewing plate 136 (not shown for simplicity). Again, numerous other hardware components and configurations (geometry, means of assembly, etc.) are possible without departing from the spirit and scope of the present invention. Thus, as a threshold matter, those skilled in the art will appreciate that the viewing section 120 may take a number of forms and be positioned in a number locations and orientations within the organism evaluation system 20, such that that shown and described is to be understood as merely illustrative and non-limiting. Fundamental to the design and principles of operation of the organism evaluation system 20 is that fish are like miniature control systems and respond to particular environmental stimuli, somewhat analogous to the previous discussion relative to microorganisms. An exemplary response characteristic is that fish tend to "school up" when the appropriate environmental parameters are induced. One such parameter is geometrical, such as by providing a relatively straight and narrow flow path for the fish F to swim in, as illustrated both in connection with the velocity control chute 53, which would be more relevant if the viewing section 120 immediately followed and also separately serves a flow regulation function as above-described, and in connection with the flow normalizing section 100 that somewhat flattens as it transitions or connects to the viewing section body 122 as shown in FIG. 27; in connection with the viewing section 120 itself, and the body cavity 126 and related viewing port 144 specifically, a relatively narrow depth of field (e.g., 5% to 20% of length) may be provided relative to the optical system 160 and imager 170 (FIG. 21) to again encourage the fish to "school" or line up or orient themselves parallel to or along the flow path through the viewing section 120. It will be appreciated that by thus encouraging the fish to orient themselves in this way as they come through the viewing section 120, improved data collection is achievable, which in turn would lead to more accurate counting and/or identification by the system algorithms 214, 216 (FIG. 21). Depending on the speed or overall flow rate, the fish F may line up or "school" so as to swim into the current or flow, or so as to enter the viewing section 120 tail first as shown in FIGS. 28 and 29 with the flow going right to left, or may instead swim with the current or flow and thus toward the "surface," or so as to enter the viewing section 120 head first. Either way, with the fish F again swimming substantially parallel to the flow, a good "profile" image of each discrete fish F is more easily obtained. Accordingly, as shown in FIGS. 28 and 29, the bottom of the viewing section 120 or viewing port 144, or the side opposite the optical system mount 130, may include grid lines or other such indicia 143 helpful in calibrating or focusing the optical system 160 (FIG. 21) and making initial or general determinations about the sizes of the fish F in the sample flow. A related consideration or geometric parameter is the proximity of solid and substantially continuous surfaces that would effectively visually encourage the fish F along a particular path, here the viewing section 120 and related inlets and outlets. Other environmental parameters that would tend to encourage the fish F to "school up" or swim in a desired or predictable manner include lighting orientation, intensity, spectrum, duration, and location. Relatedly, lighting and other effects may be provided to replicate familiar environments, such as simulated organic objects like green grass, plants, etc. Fish also tend to be "skittish" and can be startled relatively easily, which can increase undesirable stress and unpredictable behavior, and so in addition to the above-described visual "calming" effects, the viewing section 150 particularly may entail a mechanically isolated design, meaning that higher frequency noise and vibration sources are essentially blocked from entering the viewing section 150 and other sensitive areas of the system 20.

Referring still to FIGS. 27-29, in a bit more detail regarding lighting within the viewing section 120, there are again shown a series of illumination ports 148 on opposite sides of the viewing section body 122 for illumination of the interior of the viewing section 120 and more particularly the viewing port 144 by housing one or more imaging light sources that collectively define the illuminator 150. Such imaging light sources 150 may be LEDs or any other such technology now known or later developed in the art. In an alternate embodiment, such light sources 150 may be contained within the viewing section 120, or incorporated or installed within a wall thereof, such that no separate illumination ports 148 in which would be installed illumination LEDs or other such light sources are required, though those skilled in the art will appreciate that such light sources at an angle may be employed in addition to any side-mounted illumination ports 148 and related imaging illumination 150. Fundamentally, side illumination light source(s) 150 may have a number of advantages in terms of image acquisition and quality. First, such an installation and method mitigates the development of shadows from fish F or other organisms moving in and through the viewing port 144, which shadows would tend to be cancelled out by the opposing illumination emitters. The arrangement also potentially increases the imaging contrast developed by the fish F within the flow in the viewing port 144, as the surfaces or bodies of the fish that are closest to the imager will tend to be darker than the surfaces that are illuminated, since the imaging equipment (not shown) is mounted on the optical system mount 130 well above the plane of the illuminator 150. Relatedly, the side-oriented illuminator 150 also mitigates the potential for light energy to be reflected into the optical system 160 and imager 170, including reflections from the various surfaces found within the viewing section's cavity opening 128, or the space between the viewing port 144 and the optical system 160 (not shown) that would be mounted above. In fact, by having the optical system 160 and imager 170 separated from the viewing port 144 and illuminator 150 by the clear viewing plate 136 (not shown), light will not bounce off of the glass or similar material because the illumination is contained in the fluid underneath the viewing plate 136. Again, each imaging light source defining the illuminator 150 may be an LED flush mounted within the viewing port 144. It will be appreciated by those skilled in the art that any shape or lens configuration or angle or again more generally any illumination technology now known or later developed may be employed.

It is here contemplated that the one or more side-mounted imaging LEDs would have relatively wide angle lenses so as to enhance the emission of relatively more uniform spatial distribution of light energy, which should generate a relatively "flat" and uniform background, as further aided by the inherent diffusing nature of the fluid itself within the viewing port 144. While the bank of illumination ports 148 and related illuminator light sources 150 on a particular side of the viewing section 120 may be spaced uniformly, by design, such may be unevenly spaced as well, such as having the light sources closer together at the marginal edges of the viewing port 144. Toward the center of the viewing port 144 it would tend to be brightest, where the light from effectively more light sources 150 would be compounded or aggregated, while toward the marginal edges where there are relatively fewer light sources to contribute to the illumination, it would tend to be relatively darker. Thus, by having a higher density or concentration, via closer spacing, of light sources at the margins, the net effect is substantially uniform or even lighting of the entire viewing port 144. The specific sizes and spacing of any imaging LEDs or the like and their number per side (again, five shown in FIGS. 27-29), are not to be taken literally or to scale or to be in any way limiting, it being appreciated that such are merely illustrative of features and aspects of the invention. Accordingly, a wide variety of other configurations and arrangements of imaging light sources, again, whether for side or angled or direct illumination or any combination thereof, are to be understood as within the spirit and scope of the invention.

Figure 30:
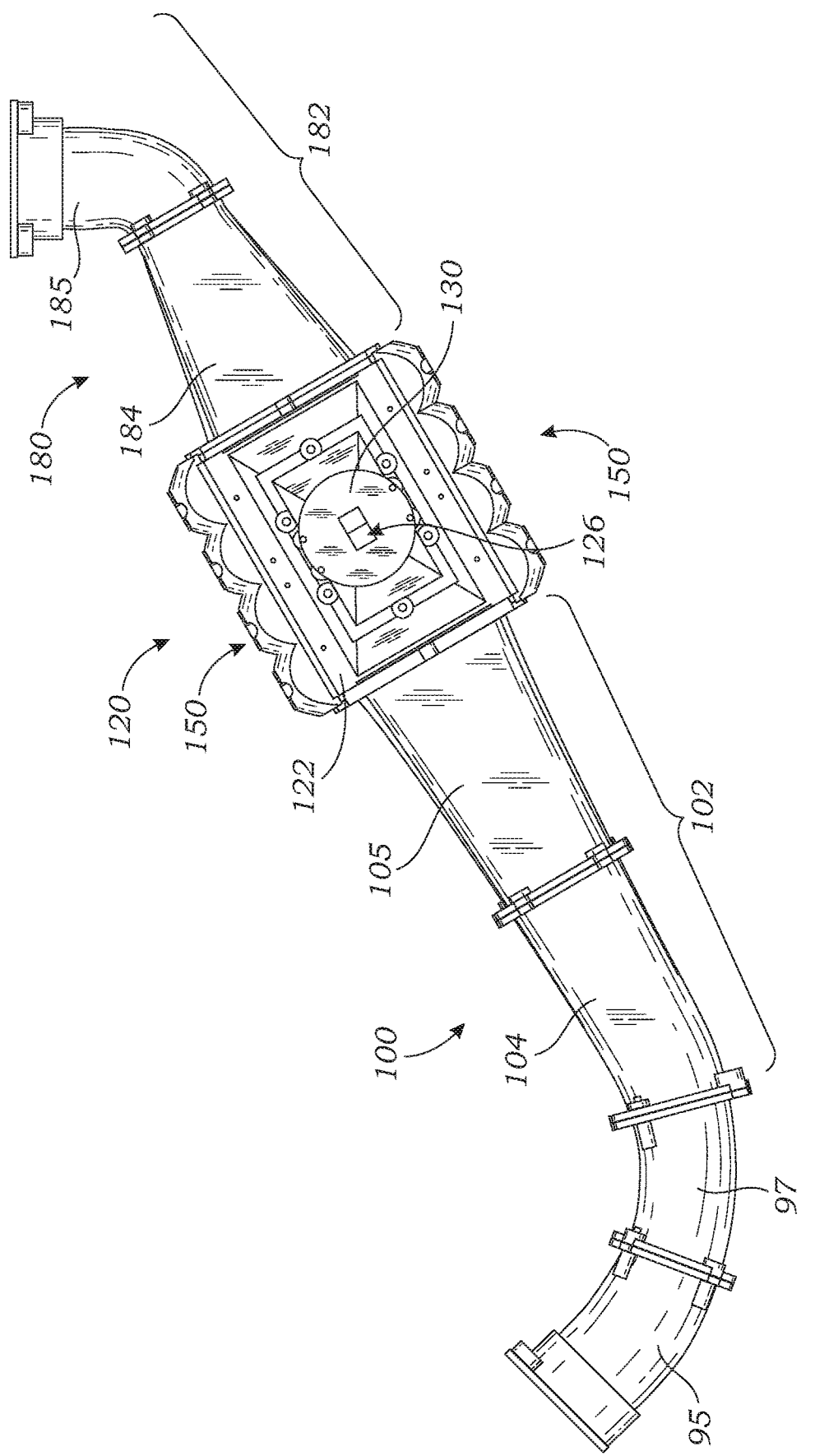
FIG. 30 is a schematic side view of an alternative viewing section, in accordance with at least one embodiment.

Turning next to FIG. 30, there is shown a schematic side view of an alternative viewing section 120 according to aspects of the present invention, here with four illumination light sources per side of the viewing section body 122 so as to again collectively define the illuminator 150. Upstream of the viewing section 120 is the flow normalizing section 100 supplied by the exit pipe 95 and downstream of the viewing section 120 is the outlet section 180 defined by an outlet chute 182. Once more, while a particular arrangement or orientation of such components or sections of the organism evaluation system 20 is shown, the invention is not so limited. And while the various pipes or chutes and even the flow normalizing section 100 itself are shown here as being comprised of multiple sections joined together as by fasteners, bonding or welding, or the like, it will be appreciated that any such components, sections, sub-assemblies or assemblies may instead be formed from more or fewer components, including being unitary, employing any appropriate materials and fabrication techniques now known or later developed, such that any illustrated assemblies are to be understood as merely exemplary in this regard and non-limiting. The same is true, for example, of the viewing section 100, here having the somewhat conical portion including the optical system mount 130 shown as being formed in two parts rather than being formed as a unitary component as shown in FIG. 27. Again, any such configurations and related materials and methods of manufacture may be employed according to aspects of the present invention without departing from its spirit and scope. Regarding particularly the flow normalizing section 100, which is downstream of and in fluid communication with the shepherding section 81, it is configured for the purpose of slowing and/or rendering more laminar the fluid flow prior to it entering the viewing section 120. Accordingly, as shown, the flow normalizing section 100 may taper or expand at least slightly toward the viewing section 100. As noted above, such flow normalizing section 100, of however many components or pieces, would be substantially continuous and smooth particularly internally where it defines the fluid flow path, which would again not only further prevent turbulence but also mitigate against any transitions or irregularities that might be stressful to fish or other organisms within the flow. As such, the flow normalizing section 100 defines a portion of the system conduit wherein the sample fluid has sufficient distance over which it is able to become relatively laminar following the relatively turbulent transitions of such fluid from the main waterway W through the velocity control section 51 and/or the shepherding section 81 (FIGS. 22-27) on its way to the viewing section 120. In the exemplary embodiment, the flow normalizing section 100 is defined by an inlet chute 102 that is itself here formed of adjoining inlet chute bodies 104, 105. An optional transition pipe 97 is connected between the exit pipe 95 from the shepherding section receptacle 93 (FIG. 27) and the first inlet chute body 104. Similarly, the outlet section 180 downstream of the viewing section 120 is configured here with a reverse taper to further slow the flow upstream thereof and then accelerate the flow downstream thereof toward the collection container C (FIGS. 21-23, 26 and 27), such outlet section 180 comprising in the exemplary embodiment an outlet chute 182 made up of two adjoining outlet chute bodies 184, 185. Once more, the interior flow conduit within the outlet chute 182 is substantially smooth to mitigate against turbulence or any disturbance of the fish or other organisms within the flow.

Figure 31:
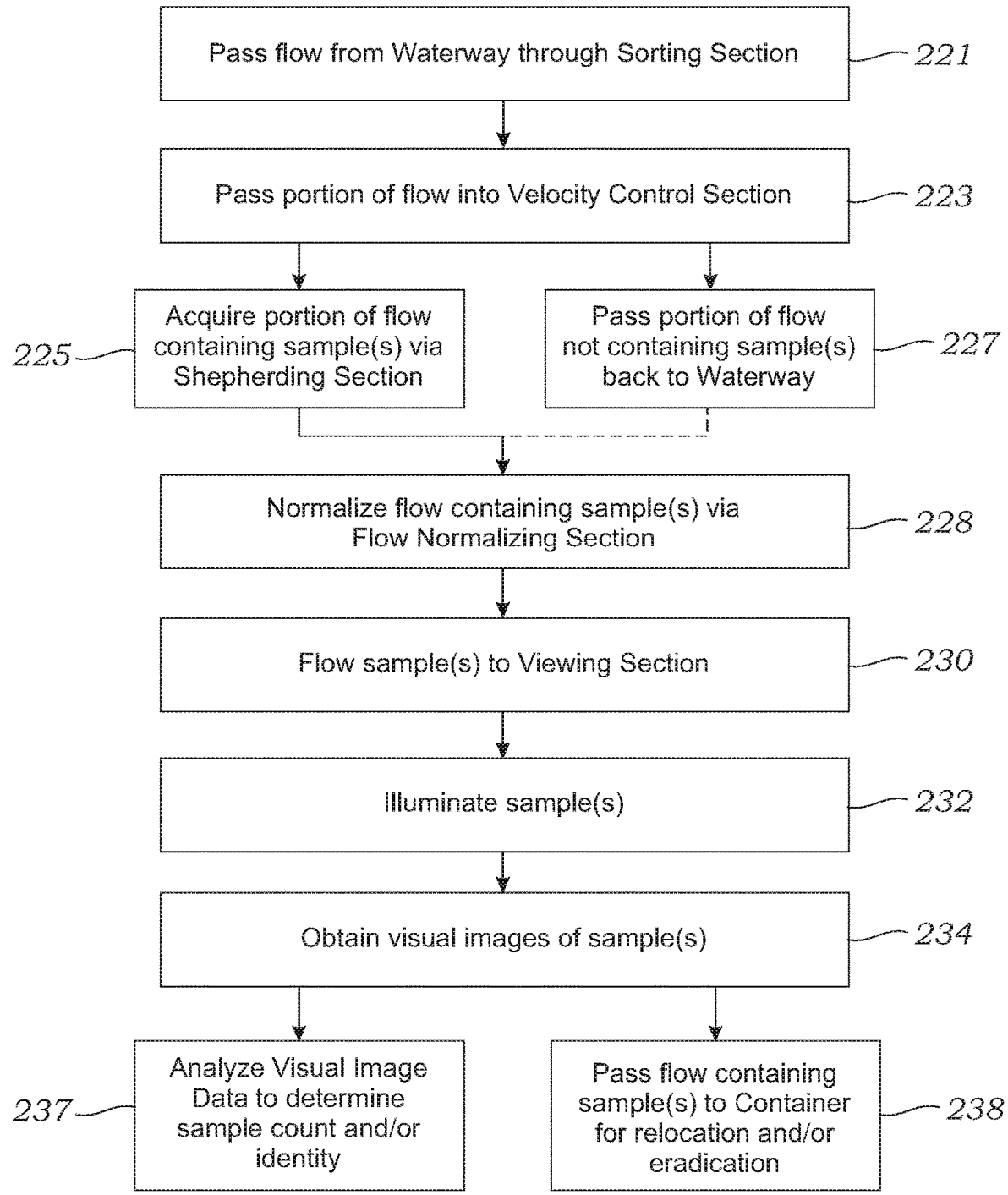
FIG. 31 is a flow chart representing use of an exemplary organism evaluation system as in FIGS. 21-30, in accordance with at least one embodiment.

Referring finally to FIG. 31, there is shown a flow chart depicting the basic operation or use of an organism evaluation system 20 according to aspects of the present invention. In use of such an exemplary system 20 as shown in FIGS. 21-30, the first step 221 is to pass the flow from the waterway W (FIGS. 22-25) through the sorting section 31 so as to separate particular fish or other marine life or organisms from other fish and organisms within the waterway W. At step 223, a portion of the main waterway flow is passed into the velocity control section 51 that is downstream of the sorting section 31. At step 225, the portion of the fluid flow containing the fish or other organisms sorted or isolated by the sorting section 31 and then passed into the velocity control section 51 is flowed into or acquired by the shepherding section 81. At step 227, any portion of the flow not containing fish or other such marine life sample(s) is typically simply passed back into the waterway W, though in alternate embodiments such flow may instead be passed to the flow normalizing section just as the sample acquired by the shepherding section 81, as represented by the dashed line in FIG. 31. At step 228, the flow is normalized or rendered relatively laminar as by flowing through the exemplary flow normalizing section 100, and then at step 230 the flow containing sample(s) passes into the viewing section 120. At step 232, the sample(s) within the viewing section 120 may be illuminated as by the illuminator 150, and then the optical system 160 in conjunction with the imager 170 may obtain visual images of the sample(s) at step 234. Finally, in terms of the general process or method of using the system 20, at step 237, the visual image data is analyzed to determine sample count and/or identity while at step 238 the flow containing the sample(s) is passed to a collection container C for storage and/or relocation and/or eradication. Those skilled in the art will once again appreciate that while particular systems and methods, including particular steps in use, are herein described, other related hardware and system configurations and associated uses, whether now known or later developed, may be substituted or employed according to aspects of the present invention without departing from its spirit and scope, such that the disclosed embodiments are to be understood as illustrative and non-limiting. More generally, it will be appreciated that there is providing an organism evaluation system 20 that enables automatic or semi-automatic logging as by counting and/or identifying fish or other marine life or organisms passing therethrough. While such system 20 is again shown as entailing a relatively stationary installation within a waterway W, it will be appreciated that any such system 20, and particularly the shepherding section 81 and/or viewing section 120 thereof, may instead be configured in a pull-behind arrangement for counting, identifying and/or shepherding (collecting and relocating) fish or other marine life in lakes and other such bodies of water. In such application, technology according to aspects of the present invention again automatically or semi-automatically counts, identifies and/or logs the fish or the like as they come through the system 20, substantially with precision and without human intervention. The benefit is more accurate and verifiable counts without compromise of the fish or other marine life being monitored.

In closing, regarding the exemplary embodiments of the present invention as shown and described herein, it will be appreciated that an organism evaluation system is disclosed and configured for determining the number and/or identity (species) of organisms within a water flow and/or whether any such organism is living. Because the principles of the invention may be practiced in a number of configurations beyond those shown and described, it is to be understood that the invention is not in any way limited by the exemplary embodiments, but is generally able to take numerous forms without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. The recitation of numerical ranges of values herein is merely intended to serve as a shorthand method of referring individually to each separate value falling within the range. Unless otherwise indicated herein, each individual value of a numerical range is incorporated into the specification as if it were individually recited herein. Similarly, all lists of values should be considered as inclusive of intermediate values unless the context indicates the contrary.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc. —for identified elements are used to distinguish between the elements, and do not indicate or imply a required or limited number of such elements, and do not indicate a particular position or order of such elements unless otherwise specifically stated.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the application should be construed as indicating any non-claimed element essential to the practice of the invention.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

The methods as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, including but not limited to advanced computer products having a display, a keyboard or other input device, and a central processor.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. An organism evaluation system for analyzing and processing organisms within a fluid flow of a waterway, comprising:
    a sorting section comprising a multi-stage screen and configured to be in fluid communication with the waterway so as to obtain and process the fluid flow as a subset of the overall flow in the waterway, the multi-stage screen separating organisms by size, whereby relatively larger organisms are returned to the waterway and relatively smaller organisms remain in the fluid flow;
    a velocity control section in fluid communication with the sorting section for receipt therefrom of the fluid flow containing the relatively smaller organisms, the velocity control section comprising an expanding velocity control chute and configured to regulate the fluid flow from the waterway;
    a shepherding section in fluid communication with the velocity control section and configured for separating organisms from the fluid flow;
    a flow normalizing section in fluid communication with the velocity control section and/or the shepherding section, the flow normalizing section comprising a tapered inlet chute; and
    a viewing section in fluid communication with and downstream of the flow normalizing section, the viewing section comprising a body having formed therein a body cavity defining a viewing port visible through a cavity first opening formed in the body so as to be in communication with the body cavity, a viewing section body inlet and an opposite viewing section body outlet both being further formed in the body so as to be in communication with the body cavity and provide an unobstructed flow path therebetween through the viewing port, the viewing section further comprising an optical system mounted relative to the body for viewing the fluid flow within the viewing port through the cavity first opening; and wherein:
    the viewing section is configured in cooperation with the flow normalizing section and the optical system such that multiple frames of image data relating to the fluid flow and a discrete organism therein are acquired via the optical system for analysis; and
    the shepherding section is configured in cooperation with the viewing section and/or the velocity control section for collection and relocation and/or eradication of select organisms within the fluid flow.

2. The system of claim 1 wherein the flow normalizing section and the viewing section are co-located with the velocity control section.

3. The system of claim 1 wherein the flow normalizing section and the viewing section are downstream of the velocity control section, between the velocity control section and the shepherding section.

4. The system of claim 1 wherein the sorting section comprises a two-stage screen having a first screen of relatively larger mesh upstream in the waterway and a second screen of relatively smaller mesh downstream in the waterway.

5. The system of claim 4 wherein the second screen is formed having a V-shaped configuration configured to funnel the relatively smaller organisms within the fluid flow toward the velocity control section.

6. The system of claim 5 wherein the first screen is configured to prevent the relatively larger organisms from passing into the fluid flow from the waterway.

7. The system of claim 4 further comprising a second sorting section also comprising a two-stage screen and a second velocity control section downstream of the second sorting section.

8. The system of claim 1 wherein the velocity control chute of the velocity control section is downstream of and coupled to the multi-stage screen and upstream of the shepherding section, the velocity control chute comprising substantially vertical walls that diverge downstream toward the shepherding section.

9. The system of claim 8 wherein the multi-stage screen defines a downstream opening that is contiguous with an inlet to the velocity control section defined by spaced-apart upstream ends of the velocity control chute walls.

10. The system of claim 9 wherein the screen downstream opening and the velocity control chute upstream inlet are together adjustable.

11. The system of claim 10 wherein the upstream ends of the velocity control chute walls are mounted on offset vertical posts, the screen downstream opening being mechanically coupled to the posts.

12. The system of claim 8 wherein the velocity control section further comprises a velocity control pumping assembly.

13. The system of claim 12 wherein the velocity control pumping assembly comprises a closed fluidic channel that is in fluid communication at a first end with the velocity control chute and at an opposite second end with a pump having a discharge for discharging water from the channel through the pump back into the waterway, whereby the pump is configured to act as a throttle for the fluid flow and thus being capable of regulating the fluid flow within the velocity control chute.

14. The system of claim 12 wherein the velocity control pumping assembly is downstream of the shepherding section.

15. The system of claim 8 further comprising an attractant positioned within the velocity control chute for attracting the organisms within the fluid flow into the velocity control section.

16. The system of claim 1 wherein the shepherding section is in series between the velocity control section and the flow normalizing section.

17. The system of claim 1 wherein the shepherding section comprises a conveyor with spaced-apart buckets installed thereon.

18. The system of claim 1 further comprising an outlet section in fluid communication with and downstream of the viewing section and/or the shepherding section, the outlet section comprising an outlet pipe configured for delivering at least a portion of the fluid flow and any organisms therein to a collection container for storage and eventual relocation or eradication of the organisms.

19. An organism evaluation system for analyzing and processing organisms within a fluid flow of a waterway, comprising:
  a velocity control section configured for receipt of the fluid flow containing organisms and to regulate the fluid flow from the waterway, the velocity control section comprising a velocity control pumping assembly;
  a shepherding section in fluid communication with the velocity control section and configured for separating organisms from the fluid flow;
  a flow normalizing section in fluid communication with the velocity control section and/or the shepherding section, the flow normalizing section comprising a tapered inlet chute; and
  a viewing section in fluid communication with and downstream of the flow normalizing section, the viewing section comprising a body having formed therein a body cavity defining a viewing port visible through a cavity first opening formed in the body so as to be in communication with the body cavity, a viewing section body inlet and an opposite viewing section body outlet both being further formed in the body so as to be in communication with the body cavity and provide an unobstructed flow path therebetween through the viewing port, the viewing section further comprising an optical system mounted relative to the body for viewing the fluid flow within the viewing port through the cavity first opening; and wherein:
  the flow normalizing section and the viewing section are downstream of the velocity control section, between the velocity control section and the shepherding section;
  the viewing section is configured in cooperation with the flow normalizing section and the optical system such that multiple frames of image data relating to the fluid flow and a discrete organism therein are acquired via the optical system for analysis; and
  the shepherding section is configured in cooperation with the viewing section and/or the velocity control section for collection and relocation and/or eradication of select organisms within the fluid flow.

20. An organism evaluation system for analyzing and processing organisms within a fluid flow of a waterway, comprising:
  a shepherding section configured for separating organisms from the fluid flow;
  a flow normalizing section in fluid communication with the shepherding section, the flow normalizing section comprising a tapered inlet chute;
  a viewing section in fluid communication with and downstream of the flow normalizing section, the viewing section comprising a body having formed therein a body cavity defining a viewing port visible through a cavity first opening formed in the body so as to be in communication with the body cavity, a viewing section body inlet and an opposite viewing section body outlet both being further formed in the body so as to be in communication with the body cavity and provide an unobstructed flow path therebetween through the viewing port, the viewing section further comprising an optical system mounted relative to the body for viewing the fluid flow within the viewing port through the cavity first opening; and
  an outlet section in fluid communication with and downstream of the viewing section and/or the shepherding section, the outlet section comprising an outlet pipe configured for delivering at least a portion of the fluid flow and any organisms therein to a collection container for storage and eventual relocation or eradication of the organisms; and wherein:
  the viewing section is configured in cooperation with the flow normalizing section and the optical system such that multiple frames of image data relating to the fluid flow and a discrete organism therein are acquired via the optical system for analysis; and the shepherding section is configured in cooperation with the viewing section and the outlet section for collection and relocation and/or eradication of select organisms within the fluid flow.

* * * * *